(12) United States Patent
Wang et al.

(10) Patent No.: US 10,472,386 B2
(45) Date of Patent: *Nov. 12, 2019

(54) BILE ACID DERIVATIVES AS FXR AGONISTS AND METHODS OF USE THEREOF

(71) Applicant: Enanta Pharmaceuticals, Inc., Watertown, MA (US)

(72) Inventors: Guoqiang Wang, Belmont, MA (US); Yat Sun Or, Watertown, MA (US); Ruichao Shen, Belmont, MA (US); Xuechao Xing, Wilmington, MA (US); Jiang Long, Wayland, MA (US); Peng Dai, Auburndale, MA (US); Brett Granger, Sudbury, MA (US); Jing He, Somerville, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/896,400

(22) Filed: Feb. 14, 2018

(65) Prior Publication Data

US 2018/0237471 A1    Aug. 23, 2018

Related U.S. Application Data

(60) Provisional application No. 62/458,993, filed on Feb. 14, 2017.

(51) Int. Cl.
| | | |
|---|---|---|
| *C07J 41/00* | (2006.01) | |
| *C07J 9/00* | (2006.01) | |
| *C07J 43/00* | (2006.01) | |
| *C07J 51/00* | (2006.01) | |

(52) U.S. Cl.
CPC ......... *C07J 41/005* (2013.01); *C07J 41/0055* (2013.01); *C07J 43/003* (2013.01); *C07J 9/005* (2013.01); *C07J 51/00* (2013.01)

(58) Field of Classification Search
CPC ...... C07J 9/005; C07J 41/0055; C07J 41/005; C07J 43/003; C07J 51/00; C07J 71/0005
See application file for complete search history.

(56) References Cited

U.S. PATENT DOCUMENTS

| | | | |
|---|---|---|---|
| 4,202,876 | A | 5/1980 | Monks et al. |
| 5,466,815 | A | 11/1995 | Enhsen et al. |
| 5,512,558 | A | 4/1996 | Enhsen et al. |
| 5,646,316 | A | 7/1997 | Jacobson et al. |
| 5,656,277 | A | 8/1997 | Berlati et al. |
| 2005/0054559 | A1 | 3/2005 | Gallop et al. |
| 2007/0142340 | A1 | 6/2007 | Pellicciari |
| 2008/0039435 | A1 | 2/2008 | Pellicciari |
| 2008/0182832 | A1 | 7/2008 | Pellicciari et al. |
| 2008/0214515 | A1 | 9/2008 | Ferrari et al. |
| 2009/0062526 | A1 | 3/2009 | Yu et al. |
| 2009/0163474 | A1 | 6/2009 | Zhang et al. |
| 2010/0063018 | A1 | 3/2010 | Pellicciari et al. |
| 2010/0324004 | A1 | 12/2010 | McLane et al. |
| 2011/0172198 | A1 | 7/2011 | Pellicciari |
| 2013/0116218 | A1 | 5/2013 | Kaplan et al. |
| 2013/0345188 | A1 | 12/2013 | Steiner et al. |
| 2014/0057886 | A1 | 2/2014 | Pellicciari et al. |
| 2014/0186438 | A1 | 7/2014 | Manku et al. |
| 2014/0187633 | A1 | 7/2014 | Manku et al. |
| 2014/0206657 | A1 | 7/2014 | Yu et al. |
| 2014/0371190 | A1 | 12/2014 | Pellicciari et al. |
| 2015/0112089 | A1 | 4/2015 | Finch et al. |
| 2016/0130297 | A1 | 5/2016 | Or et al. |
| 2016/0145295 | A1 | 5/2016 | Or et al. |
| 2016/0145296 | A1 | 5/2016 | Or et al. |
| 2016/0176917 | A1 | 6/2016 | Wang et al. |
| 2016/0185815 | A1 | 6/2016 | Wang et al. |

(Continued)

FOREIGN PATENT DOCUMENTS

| | | |
|---|---|---|
| CN | 105175473 A | 12/2015 |
| CN | 10658946 A | 3/2017 |

(Continued)

OTHER PUBLICATIONS

Macchiarulo, et al., "Probing the Binding Site of Bile Acids in TGR5," Medicinal Chemistry Letters, 4 (12):1158-1162, 2013.

(Continued)

*Primary Examiner* — Barbara P Badio

(74) *Attorney, Agent, or Firm* — Edgar W. Harlan; Carolyn S. Elmore; Elmore Patent Law Group, P.C.

(57) ABSTRACT

The present invention provides compounds represented by Formula I, or pharmaceutically acceptable salts, prodrugs and esters thereof,

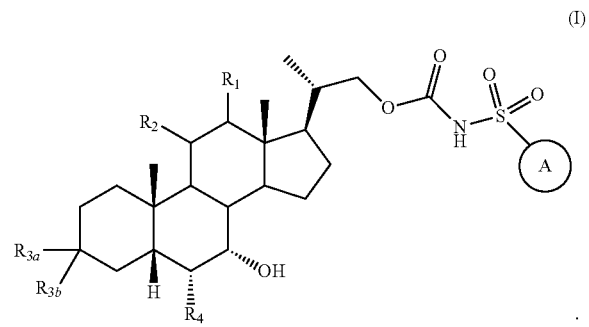

The invention also provides pharmaceutical compositions comprising these compounds and methods of using this compounds for treating FXR-mediated or TGR5-mediated diseases or conditions.

10 Claims, No Drawings

(56) References Cited

U.S. PATENT DOCUMENTS

| | | |
|---|---|---|
| 2016/0229886 A1 | 8/2016 | Shen et al. |
| 2016/0289262 A1 | 10/2016 | Wang et al. |
| 2017/0101434 A1 | 4/2017 | Pellicciari et al. |
| 2017/0240585 A1 | 8/2017 | Wang et al. |
| 2017/0240586 A1 | 8/2017 | Or et al. |
| 2017/0240587 A1 | 8/2017 | Or et al. |
| 2017/0260225 A1 | 9/2017 | Pellicciari et al. |
| 2018/0148469 A1 | 5/2018 | Wang et al. |
| 2018/0148470 A1 | 5/2018 | Li et al. |
| 2018/0291058 A1 | 10/2018 | Wang et al. |

FOREIGN PATENT DOCUMENTS

| | | |
|---|---|---|
| CN | 106478759 A | 3/2017 |
| EP | 583566 A2 | 2/1994 |
| EP | 1364645 A1 | 11/2003 |
| EP | 3290429 A1 | 3/2018 |
| JP | H1160594 A | 3/1999 |
| WO | 198702367 A2 | 4/1987 |
| WO | 2003030612 A2 | 4/2003 |
| WO | 2007111994 A2 | 10/2007 |
| WO | 2008009407 A2 | 1/2008 |
| WO | 2008091540 A2 | 7/2008 |
| WO | 2010014836 A3 | 2/2010 |
| WO | 2013020108 A2 | 2/2013 |
| WO | 2013166176 A1 | 11/2013 |
| WO | 2013192097 A1 | 12/2013 |
| WO | 2014036379 A2 | 3/2014 |
| WO | 2014184271 A1 | 11/2014 |
| WO | 2015017813 A2 | 2/2015 |
| WO | 2015181275 A1 | 12/2015 |
| WO | 2016173493 A2 | 11/2016 |
| WO | 2016173524 A1 | 11/2016 |
| WO | 2016205475 A | 12/2016 |
| WO | 2017027396 A1 | 2/2017 |
| WO | 2017053826 A1 | 3/2017 |
| WO | 2017129125 A1 | 8/2017 |

OTHER PUBLICATIONS

Sato, et al., "Novel Potent and Selective Bile Acid Derivatives as TGR5 Agonists: Biological Screening, Structure-Activity Relationships, and Molecular Modeling Studies," J. Med. Chem., 51:1831-1841, 2008.

Mosesin-4' at www.chemspider.com/ Chemical-Structure.10375019. html (retrieved from the internet Oct. 11, 2016).

Pellicciari, et al., "6α-Ethyl-Chenodeoxycholic Acid (6-ECDCA), a Potent and Selective FXR Agonist Endowed with Anticholestatic Activity," Journal of Medicinal Chemistry, 45(17):3569-3572, 2002.

Silverman, "Prodrugs and Drug Delivery Systems," The Organic Chemistry of Drug Design and Drug Action, pp. 352-399, 1992.

Banker, et al., Modern Pharmaceutics, 3rd edition, 1996.

Bundgaard, "Design of Prodrugs: Bioreversible derivatives for various functional groups and chemical entities," Design of Prodrugs, Chapter 1, 1985.

Wolff, Burger's Medicinal Chemistry and Drug Discovery, 5(1):975-977, 1995.

Kim, et al., "Synthesis and Antimicrobial Activity of New 3α-Hydroxy-23,24-bisnorcholane Polyamine Carbamates," Bioorganic & Medicinal Chemistry Letters, 11:3065-3068, 2001.

Solaja, et al., "Novel 4-Aminoquinolines Active against Chloroquine-Resistant and Sensitive P. falciparum Strains that also Inhibit Botulinum Serotype A," J. Med. Chem., 51:4388-4391, 2008.

Willemen, et al., "Alkyl Derivatives of Cholic Acid as Organogelators: One-Component and Two-Component Gels," Langmuir, 18(19):7102-7106, 2002.

Pore, et al., "Design and synthesis of fluconazole/bile acid conjugate using click reaction", Tetrahedron, 62:11178-11186, 2006.

Nikolaienko, et al., "Rapid way to fluorescent cholic-based chemosensor precursors", Synthetic Organic Chemistry, pp. 1-4, 2011.

Sepe, et al., "Farnesoid X receptor modulators (2011-2014): a patent review," Expert Opinion on Therapeutic Patents, 25:8, 885-896, 2015.

Crawley, "Farnesoid X Receptor Modulators: a patent review," Expert Opinion on Therapeutic Patents, 20(8): 1047-1057, 2010.

Briere, et al., "Novel small molecule agonist of TGR5 possesses anti-diabetic effects but causes gallbladder filling in mice." Plos one, 10(8):1-17, 2015.

Okahata, et al., "Catalytic Hydrolysis of p-Nitrophenyl Esters in the Presence of Representative Ammonium Aggregates. Specific Activation of a Cholesteryl Nucleophile Bound to a Dialkylammonium Bilayer Membrane." Bulletin of hte Chemical Society of Japan, 52(12):3647-3653, 1979.

Sajisha, et al., "Remarkable isomer-selective gelation of aromatic solvents by a polymorph of a urea-linked bile acid-amino acid conjugate," RSC Advances, 4(81):43167-43171, 2014. Abstract only.

Mayorquin-Torres, et al., "Application of palladium-catalyzed carboxyl anhydride-boronic acid cross coupling in the synthesis of novel bile acids analogs with modified side chains". Steroids, (101):21-27, 2015.

U.S. Appl. No. 15/826,233, filed Nov. 29, 2017.

Ali, et al., "Recent advances in the development of farnesoid X receptor agonists," Ann Transl Med, 3(1):5, pp. 1-16, 2015.

PUBCHEM-CID-122592927, Created Date: Dec. 8, 2016.

PUBCHEM-CID-122592945, Created Date: Dec. 8, 2016.

Pellicciari, R., et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", Journal of Medicinal Chemistry, American Chemical Society, 47:4559-4569, 2004.

Okahata, Y., et al., "Base-catalyzed proton abstraction from .beta.-(p-nitrophenoxy)propiophenone in the presence of single-chain, double-chain, and triple-chain ammonium bilayer membrane aggregates", Database CA [Online] Chemical Abstracts Service, Database accession No. 1980:549272, abstract, 1980.

Pellicciari, et al. "Back Door Modulation of the Farnesoid X Receptor: Design, Synthesis and Biological Evaluation of a Series of Side Chain Modified Chenodeoxycholic Acid Derivatives", Journal of Medicinal Chemi, American Chemical Society, 49:4208-4215, 2006.

Gioiello Antimo, et al., "Extending SAR of bile acids as FXR ligands: discovery of 23-N-(carbocinnamyloxy)-3[alpha],7[alpha]dihydroxy-6[alpha]-ethyl-24-nor-5[beta]-cholan-23-amine", Bioorganic & Medicinal Chemistry, 19(8):2650-2658, 2011.

Griffiths, et al., "Charge-remote fragmentation of bile acids derivatized with amino-sulphonic acids," Rapid Communication in Mass Spectrometry, 7(3):235-240, 1993.

Coleman, J. P., et al., "Metabolic Fate and Hepatocyte Toxicity of Reverse Amide Analogs of Conjugated Ursodeoxycholate in the Rat," J. Steroid Biochem. Molec. Biol., 64(1/2): 91-101, 1998.

Opsenica, I. M., et al., "4-Amino-7-chloroquinolines: Probing Ligand Efficiency Provides Botulinum Neurotoxin Serotype A Light Chain Inhibitors with Significant Antiprotozoal Activity," J. Med. Chem., (56):5860-5871, 2013.
F[N], A., et al."Basic Cholane Derivatives. XI: Comparison between Acid and Basic Derivatives," Journal of Pharmaceutical Sciences, (81)7:726-730, 1992.
Fini, A., et al., "Quantitative Structure-Antimicrobial Activity Relationship in 5B-Cholanyl-24-benzylamine Derivatives," Journal of Pharmaceutical Sciences, (79)7:603-605, 1990.
Ballatore, C., et al., "Carboxylic Acid (Bio)Isosteres in Drug Design," ChemMedChem., (8)3: 385-395, 2013.
Honorio, K. M., et al., "Hologram QSAR Studies on Farnesoid X Receptor Activators," Letters in Drug Design & Discovery, (3):261-267, 2006.

BILE ACID DERIVATIVES AS FXR AGONISTS AND METHODS OF USE THEREOF

RELATED APPLICATIONS

This application claims the benefit of U.S. Provisional Application No. 62/458,993, filed on Feb. 14, 2017. The entire teachings of the above application are incorporated herein by reference.

TECHNICAL FIELD

The present invention relates generally to compounds useful as FXR modulators and pharmaceutical compositions thereof. Specifically, the present invention relates to bile acid derivatives and methods for their preparation and use.

BACKGROUND OF THE INVENTION

Farnesoid X Receptor (FXR) is an orphan nuclear receptor initially identified from a rat liver cDNA library (B M. Forman, et al., Cell, 1995, 81(5), 687-693) that is most closely related to the insect ecdysone receptor. FXR is a member of the nuclear receptor family of ligand-activated transcription factors that includes receptors for the steroid, retinoid, and thyroid hormones (D J. Mangelsdorf, et al., Cell, 1995, 83(6), 841-850). The relevant physiological ligands of FXR are bile acids (D. Parks et al., Science, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., Genes Dev., 2003, 17(13), 1581-1591; T. Inagaki et al., Cell Metab., 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/073767, WO 2016/116054, WO 2016/103037, WO 2016/096116, WO 2016/096115, WO 2016/097933, WO 2016/081918, WO 2016/127924, WO 2016/130809, WO 2016/145295, WO 2016/173524, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/129125, WO 2017/133521, WO 2017/147074, WO 2017/147174, WO 2017/145041, and WO 2017/156024 A1.

Further small molecule FXR modulators have been recently reviewed (R. C. Buijsman, et al., Curr. Med. Chem. 2005, 12(9), 1017-1075; Crawley, M. L. Expert Opin. Ther. Patents 2010, 20(8), 1047-1057; V. Sepe, et al., Expert Opin. Ther. Patents 2015, 25(8), 885-896; Xu, Y., J. Med. Chem. 2016, 59 (14), 6553-6579). There is a need for the development of FXR modulators for the treatment and prevention of disease. The present invention has identified compounds, which contain a sulfonyl carbamate moiety, which modulate FXR as well as methods of using these compounds to treat diseases.

SUMMARY OF THE INVENTION

The invention provides compounds represented by Formula I pharmaceutically acceptable salts, esters and prodrugs thereof:

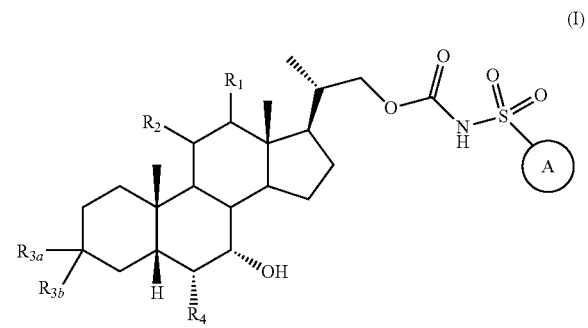

(I)

wherein:

A is

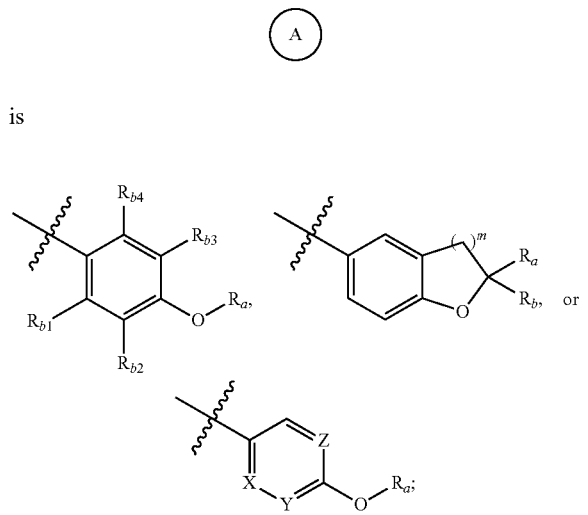

Each $R_a$ and $R_b$ is independently selected from the group consisting of:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted aryl;
7) Optionally substituted arylalkyl;
8) Optionally substituted 3- to 8-membered heterocycloalkyl;
9) Optionally substituted heteroaryl; and
10) Optionally substituted heteroarylalkyl;

$R_{b1}$, $R_{b2}$, $R_{b3}$, and $R_{b4}$ are independently selected from hydrogen, halogen and optionally substituted —$C_1$-$C_8$ alkyl; m is selected from 1, 2 or 3;

X, Y, and Z are independently selected from $CR_{b1}$ or N, wherein $R_{b1}$ is previously defined; preferably at least one of X, Y and Z is N;

$R_1$ is optionally substituted $C_1$-$C_6$ alkyl, hydrogen, hydroxyl, —$OSO_3H$, —$OSO_3$, —OAc, —$OPO_3H_2$ or —$OPO_3^{2-}$; preferably $R_1$ is hydrogen;

$R_2$ is optionally substituted $C_1$-$C_6$ alkyl, hydrogen, halogen, CN, $N_3$, hydroxyl, —$OSO_3H$, —$OSO_3$, —OAc, —$OPO_3H_2$, —$OPO_3^{2-}$, —$SR_a$ or —$NHR_a$, wherein $R_a$ is previously defined; preferably $R_2$ is hydrogen, alternatively, $R_1$ and $R_2$ are taken together with the carbon atoms to which they attached to form —CH=CH— or cycloalkyl ring or heterocycloalkyl ring such as, but not limited to cyclopropyl, or epoxide.

$R_{3a}$ and $R_{3b}$ are independently selected from hydrogen, hydroxyl, optionally substituted $C_1$-$C_6$ alkyl, or optionally substituted —O—$C_1$-$C_6$ alkyl; preferably $R_{3a}$ is α-hydroxyl and $R_{3b}$ is hydrogen, alternatively, $R_{3a}$ and $R_{3b}$ are taken together with the carbon atom to which they attached to form —C(O);

$R_4$ is selected from the group consisting of:
1) Hydrogen;
2) Halogen;
3) Optionally substituted —$C_1$-$C_8$ alkyl;
4) Optionally substituted —$C_2$-$C_8$ alkenyl;
5) Optionally substituted —$C_2$-$C_8$ alkynyl; and
6) Optionally substituted —$C_3$-$C_8$ cycloalkyl;
preferably $R_4$ is hydrogen or ethyl;

Each preferred group stated above can be taken in combination with one, any or all other preferred groups.

In another embodiment, the present invention provides a pharmaceutical composition comprising a therapeutically effective amount of a compound the present invention, or a pharmaceutically acceptable salt, ester or prodrug thereof, in combination with a pharmaceutically acceptable carrier or excipient.

In another embodiment, the present invention provides a method for preventing or treating an FXR mediated disease or condition in a subject in need thereof. The method comprises administering to the subject a therapeutically effective amount of a compound of the invention. The present invention also provides the use of a compound of formula (I) for the preparation of a medicament for preventing or treating an FXR mediated disease or condition.

In certain embodiments, an FXR mediated disease is selected from metabolic disease, inflammatory disease, liver disease, autoimmune disease, cardiac disease, kidney disease, cancer, and gastrointestinal disease.

DETAILED DESCRIPTION OF THE INVENTION

A first embodiment of the invention is a compound represented by Formula (I) as described above, or a pharmaceutically acceptable salt, ester or prodrug thereof.

In one embodiment, the invention is a compound represented by Formula (I), or a pharmaceutically acceptable salt, ester or prodrug thereof, wherein $R_1$ is hydrogen. In another embodiment, the invention is a compound represented by Formula (I), or a pharmaceutically acceptable salt, ester or prodrug thereof, wherein $R_2$ is hydrogen. In another embodiment, the invention is a compound represented by Formula (I), or a pharmaceutically acceptable salt, ester or prodrug thereof, wherein both $R_1$ and $R_2$ are hydrogen.

In one embodiment, the invention is a compound represented by Formula (I), or a pharmaceutically acceptable salt, ester or prodrug thereof, wherein $R_4$ is hydrogen. In another embodiment, the invention is a compound represented by Formula (I), or a pharmaceutically acceptable salt, ester or prodrug thereof, wherein $R_4$ is ethyl.

In one embodiment, the invention is a compound represented by Formula (I), or a pharmaceutically acceptable salt, ester or prodrug thereof, wherein one of $R_1$ and $R_2$ is hydrogen, $R_4$ is hydrogen or ethyl.

In one embodiment, the invention is a compound represented by Formula (I), or a pharmaceutically acceptable salt, ester or prodrug thereof, wherein both $R_1$ and $R_2$ are hydrogen, $R_4$ is hydrogen or ethyl.

In one embodiment, the invention is a compound represented by Formula (I), or a pharmaceutically acceptable salt, ester or prodrug thereof, wherein both $R_1$ and $R_2$ are hydrogen, one of $R_{3a}$ and $R_{3b}$ is hydroxyl, and $R_4$ is hydrogen or ethyl.

In certain embodiments, $R_a$ is not t-butyl, trifluoromethyl, hydrogen, methyl or phenyl.

In one embodiment, the invention is a compound represented by Formula (I), or a pharmaceutically acceptable salt, ester or prodrug thereof, wherein

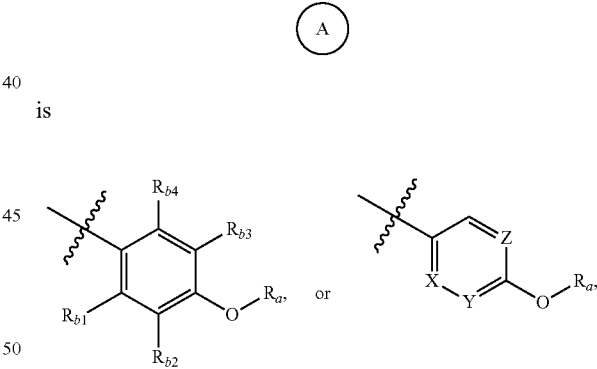

is wherein $R_{b1}$, $R_{b2}$, $R_{b3}$, $R_{b4}$, X, Y, and Z are previously defined, $R_a$ is selected from optionally substituted $C_1$-$C_4$-alkyl, optionally substituted $C_1$-$C_4$-alkenyl, optionally substituted $C_3$-$C_6$-cycloalkyl, optionally substituted 3- to 8-membered heterocycloalkyl, optionally substituted aryl, or optionally substituted heteroaryl.

In one embodiment, the invention is a compound represented by Formula (I), or a pharmaceutically acceptable salt, ester or prodrug thereof, wherein is

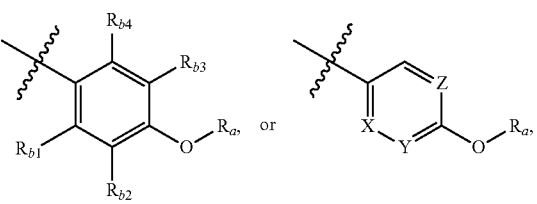

wherein $R_{b1}$, $R_{b2}$, $R_{b3}$, $R_{b4}$, X, Y, and Z are previously defined, $R_a$ is selected from hydrogen, methyl, ethyl, propyl, isopropyl, butyl, 2-butyl, t-butyl, 3-pentyl, vinyl, allyl, $CF_3$ or below:

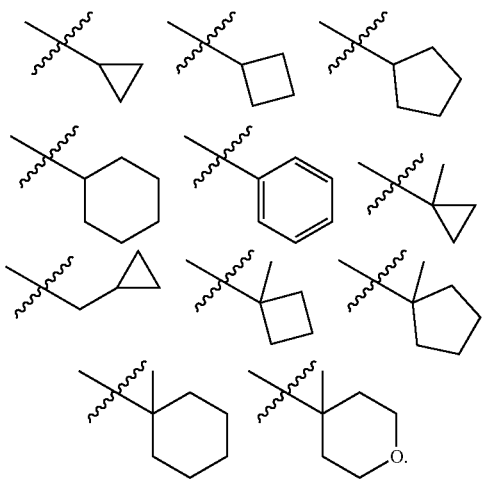

In one embodiment, the invention is a compound represented by Formula (I), or a pharmaceutically acceptable salt, ester or prodrug thereof, wherein (A)

is selected from:

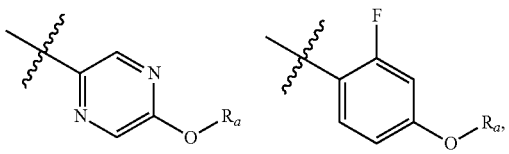

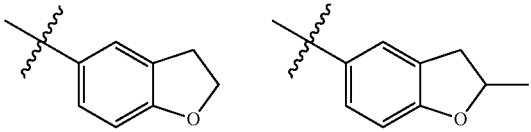

wherein $R_a$ is previously defined.

In one embodiment, the invention is a compound represented by Formula (I), or a pharmaceutically acceptable salt, ester or prodrug thereof, wherein (A)

is selected from the groups below.

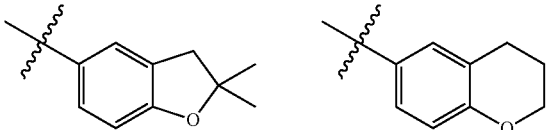

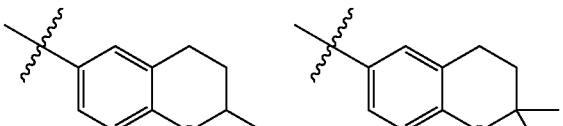

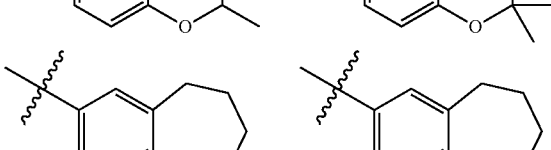

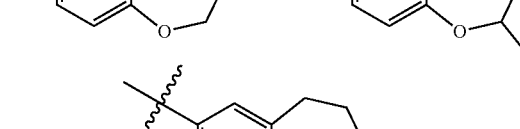

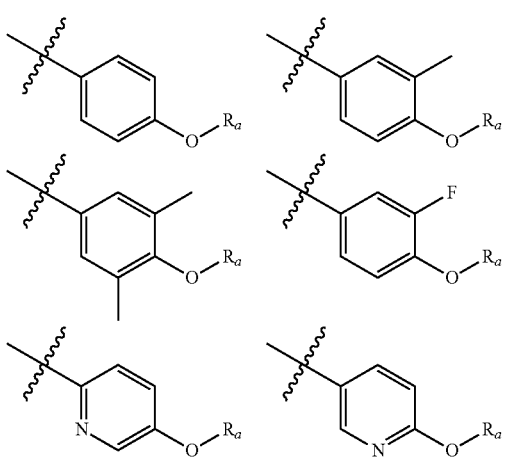

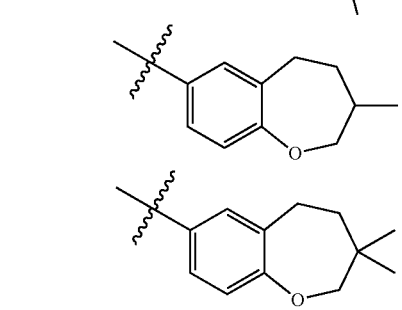

In another embodiment, the compound of Formula (I) is represented by Formula (Ia) and (Ib), or a pharmaceutically acceptable salt, ester or prodrug thereof:

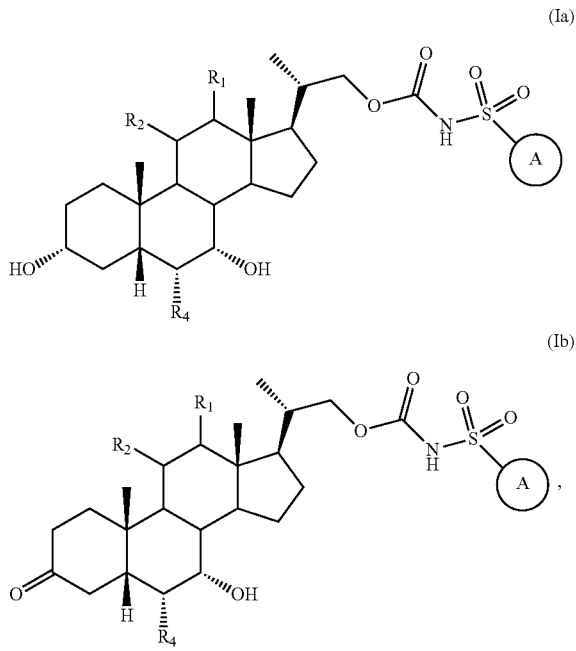

(Ia)

(Ib)

wherein $R_1$, $R_2$, $R_4$, and

are previously defined. Preferably $R_1$ and $R_2$ are both hydrogen and $R_4$ is ethyl.

In certain embodiments, the invention provides compounds represented by Formula (IIa) or Formula (IIb), and pharmaceutically acceptable salts, esters and prodrugs thereof:

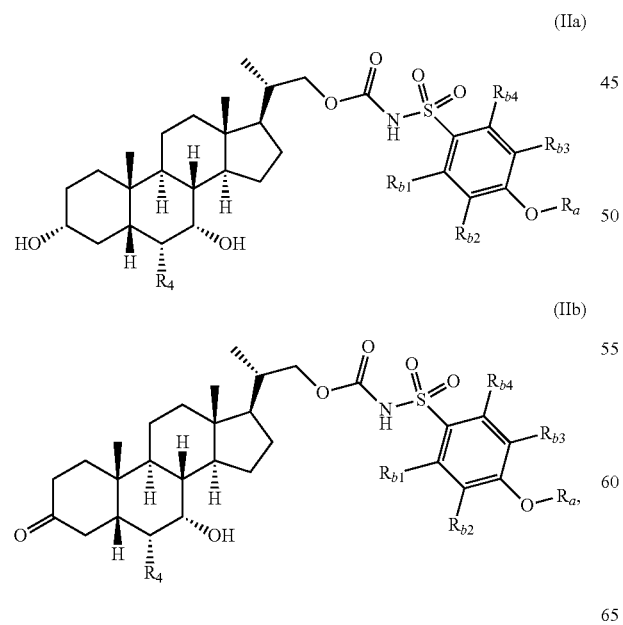

(IIa)

(IIb)

wherein $R_4$, $R_{b1}$, $R_{b2}$, $R_{b3}$, $R_{b4}$ and $R_a$ are as previously defined. Preferably $R_4$ is ethyl or hydrogen; more preferably $R_4$ is ethyl. In certain embodiments, $R_{b1}$, $R_{b2}$, $R_{b3}$ and $R_{b4}$ are each hydrogen or methyl. In certain embodiments, $R_{b1}$, $R_{b2}$, $R_{b3}$ and $R_{b4}$ are each hydrogen.

In certain embodiments, the present invention relates to compounds of Formula (I) represented by Formula (IIa) or Formula (IIb), and pharmaceutically acceptable salts, esters and prodrug thereof, wherein $R_a$ is optionally substituted $C_1$-$C_4$-alkyl, optionally substituted $C_1$-$C_4$-alkenyl, optionally substituted $C_3$-$C_6$-cycloalkyl, optionally substituted heteroaryl, such as 5- or 6-membered heteroaryl; or optionally substituted aryl, such as optionally substituted phenyl or naphthyl, $R_{b1}$, $R_{b2}$, $R_{b3}$, and $R_{b4}$ are independently hydrogen, or optionally substituted $C_1$-$C_4$-alkyl, and $R_4$ is hydrogen or ethyl.

Representative compounds of the invention include, but are not limited to, the following compounds according to Formula (IIa) and pharmaceutically acceptable salts, esters and prodrugs thereof.

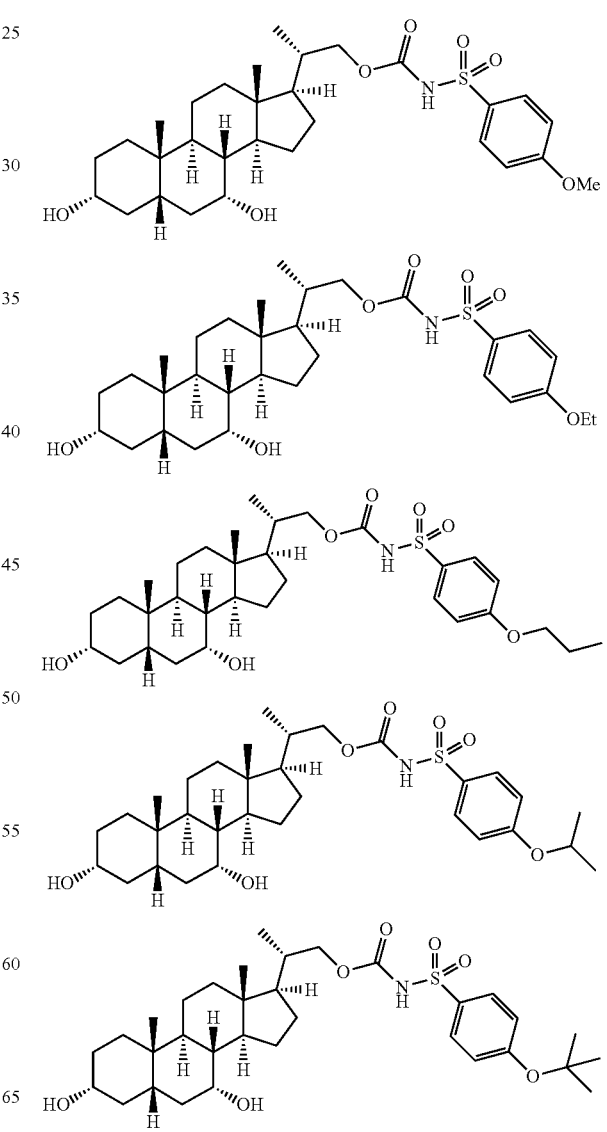

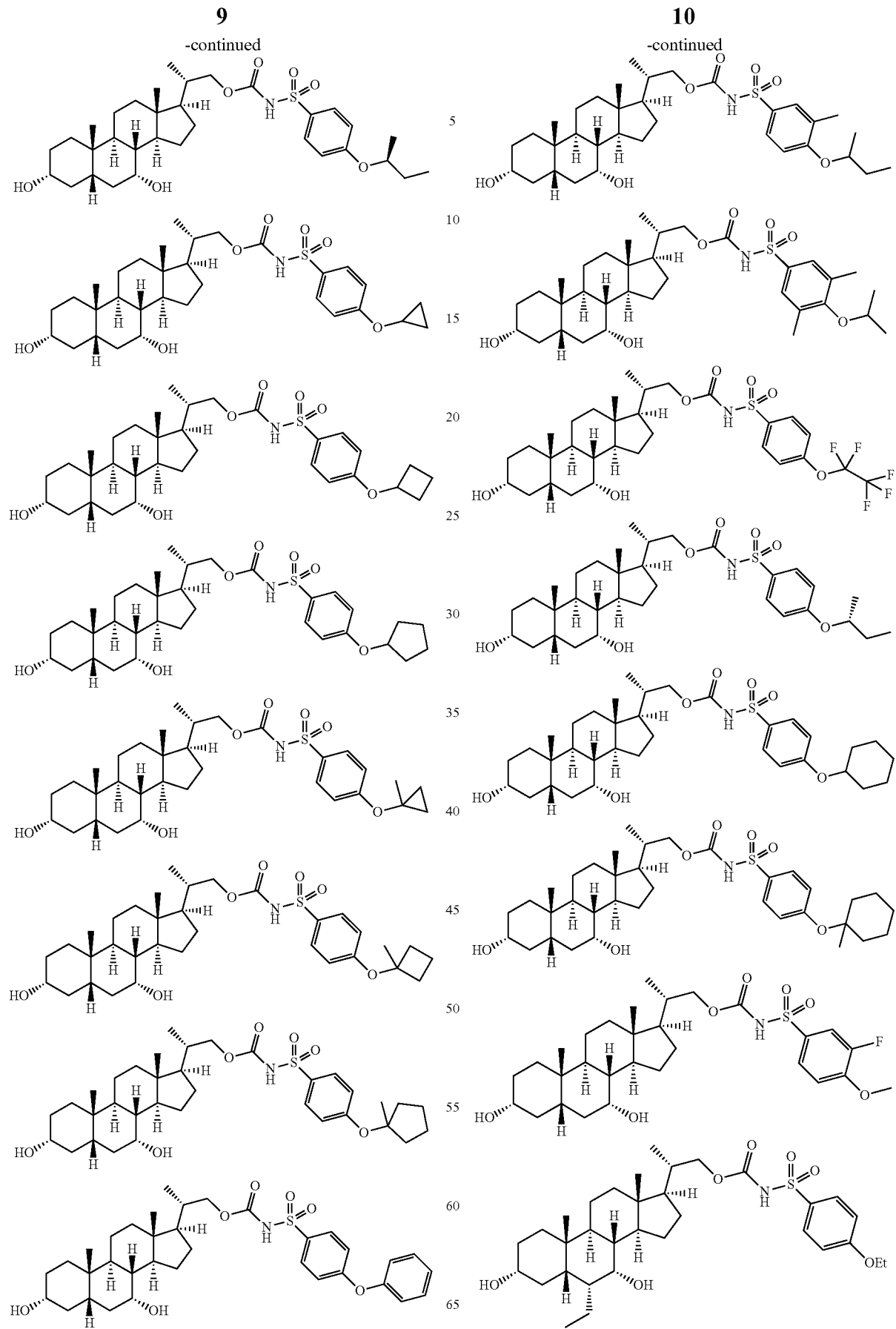

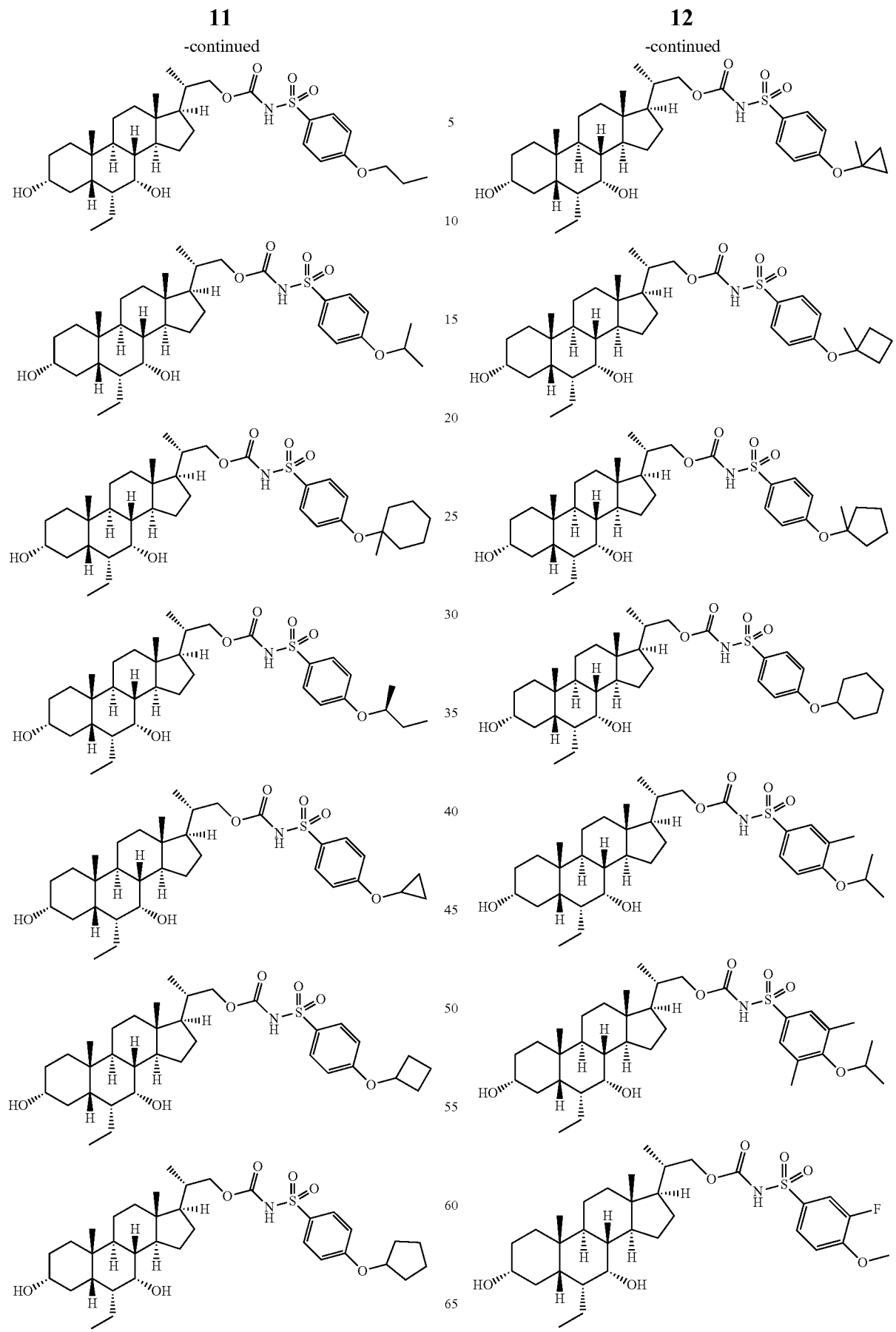

-continued

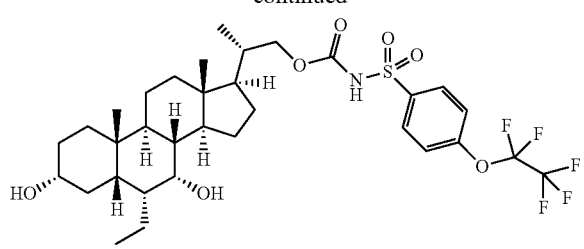

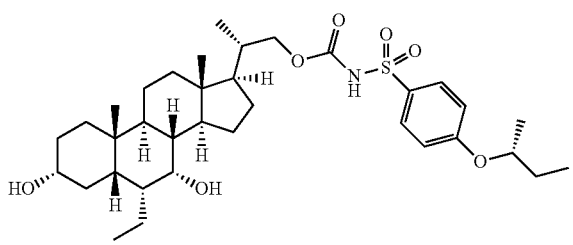

In certain embodiments, the compounds of the invention do not include one or more of the compounds set forth below:

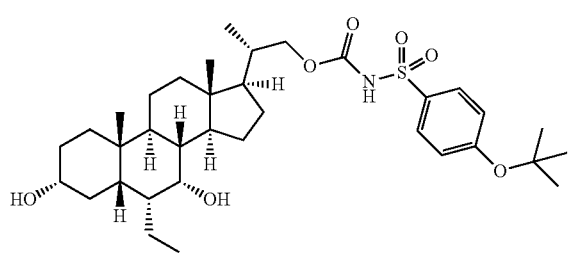

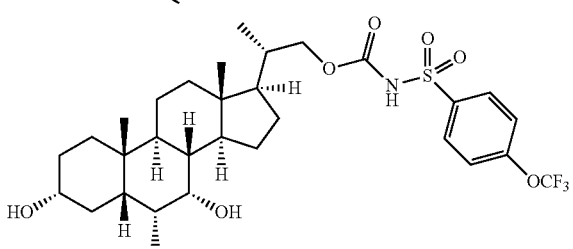

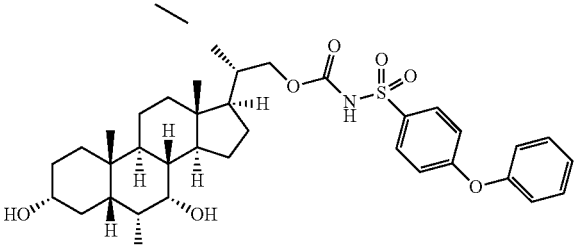

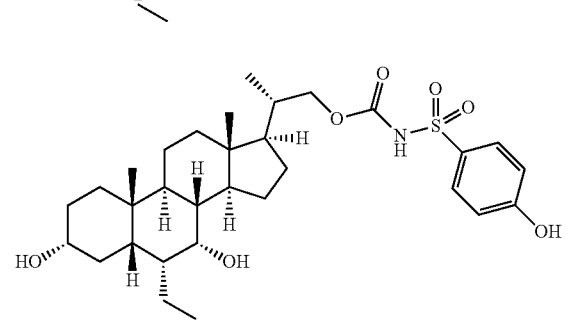

-continued

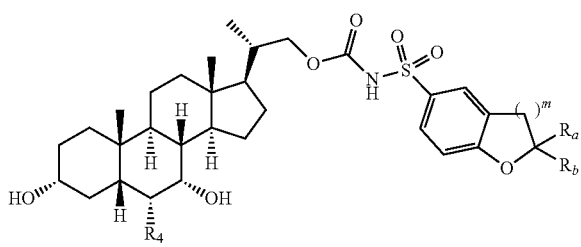

In certain embodiments, the invention provides compounds represented by Formula (IIIa) or Formula (IIIb), and pharmaceutically acceptable salts, esters and prodrugs thereof, (IIIa)

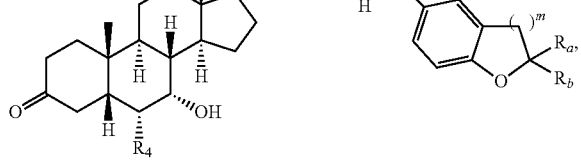

(IIIb)

wherein $R_4$, $R_a$, $R_b$, and m are as previously defined. In certain embodiments, $R_4$ is ethyl. In certain embodiments $R_a$ and $R_b$ are independently $C_1$-$C_3$-alkyl, preferably methyl or ethyl. In certain embodiments, $R_a$ and $R_b$ are both methyl. In certain embodiments, $R_4$ is ethyl and $R_a$ and $R_b$ are independently $C_1$-$C_3$-alkyl, preferably methyl or ethyl. In certain embodiments, $R_a$ and $R_b$ have any of the foregoing meanings and are independently optionally substituted with hydroxyl.

In certain embodiments, the present invention relates to compounds of Formula (I) represented by Formula (IIIa) or Formula (IIIb), and pharmaceutically acceptable salts, esters or prodrugs thereof, wherein $R_a$ and $R_b$ are independently optionally substituted $C_1$-$C_4$-alkyl, optionally substituted $C_1$-$C_4$-alkenyl, optionally substituted $C_3$-$C_6$-cycloalkyl; optionally substituted heteroaryl, such as 5- or 6-membered heteroaryl; or optionally substituted aryl, such as optionally substituted phenyl or naphthyl; m is 1 or 2, and $R_4$ is hydrogen or ethyl.

Representative compounds of the invention include, but are not limited to, the following compounds and pharmaceutically acceptable salts, esters and prodrugs thereof.

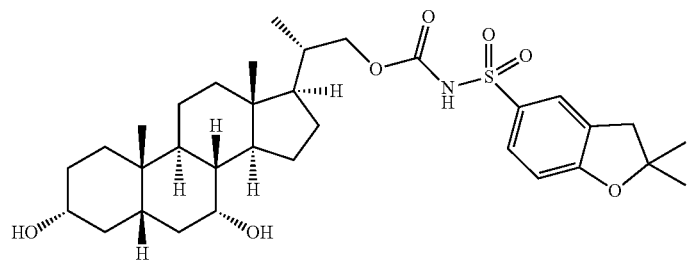
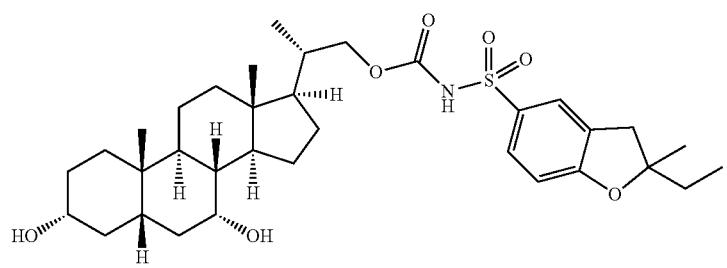
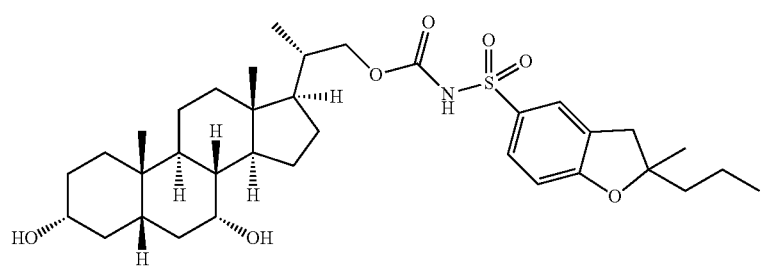
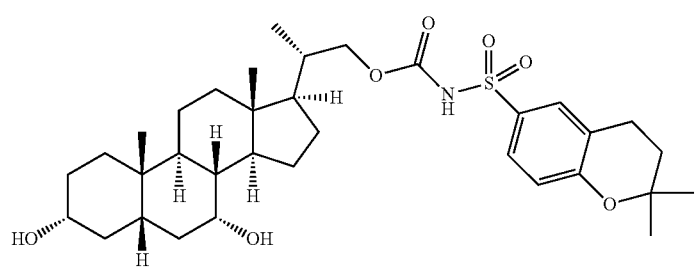
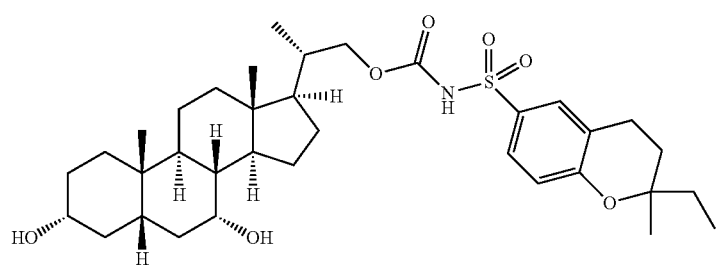
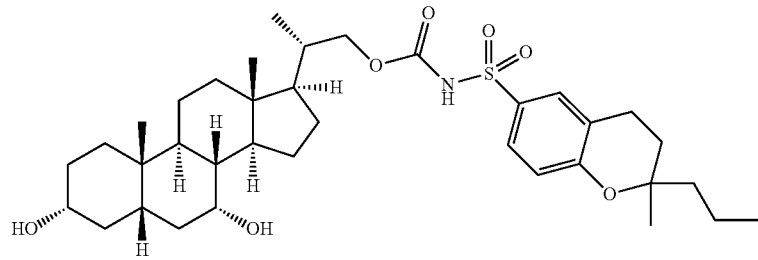

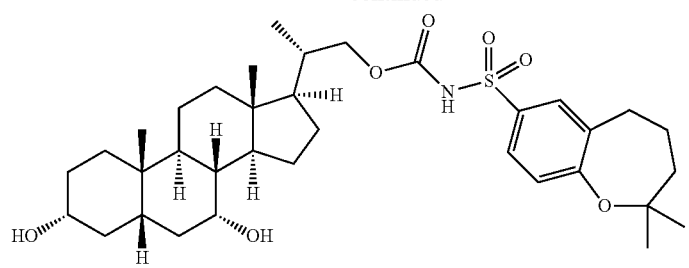
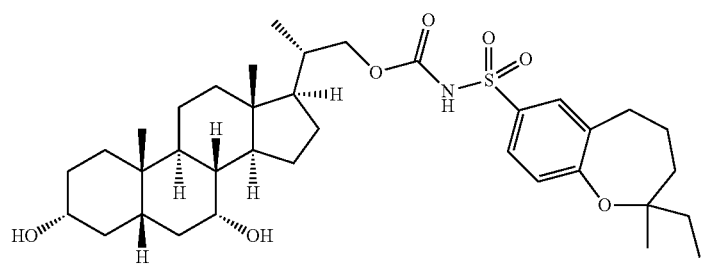
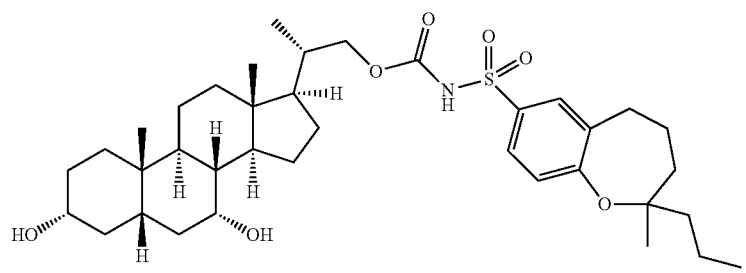
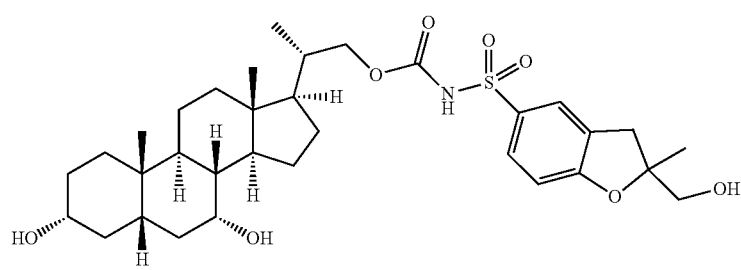
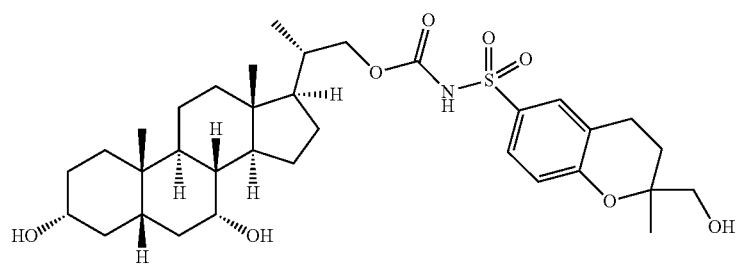
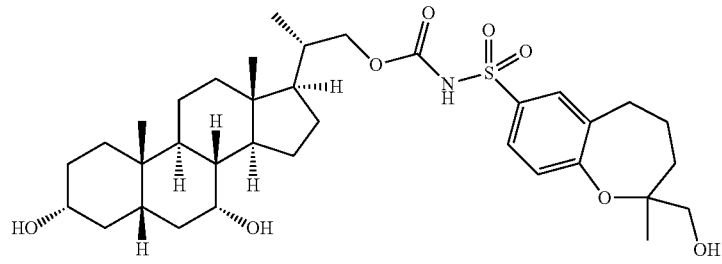

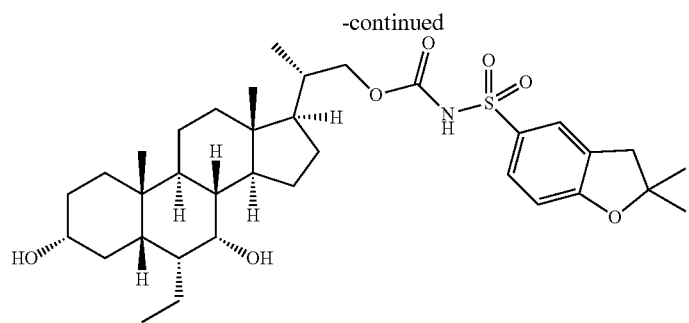
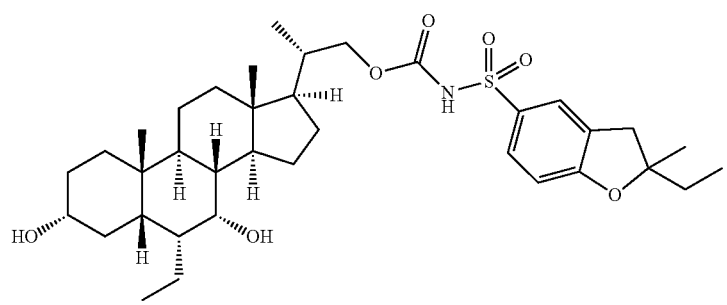
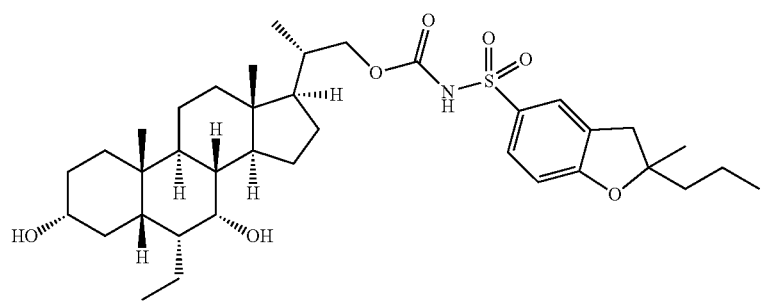
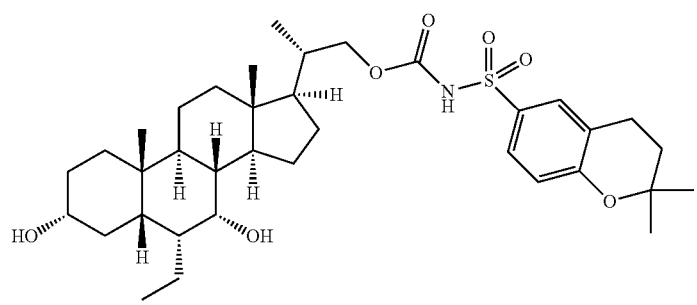
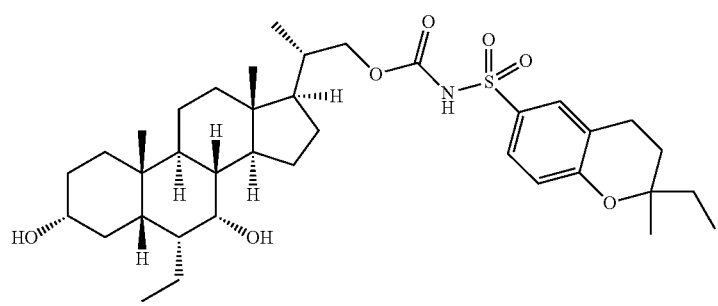

-continued
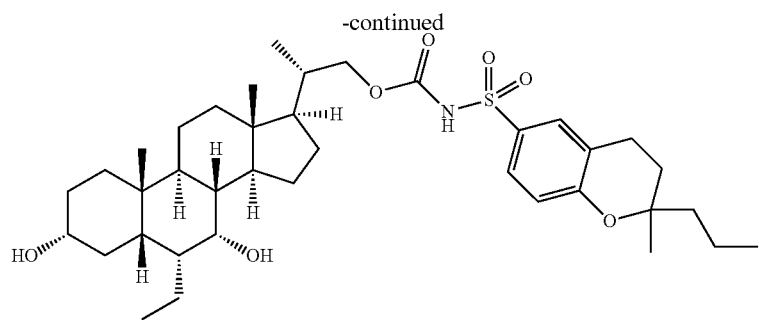
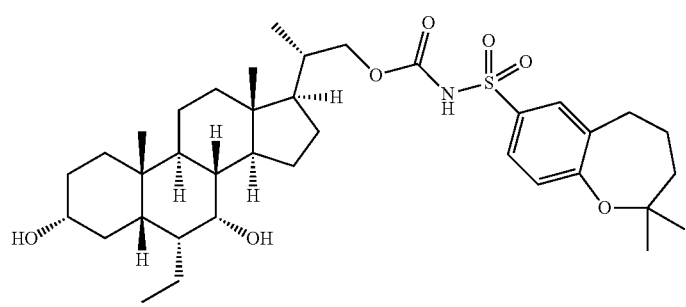
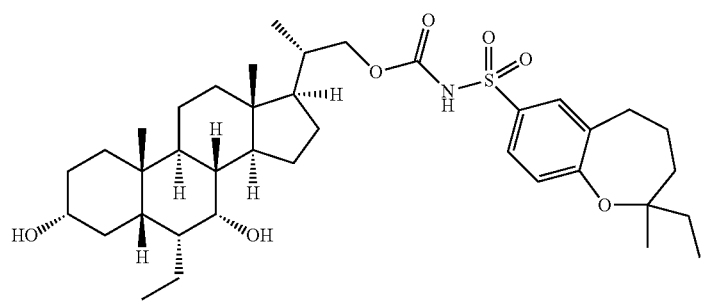
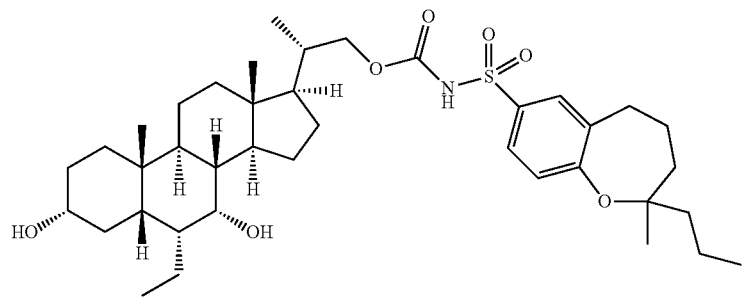
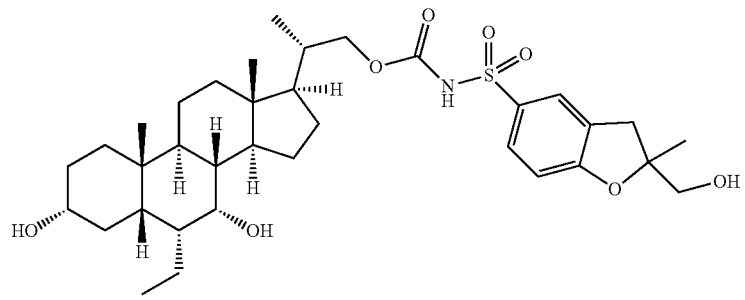

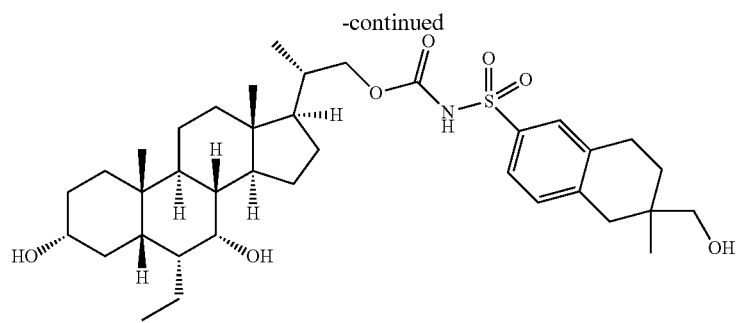

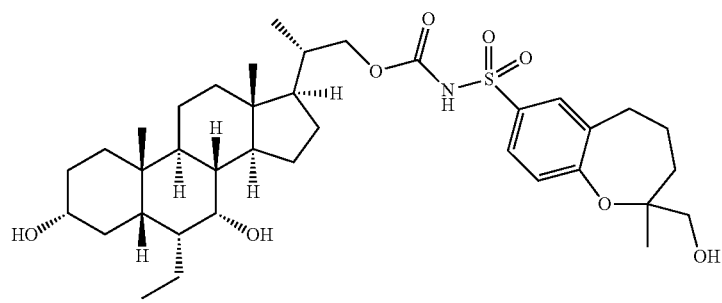

In certain embodiments, the invention provides compounds represented by Formula (IVa) or Formula (IVb), and pharmaceutically acceptable salts esters and prodrugs thereof,

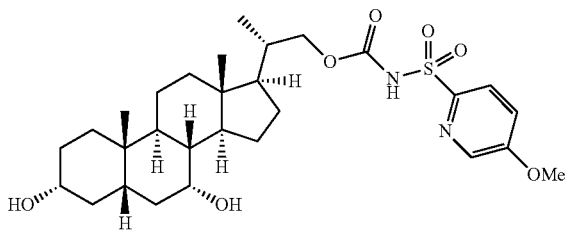

(IVa)

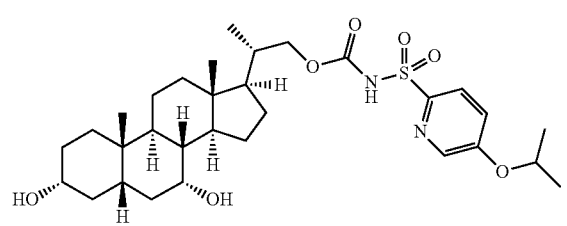

(IVb)

wherein $R_a$, X, Y, Z and $R_4$ are as previously defined. Preferably $R_4$ is hydrogen or ethyl.

Representative compounds of the invention include, but are not limited to, the following compounds and pharmaceutically acceptable salts, esters and prodrugs thereof.

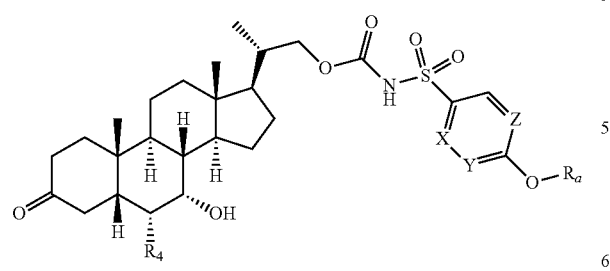

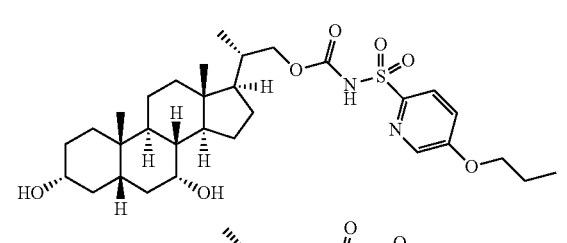

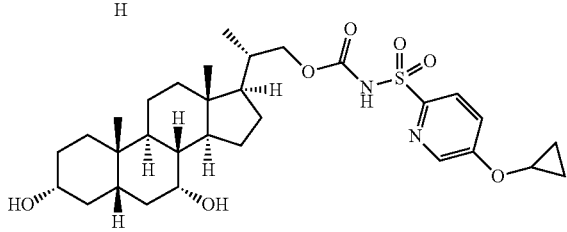

25
-continued
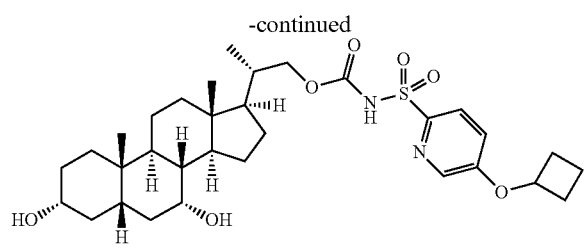
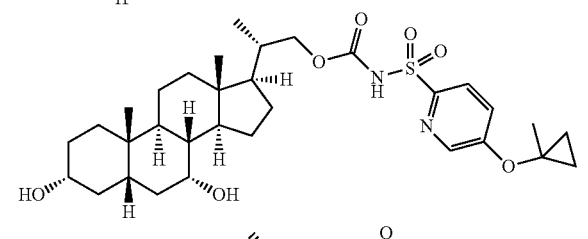
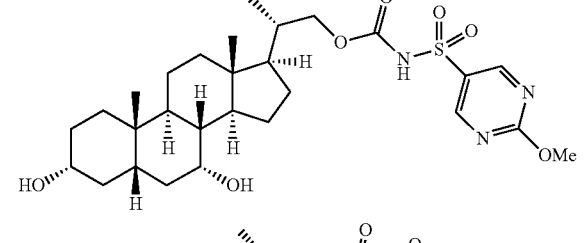
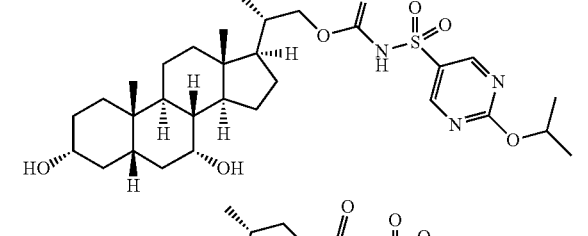
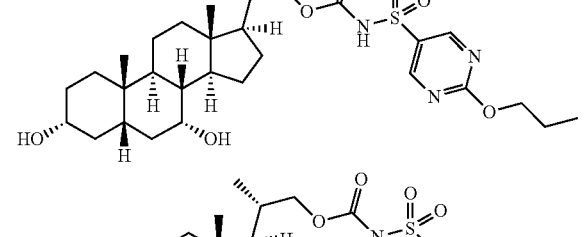
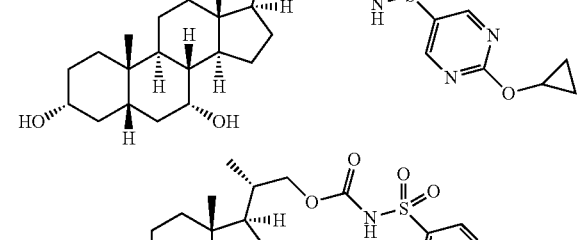
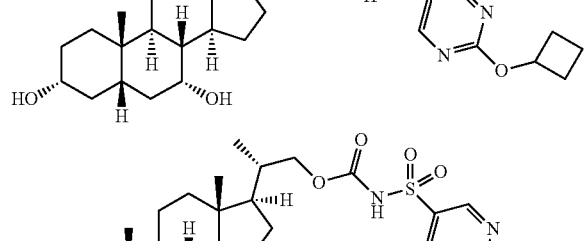
26
-continued
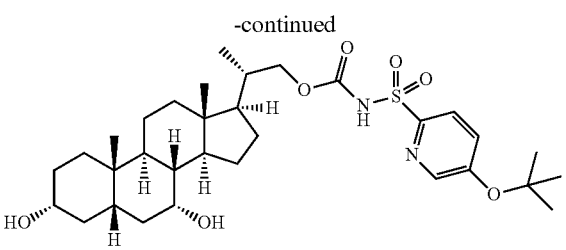
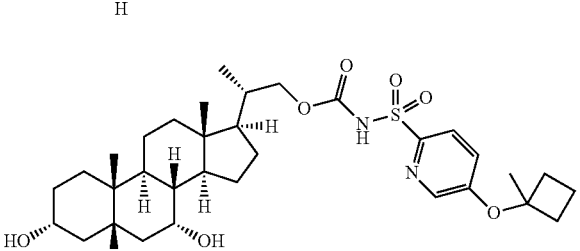
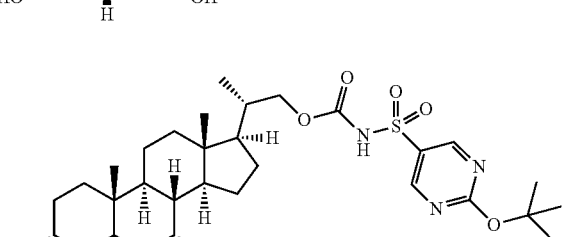
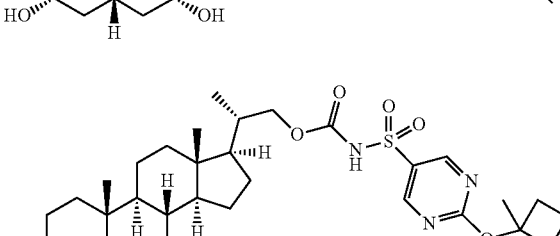
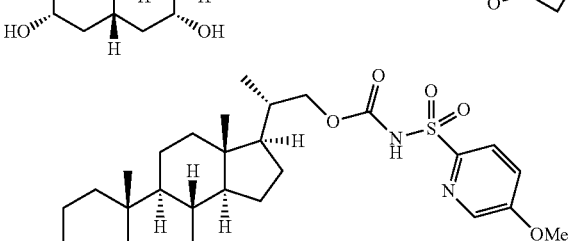
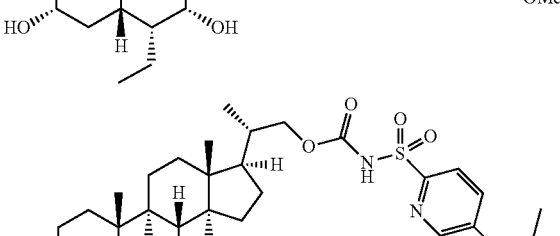
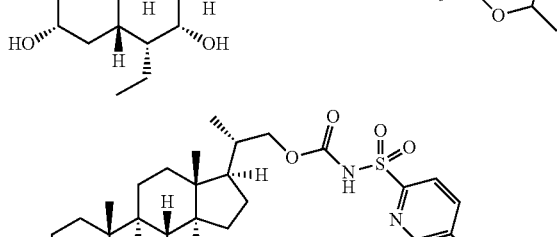

-continued
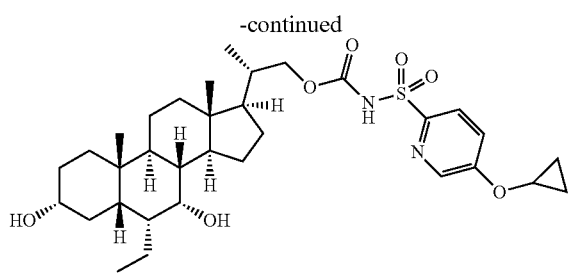
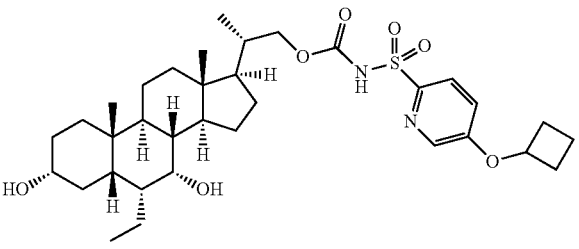
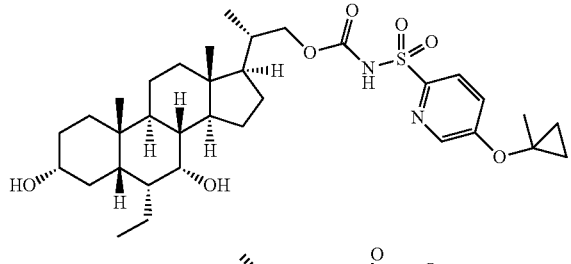
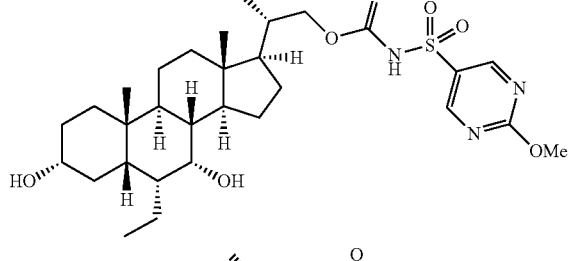
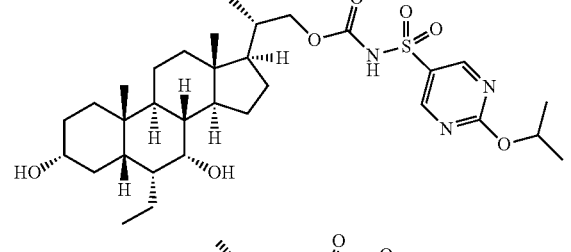
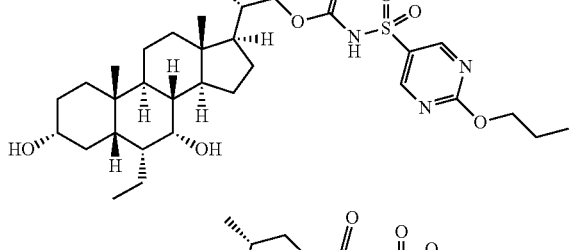
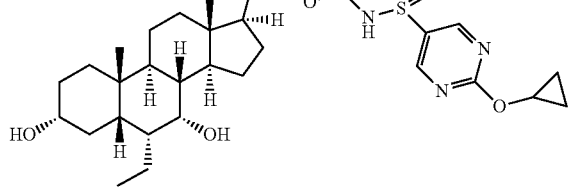
-continued
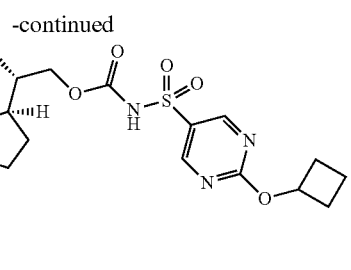
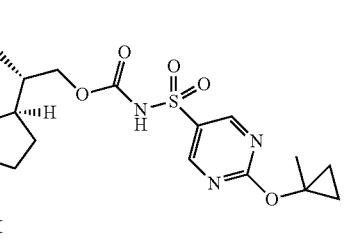
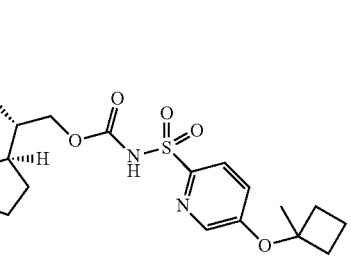
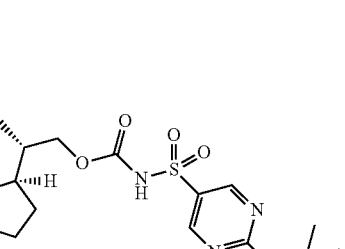
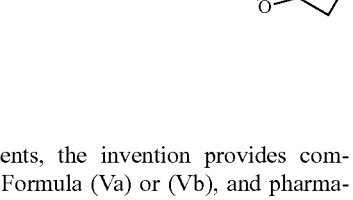
In certain embodiments, the invention provides compounds represented by Formula (Va) or (Vb), and pharmaceutically acceptable salts, esters and prodrugs thereof.

(Va)
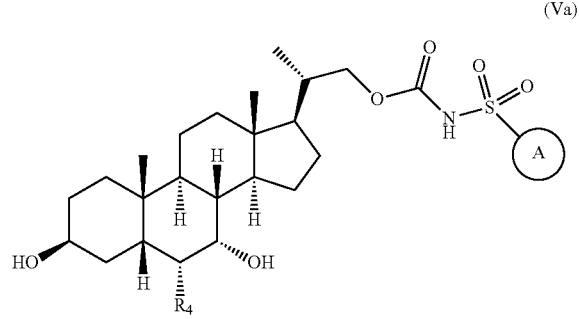
(Vb)
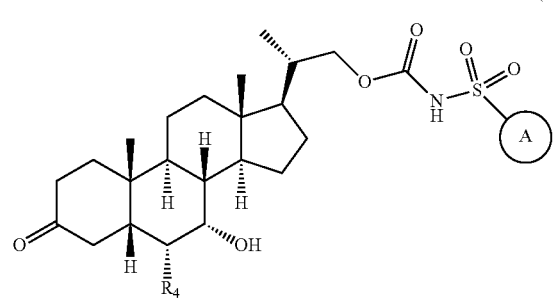
wherein R₄ and
are as previously defined. Preferably R₄ is hydrogen or ethyl.
Representative compounds of the invention include, but are not limited to, the following compounds and pharmaceutically acceptable salts, esters and prodrugs thereof.
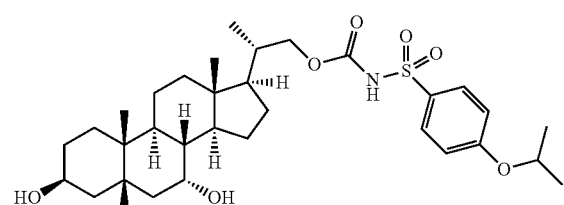
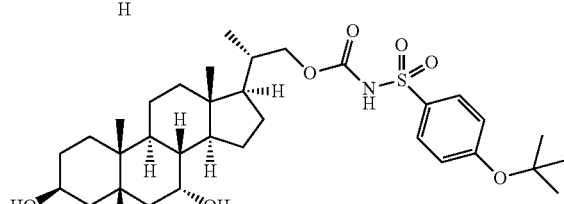
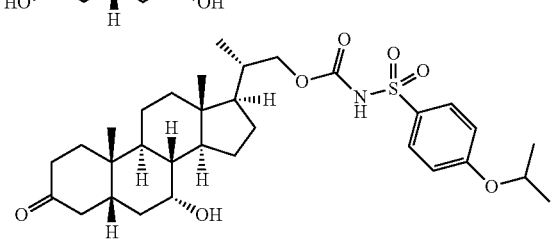
-continued
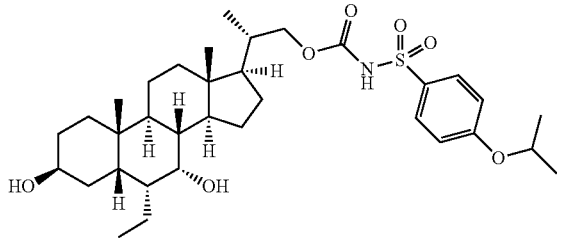
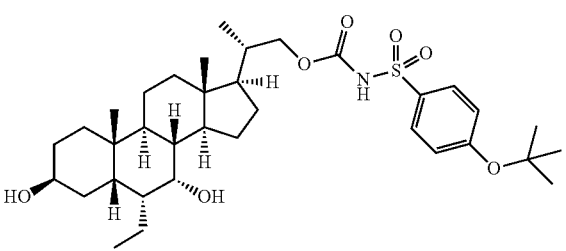
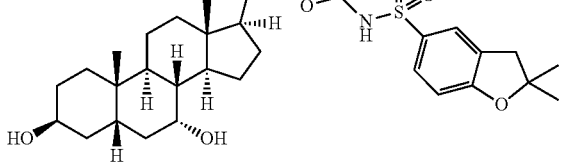
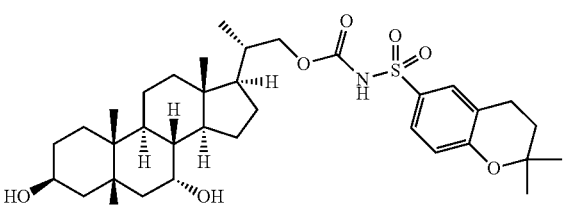
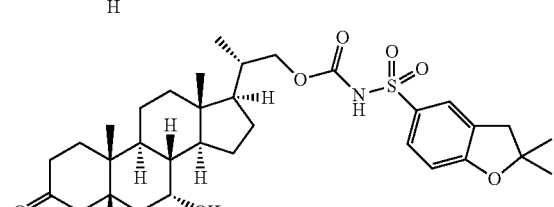
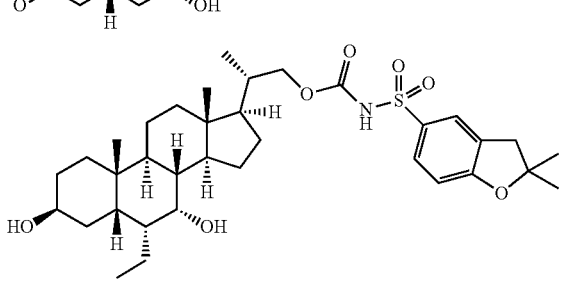

31
-continued
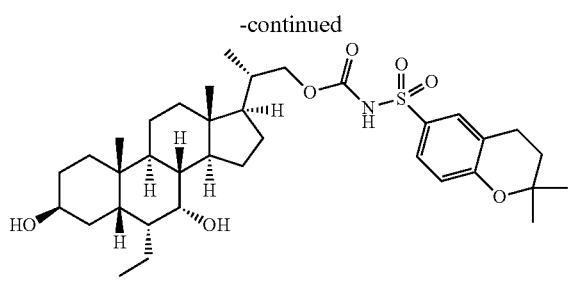
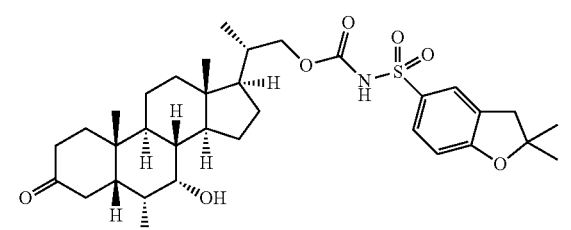
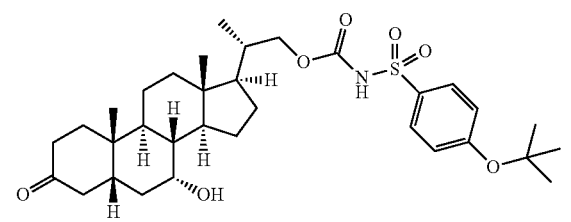
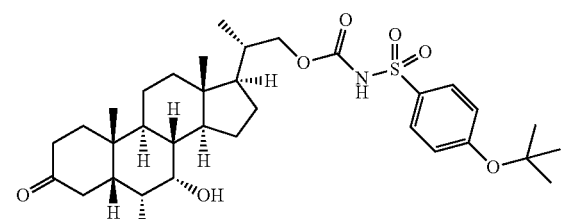
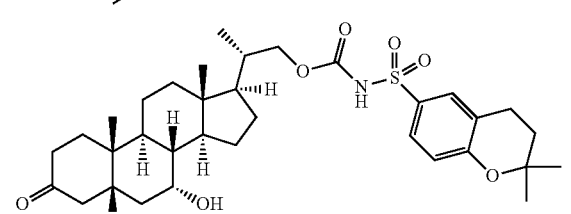
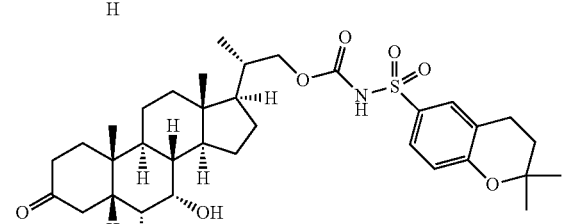
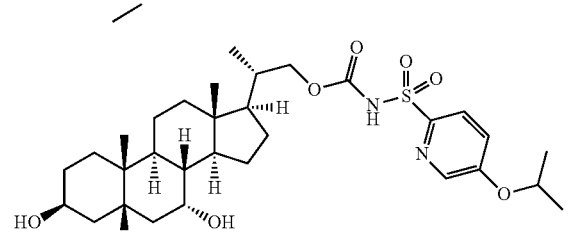
32
-continued
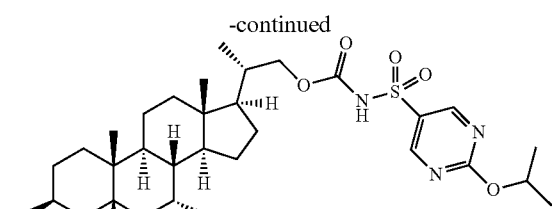
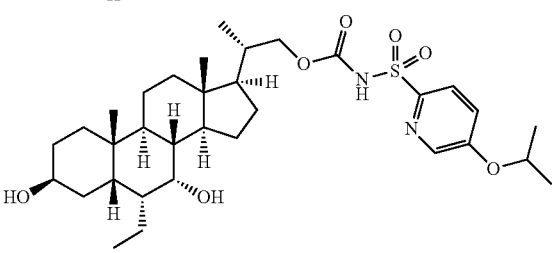
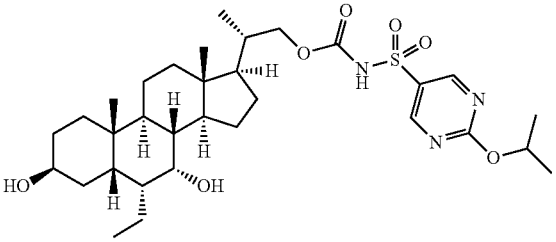
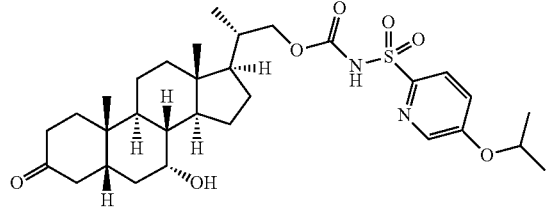
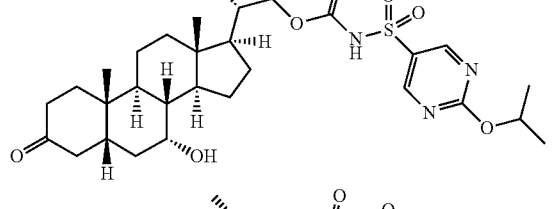
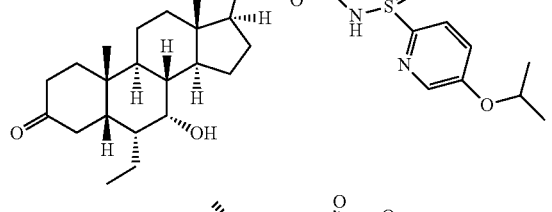
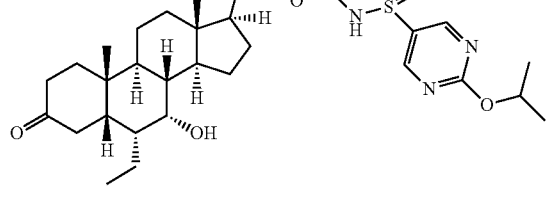
It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention. In certain embodiments, the present invention provides a method for preventing or treating an FXR mediated disease or condition in a subject in need thereof. The method comprises administering to the subject a therapeutically effective amount of a compound of formula (I). The present invention also provides the use of a compound of formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesteremia, hyperlipidemia, chronic liver disease, gastrointestinal disease, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the invention provides for the use, wherein the disease is an inflammatory disease selected from allergy, osteoarthritis, appendicitis, bronchial asthma, pancreatitis, allergic rash, and psoriasis. The invention includes a method of treating or preventing an inflammatory disease selected from allergy, osteoarthritis, appendicitis, bronchial asthma, pancreatitis, allergic rash, and psoriasis.

In one aspect, the invention provides for the use, wherein the disease is an autoimmune disease selected from rheumatoid arthritis, multiple sclerosis, and type I diabetes.

In one aspect, the invention provides for the use, wherein the disease is a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth. The invention includes a method of treating or preventing a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention provides for the use, wherein the disease is cancer selected from colorectal cancer, liver cancer, hepatocellular carcinoma, cholangio carcinoma, renal cancer, gastric cancer, pancreatic cancer, prostate cancer, and insulanoma. The invention includes a method of treating or preventing cancer selected from colorectal cancer, liver cancer, hepatocellular carcinoma, cholangio carcinoma, renal cancer, gastric cancer, pancreatic cancer, prostate cancer, and insulanoma.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_8$ alkyl radicals. Examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_8$ alkynyl groups. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as Z in Formula $I_A$), the carbocycle group can be attached to the two other elements through any two substitutable ring atoms. A $C_4$-$C_6$ carbocycle has 4-6 ring atoms.

The term "cycloalkyl", as used herein, denotes a monovalent group derived from a monocyclic or polycyclic saturated carbocyclic ring compound by the removal of a single hydrogen atom. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but are not limited to, cyclopropyl, cyclobutyl, cyclopentyl, cyclohexyl, bicyclo [2.2.1] heptyl, and bicyclo [2.2.2] octyl.

The term "cycloalkenyl" as used herein, denote a monovalent group derived from a monocyclic or polycyclic carbocyclic ring compound having at least one carbon-carbon double bond by the removal of a single hydrogen atom. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but are not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_{12}$-alkyl, $C_2$-$C_{12}$-alkenyl, $C_2$-$C_{12}$-alkynyl, $C_3$-$C_{12}$-cycloalkyl-halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)— $C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH— $C_1$-$C_{12}$-alkyl, —CONH— $C_2$-$C_{12}$-alkenyl, —CONH— $C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$— $C_1$-$C_{12}$-alkyl, —OCO$_2$— $C_2$-$C_{12}$-alkenyl, —OCO$_2$— $C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH— $C_1$-$C_{12}$-alkyl, —OCONH— $C_2$-$C_{12}$-alkenyl, —OCONH—$C_2$-$C_{12}$-alkynyl, —OCONH— $C_3$-$C_{12}$-cycloalkyl, —OCONH— aryl, —OCONH-heteroaryl, —OCONH-heterocycloalkyl, —NHC(O)— $C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)— heterocycloalkyl, —NHCO$_2$— $C_1$-$C_{12}$-alkyl, —NHCO$_2$— $C_2$-$C_{12}$-alkenyl, —NHCO$_2$— $C_2$-$C_{12}$-alkynyl, —NHCO$_2$— $C_3$-$C_{12}$-cycloalkyl, —NHCO$_2$— aryl, —NHCO$_2$-heteroaryl, —NHCO$_2$-heterocycloalkyl, —NHC(O)NH$_2$, —NHC(O)NH— $C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH— $C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH— $C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH— $C_1$-$C_{12}$-alkyl, —SO$_2$NH— $C_2$-$C_{12}$-alkenyl, —SO$_2$NH— $C_2$-$C_{12}$-alkynyl, —SO$_2$NH— $C_3$-$C_{12}$-cycloalkyl, —SO$_2$NH— aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl, —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The terms "heterocyclic" and "heterocycloalkyl" can be used interchangeably and refer to a non-aromatic ring or a bi- or tri-cyclic group fused, bridge or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible). Examples include, but are not limited to, 3-azabicyclo[3.3.1]nonanyl, 2-oxa-7-azasprio[4.4]nonanyl, and the like.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions and are applicable to provide the formulas herein with proper valency.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The terms "halo" and "halogen," as used herein, refer to an atom selected from fluorine, chlorine, bromine and iodine.

The term "hydrogen" includes hydrogen and deuterium. In addition, the recitation of an atom of an element includes all isotopes of that element so long as the resulting compound is pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus, a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in *J. Pharmaceutical Sciences,* 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dagrees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
ACN for acetonitrile;
BzCl for benzoyl chloride;
CDI for carbonyldiimidazole;
DAST for diethylaminosulfur trifluoride;
DBU for 1, 8-Diazabicycloundec-7-ene;
DCC for N, N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMF for N,N-dimethyl formamide;
DMSO for dimethylsulfoxide;
DSC for N, N'-disuccinimidyl carbonate;
DPPA for diphenylphosphoryl azide;
dppf for 1,1'-Ferrocenediyl-bis(diphenylphosphine)
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
Ph for phenyl;
PMB for p-methoxybenzyl;
TBME for tert-butyl methyl ether;
TEA for triethyl amine;
Tf$_2$O for trifluoromethanesulfonic anhydride;
TFA for trifluoroacetic acid;
THF for tetrahydrofuran;
TLC for thin layer chromatography;
TMSOTf for trimethylsilyl trifluoromethanesulfonate;
TBS for t-Butyldimethylsilyl;
TMS for trimethylsilyl;
TPAP tetrapropylammonium perruthenate;
TPP or PPh$_3$ for triphenylphosphine;
DMTrCl for 4,4'-dimethoxytrityl chloride;
tBOC or Boc for tert-butyloxy carbonyl.

SYNTHETIC METHODS

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

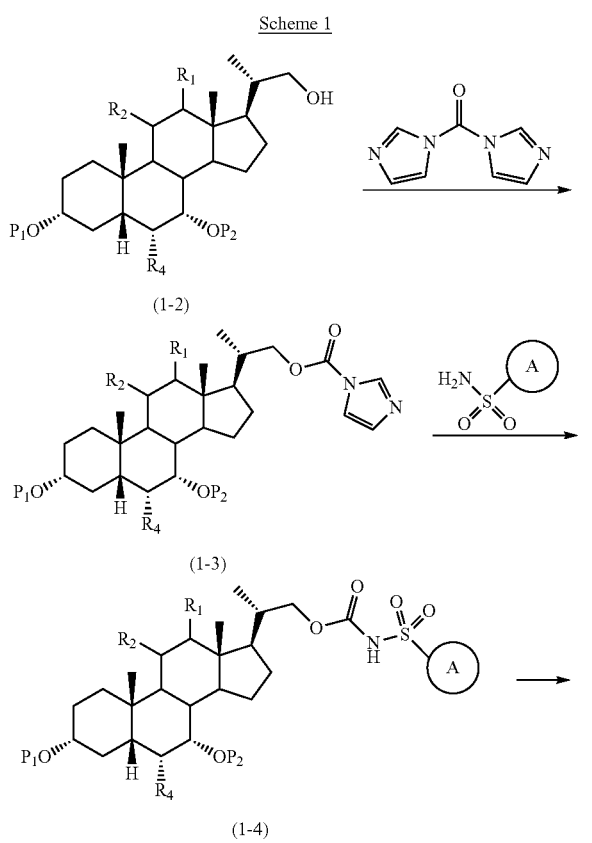

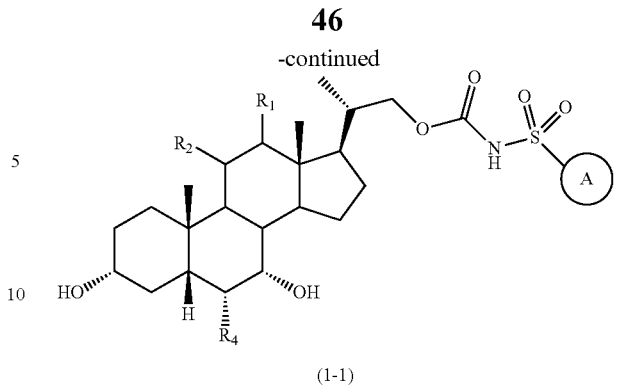

A procedure to prepare compounds of formula (1-1) is illustrated in scheme 1, wherein $R_1$, $R_2$, $R_4$, and

are defined as previously, $P_1$ and $P_2$ are hydroxyl protecting groups. Thus, the compound of formula (1-2) is converted to the compound of formula (1-3) by reacting with CDI in the presence of base such as, but not limited to, $K_2CO_3$, DBU, TEA, DIPEA, and DMAP. Then the compound of formula (1-3) react with sulfonamide

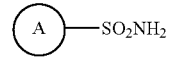

to give the sulfonyl carbamate compounds of formula (1-4). Further deprotection of hydroxyl protecting group $P_1$ and $P_2$ gives the compounds of formula (1-1). A more detailed discussion of the procedures, reagents and conditions for protection and deprotection of hydroxyl protecting groups and amino protecting group are described in literature, for example, by T. W. Greene and P. G. M. Wuts in "*Protective Groups in Organic Synthesis*" $3^{rd}$ ed., John Wiley & Son, Inc., 1999.

Scheme 2

-continued

47

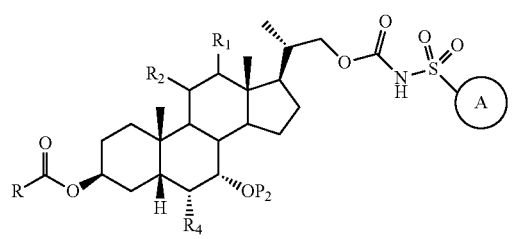

(2-4)

48

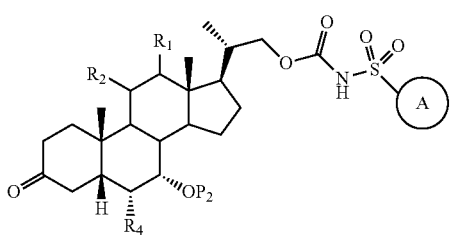

(2-5)

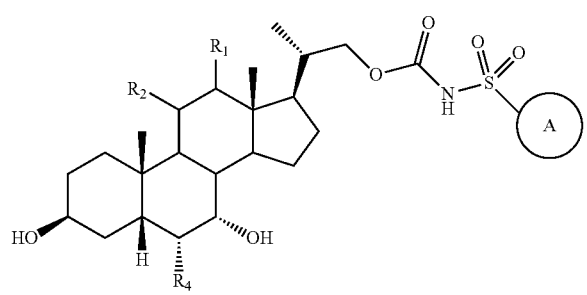

(2-1)

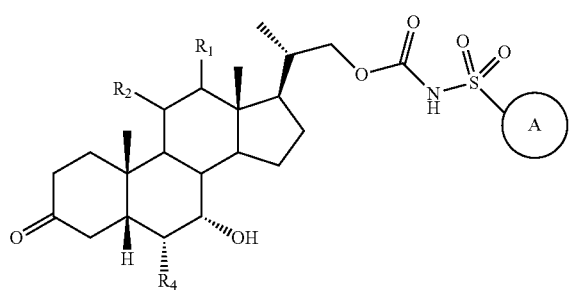

(2-2)

A procedure to prepare compounds of formula (2-1) and (2-2) is illustrated in scheme 2, wherein $R_1$, $R_2$, $R_4$, and (A)

are defined as previously, $P_1$ and $P_2$ are hydroxyl protecting groups. Thus, the compound of formula (1-4) is converted to the compound of formula (2-3) by selective removal of $P_1$.

Treatment of (2-3) with a carboxylic acid RCOOH under Mitsunobu conditions such as, but not limited to, DIAD and $PPh_3$ provides ester compound of formula (2-4) with inversed stereochemistry at C3. Hydrolysis of the ester and deprotection of $P_2$ (if present) give compound of formula (2-1).

In the other aspect, compound of formula (2-3) is converted to a ketone compound of formula (2-5) in the presence of oxidants such as, but not limited to, DMP, PCC, PDC, or $CrO_3$. Further deprecation to remove $P_2$ affords the compound of formula (2-2). A more detailed discussion of the procedures, reagents and conditions for protection and deprotection of hydroxyl protecting groups and amino protecting group are described in literature, for example, by T. W. Greene and P. G. M. Wuts in "*Protective Groups in Organic Synthesis*" $3^{rd}$ ed., John Wiley & Son, Inc., 1999.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

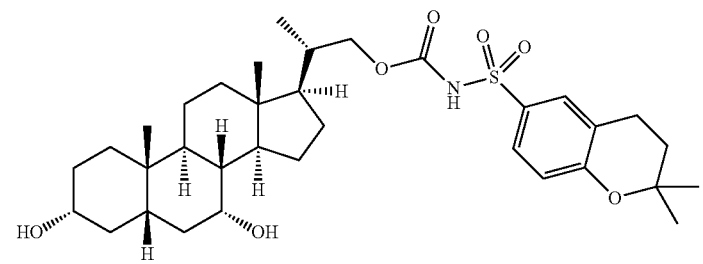

49          -continued          50
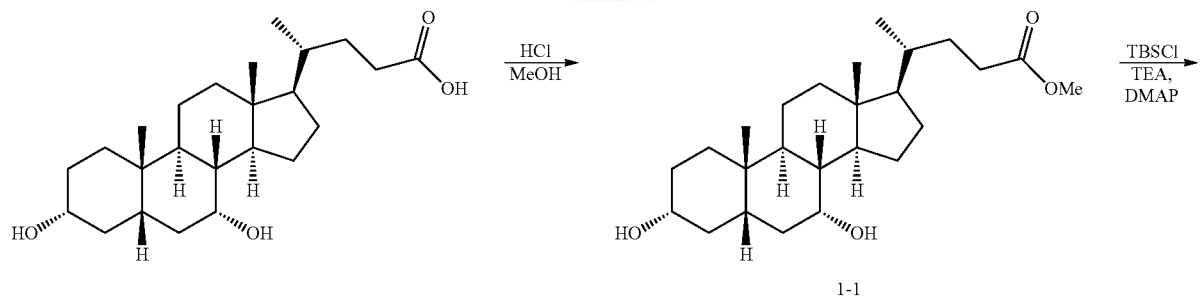
1-1
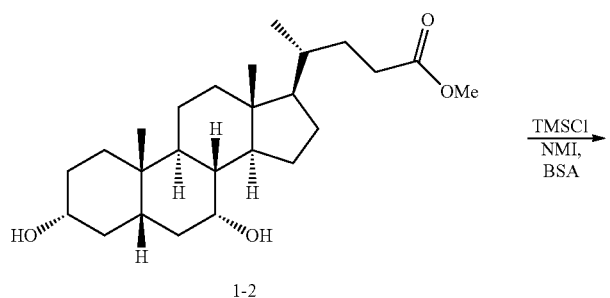
1-2
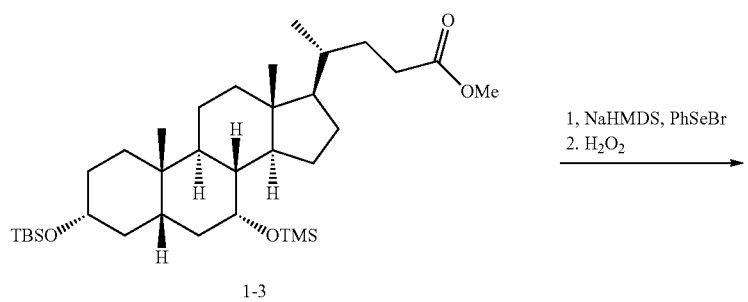
1-3
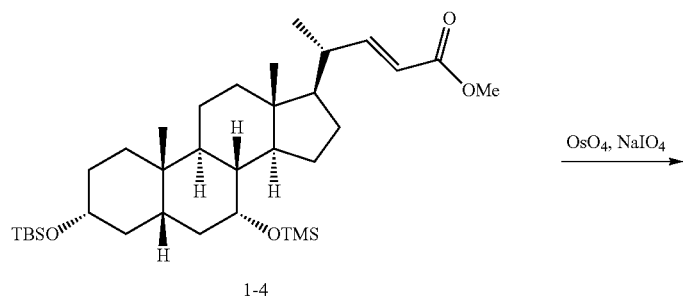
1-4
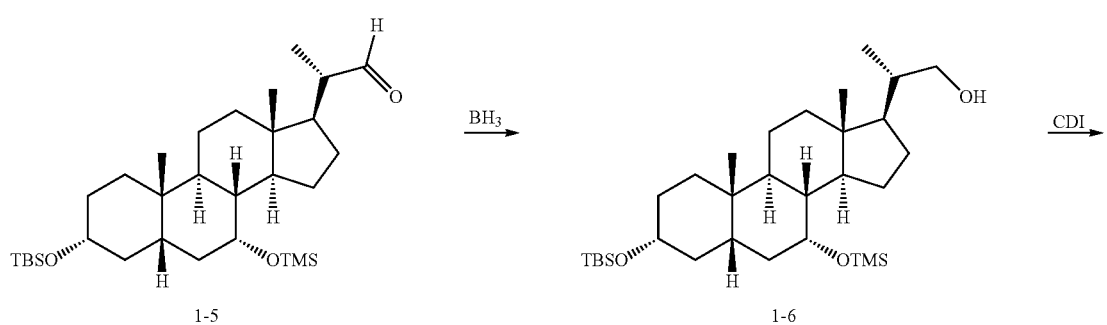
1-5          1-6

-continued

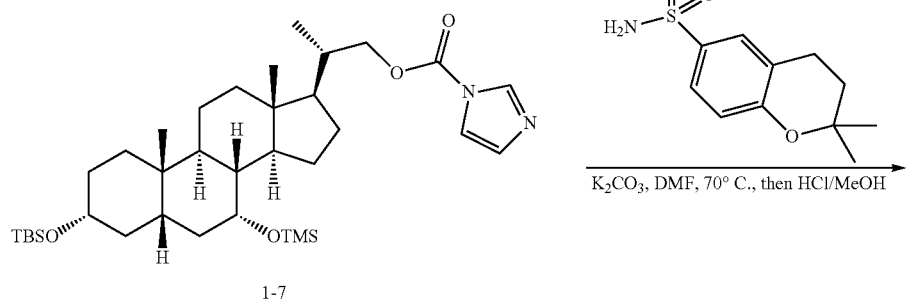

1-7

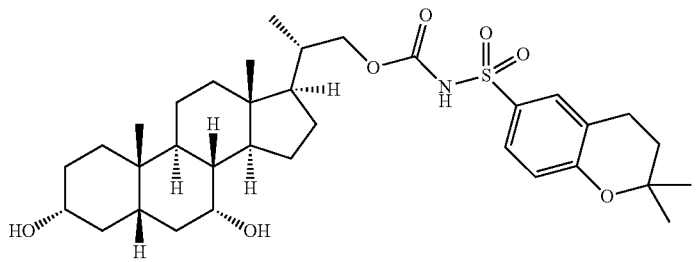

K₂CO₃, DMF, 70° C., then HCl/MeOH

Example 1

Step 1-1:

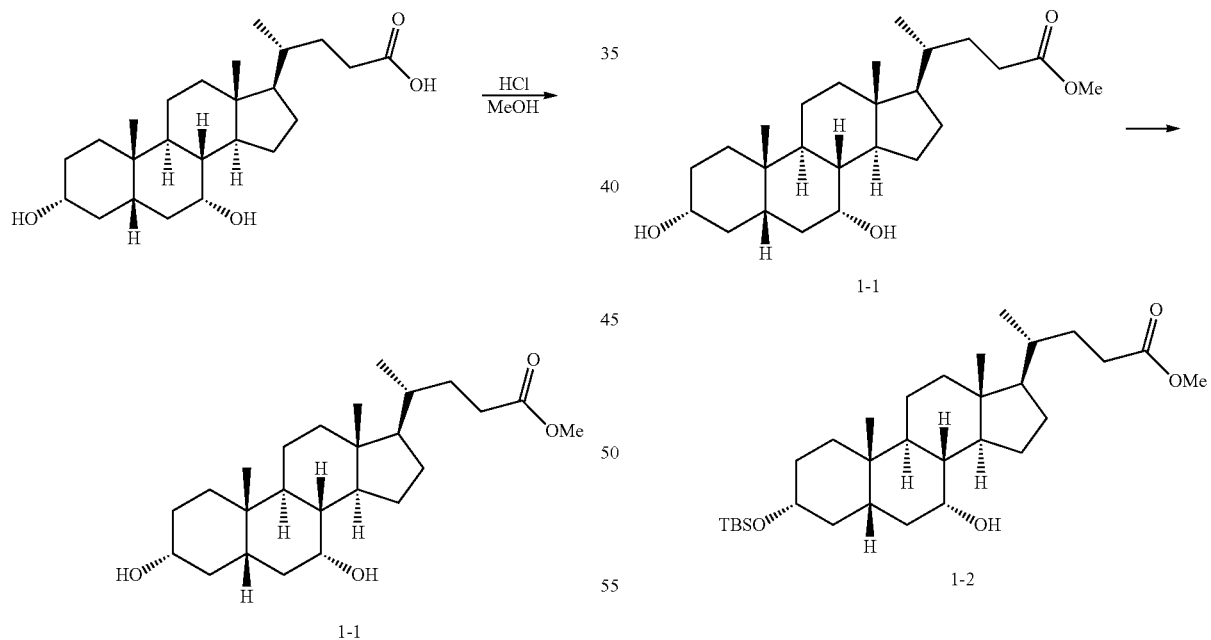

HCl (30 mL, 37%) was added into a solution of chenodeoxycholic acid (50.0 g) in MeOH (300 mL) at 0° C. The solution was stirred at room temperature for 1 h and evaporated to dryness. The residue was diluted with EtOAc (600 mL), washed sequentially with sat. NaHCO₃ (100 mL×2) and sat. NaCl (100 mL×1). The organic layer was dried over Na₂SO₄, filtered, and concentrated to give compound 1-1 (45 g, 87% yield) as a white solid.

Step 1-2:

TBSCl (33 g, 0.22 mol) was added to compound 1-1 (45 g, 0.11 mol), triethylamine (34 g, 0.33 mol), and DMAP (0.7 g, 6 mmol) in DMF (200 mL) at 0° C. The mixture was stirred at room temperature for 3 h. Water (600 mL) was added and the mixture was extracted with EtOAc (300 mL×3). The combined organic phase was washed with sat. NaCl (200 mL×3), dried over Na₂SO₄, filtered, and concentrated. The residue was purified on silica gel with 20 to 40% EtOAc in petroleum ether to give compound 1-2 (50 g, 87% yield) as a yellow solid.

Step 1-3:

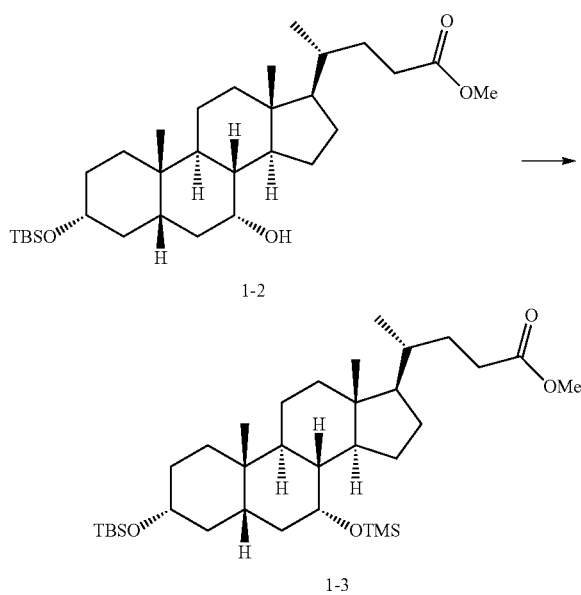

TMSCl (63 g, 0.579 mol) was added to a solution of compound 1-2 (50 g, 0.096 mol), N,O-bis(trimethylsilyl)acetamide (98 g, 0.482 mol), and 1-methylimidazole (39.6 g, 0.482 mol) in DCM (500 mL) at 0° C. The mixture was stirred at room temperature for 3 h. Water (1000 mL) was added and the mixture was extracted with EtOAc (500 mL×3). The combined organic phase was washed with sat. NaCl (500 mL×3), dried over Na$_2$SO$_4$, filtered, and concentrated. The residue was purified on silica gel with 10 to 40% EtOAc in petroleum ether to give compound 1-3 (35 g, 61%) as a yellow solid.

Step 1-4:

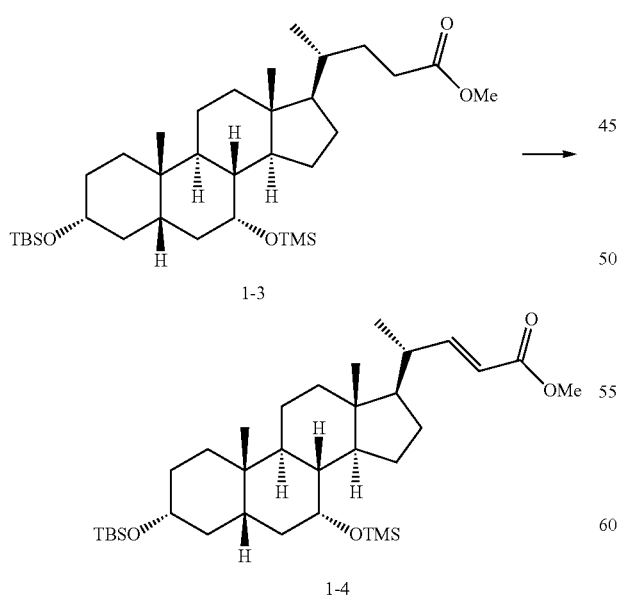

NaHMDS (2.0 M in THF, 67 mL, 134 mmol) was added dropwise to compound 1-3 (35 g, 64 mmol) in THF (200 mL) at −78° C. over 1 h. The mixture was stirred at −78° C. over 1.5 h, and PhSeBr (18 g, 77 mmol) in THF (40 mL) was added dropwise. The mixture was stirred at −78° C. over 2.5 h and at room temperature for 30 min. Sat. NH$_4$Cl (60 mL) was added at 0° C. and the mixture was extracted with EtOAc (200 mL×2). The combined organic phase was washed with sat. NaCl (60 mL×1), dried over Na$_2$SO$_4$, and filtered. To the filtrate was added 30% H$_2$O$_2$ (20 mL) at 0° C. and the mixture was stirred at room temperature over 40 min. The reaction solution was washed sequentially with sat. NaHCO$_3$ (60 mL) and sat. NaCl (60 mL). The organic phase was dried over Na$_2$SO$_4$, filtered and concentrated. The residue was purified on silica gel with 10 to 20% EtOAc in petroleum ether to give compound 1-4 (30 g, 58%) as a yellow oil.

Step 1-4:

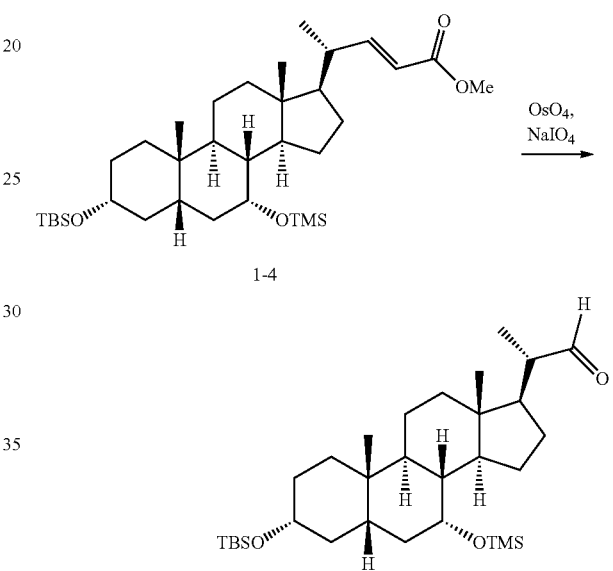

At 0° C. OsO$_4$ (0.5 g, 0.002 mol) was added to a solution of compound 1-4 (10 g, 0.017 mol), 2,6-lutidine (5.49 g, 0.05 mol), and NaIO$_4$ (16 g, 0.075 mol) in 1,4-dioxane (72 mL) and H$_2$O (24 mL). The mixture was stirred at 50° C. overnight. Water (200 mL) was added and the mixture was extracted with DCM (200 mL×3). The combined organic phase was washed with sat. NaCl (100 mL), dried over Na$_2$SO$_4$, filtered, and concentrated to give compound 1-5 (7 g) as a black solid, which was used directly in next step.

Step 1-5:

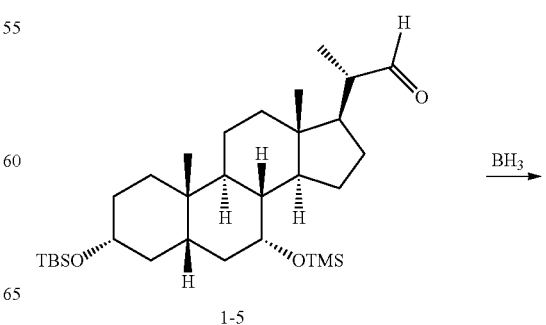

-continued

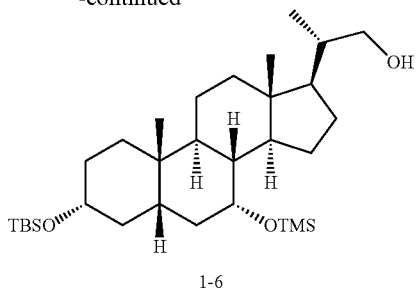
1-6

At 0 OC BH₃ in THF (1M, 100 mL) was added to a solution of compound 1-5 (7 g, crude) in THF (70 mL). The mixture was stirred at room temperature overnight. The reaction was quenched with ice water and extracted with DCM (100 mL×3). The combined organic phase was washed with sat. NaCl (100 mL), dried over Na₂SO₄, filtered, and concentrated to give compound 1-6 (4 g, 44% for 2 steps) as a white solid.

Step 1-6:

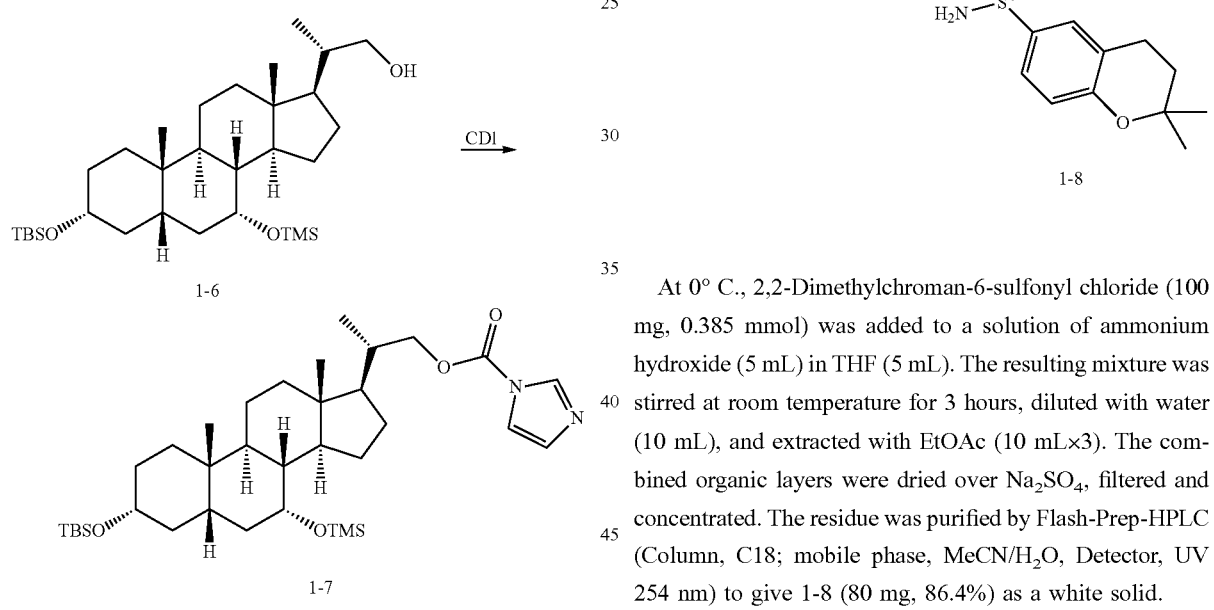

At 0° C. CDI (4 g, 0.0089 mol) was added to a solution of compound 1-6 (4 g, 0.0079 mol) and DIPEA (4 g, 0.0079 mol) in DCM (40 mL). The mixture was stirred at room temperature for 3 h, quenched with water (50 mL), and extracted with DCM (50 mL×3). The combined organic phase was washed with sat. NaCl (50 mL), dried over Na₂SO₄, filtered, and concentrated to give compound 1-7 (2.9 g, 61.7%) as a white solid.

Step 1-7:

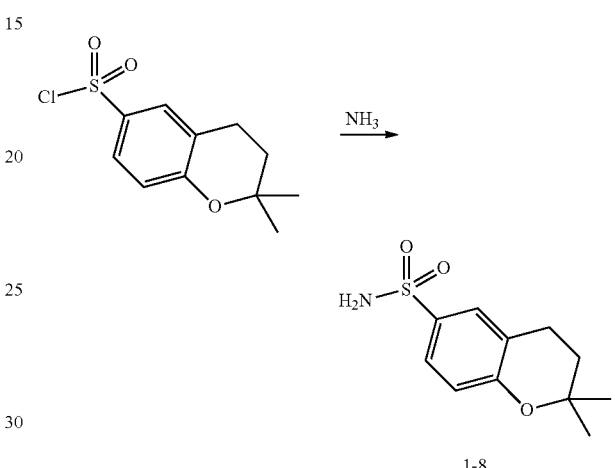
1-8

At 0° C., 2,2-Dimethylchroman-6-sulfonyl chloride (100 mg, 0.385 mmol) was added to a solution of ammonium hydroxide (5 mL) in THF (5 mL). The resulting mixture was stirred at room temperature for 3 hours, diluted with water (10 mL), and extracted with EtOAc (10 mL×3). The combined organic layers were dried over Na₂SO₄, filtered and concentrated. The residue was purified by Flash-Prep-HPLC (Column, C18; mobile phase, MeCN/H₂O, Detector, UV 254 nm) to give 1-8 (80 mg, 86.4%) as a white solid.

Step 1-9:

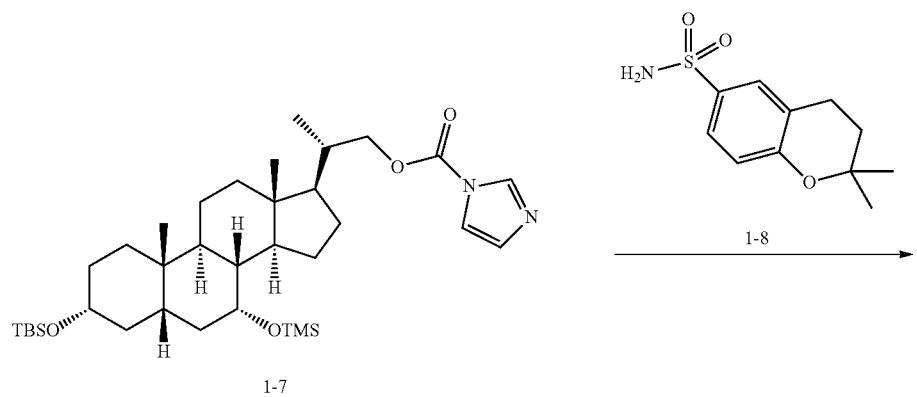

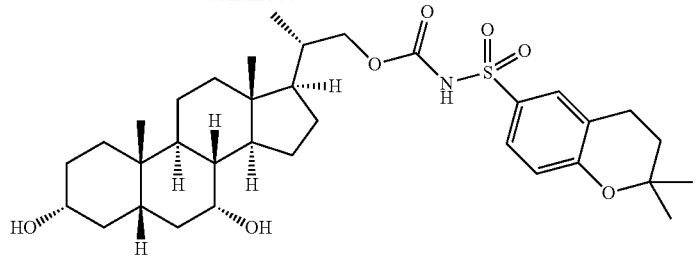

Example 1

Compound 1-7 (70 mg, 0.119 mmol) was added into a mixture of 1-8 (43 mg, 0.179 mmol) and $K_2CO_3$ (50 mg, 0.358 mmol) in THF (2 mL) and the resulting mixture was stirred at 70° C. overnight. After cooling to room temperature, the mixture was diluted with water (10 mL) and extracted with EtOAc (20 mL×3). The combined organic layers were dried over $Na_2SO_4$, filtered and concentrated.

The residue was dissolved in MeOH (5 mL) and HCl (37%, 0.5 mL) was added. The mixture was stirred at room temperature for 1 hour, quenched with saturated $NaHCO_3$ (10 mL), and extracted with EtOAc (20 mL×3). The combined organic layers were dried over $Na_2SO_4$, filtered, and concentrated. The residue was purified by Flash-Prep-HPLC ((IntelFlash-1): Column, C18; mobile phase, $MeCN/H_2O$, Detector, UV 254 nm) to give Example 1 (16.1 mg) as a white solid. ESIMS m/z=616.25 [M-H]$^-$. $^1$H NMR (300 MHz, DMSO, ppm): δ 0.58 (3H, s), 0.83-0.85 (4H, m), 0.91-1.24 (10H, m), 1.26-1.31 (7H, m), 1.36-1.60 (6H, m), 1.63-1.87 (8H, m), 2.07 (2H, s), 2.22 (1H, m), 2.81 (2H, t), 3.62 (1H, m), 3.71 (1H, m), 3.95 (1H, m), 4.12 (1H, d), 4.31 (1H, m), 6.89 (1H, d), 7.56 (1H, dd), 7.62 (1H, d), 11.70 (1H, s).

Examples 2 and 3 in Table 1 were prepared by following procedures similar to that described in Example 1.

TABLE 1

| Example # | Structure | MS data [M − 1]$^-$ |
|---|---|---|
| 2 | 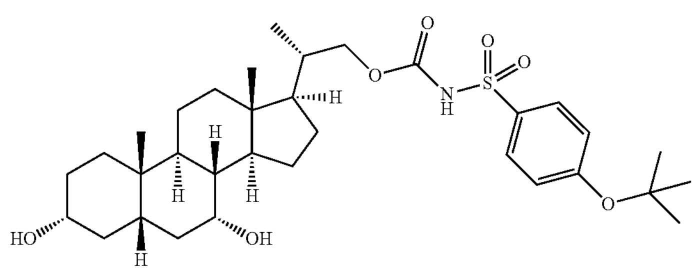 | 604.25 |
| 3 | 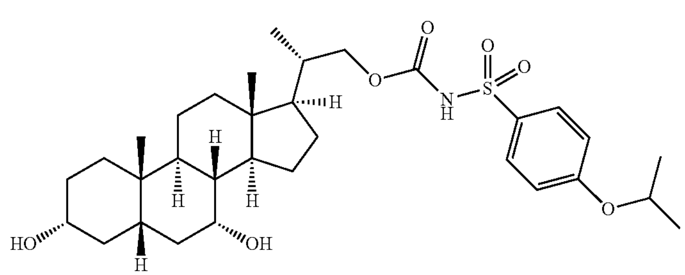 | 590.55 |

Example 4

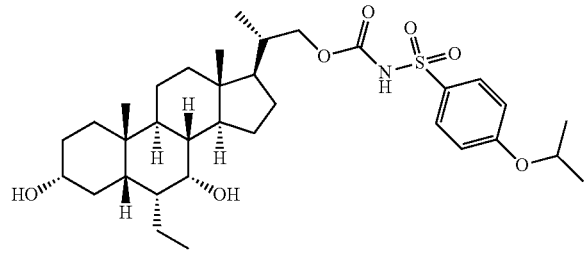

Step 4-1:

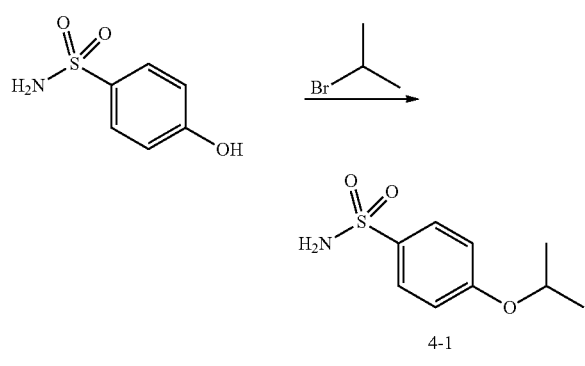

2-Bromopropane (106 mg, 0.87 mmol) was added into a solution of 4-hydroxybenzenesulfonamide (100 mg, 0.58 mmol) in aq. 1N NaOH (1.2 mL) and DMF (5 mL). The mixture was stirred at 50° C. overnight. After cooling to room temperature, the mixture was diluted with EtOAc (10 mL) and washed with brine. The organic layers were dried over $Na_2SO_4$, filtered, and concentrated. The residue was purified by Flash-Prep-HPLC ((IntelFlash-1): Column, C18; mobile phase, $MeCN/H_2O$, Detector, UV 254 nm) to give 4-isopropoxybenzenesulfonamide (4-1) (60 mg, 48%) as a yellow solid.

Step 4-2:

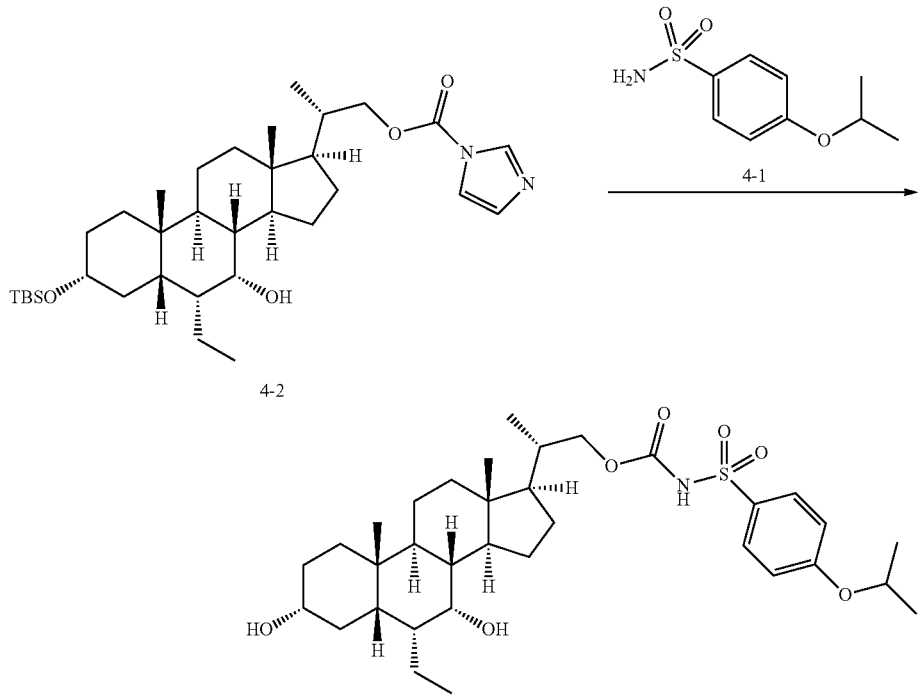

Compound 4-2 (cf. WO 2016161003A1) (70 mg, 0.17 mmol) was added into a mixture of compound 4-1 (42.8 mg, 0.2 mmol) and $K_2CO_3$ (70.6 mg, 0.51 mmol) in DMF (2 mL). The resulting mixture was stirred at 70° C. overnight. After cooling to room temperature, the mixture was diluted with water and extracted with ethyl acetate (20 mL×3). The combined organic layer was dried over $Na_2SO_4$, filtered, and concentrated.

The residue was dissolved in MeOH (2 mL) and HCl (37%, 0.5 mL) was added. The mixture was stirred at room temperature for 1 hour, quenched with saturated $NaHCO_3$ (10 mL), and extracted with EtOAc (20 mL×3). The combined organic layers were dried over $Na_2SO_4$, filtered, and evaporated. The residue was purified by Flash-Prep-HPLC ((IntelFlash-1): Column, $C_{18}$; mobile phase, $MeCN/H_2O$, Detector, UV 254 nm) to give Example 4 (22.4 mg) as a white solid. ESIMS m/z=618.50 [M-H]$^-$. $^1$HNMR (400 MHz, DMSO-$d_6$) δ 11.76 (s, 1H), 7.78 (br d, J=8.0 Hz, 2H), 7.11 (2H, br d, J=8.0 Hz), 4.74 (m, 1H), 4.30 (br s, 1H), 4.04 (d, J=5.1 Hz, 1H), 3.97 (dd, J=10.6, 3.3 Hz, 1H), 3.69 (dd, J=10.6, 7.2 Hz, 1H), 3.48 (br s, 1H), 3.13 (m, 1H), 1.90-1.76 (m, 2H), 1.76-1.61 (m, 4H), 1.61-1.33 (m, 7H), 1.29 (d, J=6.0 Hz, 6H), 1.26-0.90 (m, 9H), 0.90-0.76 (m, 10H), 0.58 (s, 3H).

The below sulfonamides in Table 2 were prepared by following procedures similar to that described in Step 4-1.

TABLE 2

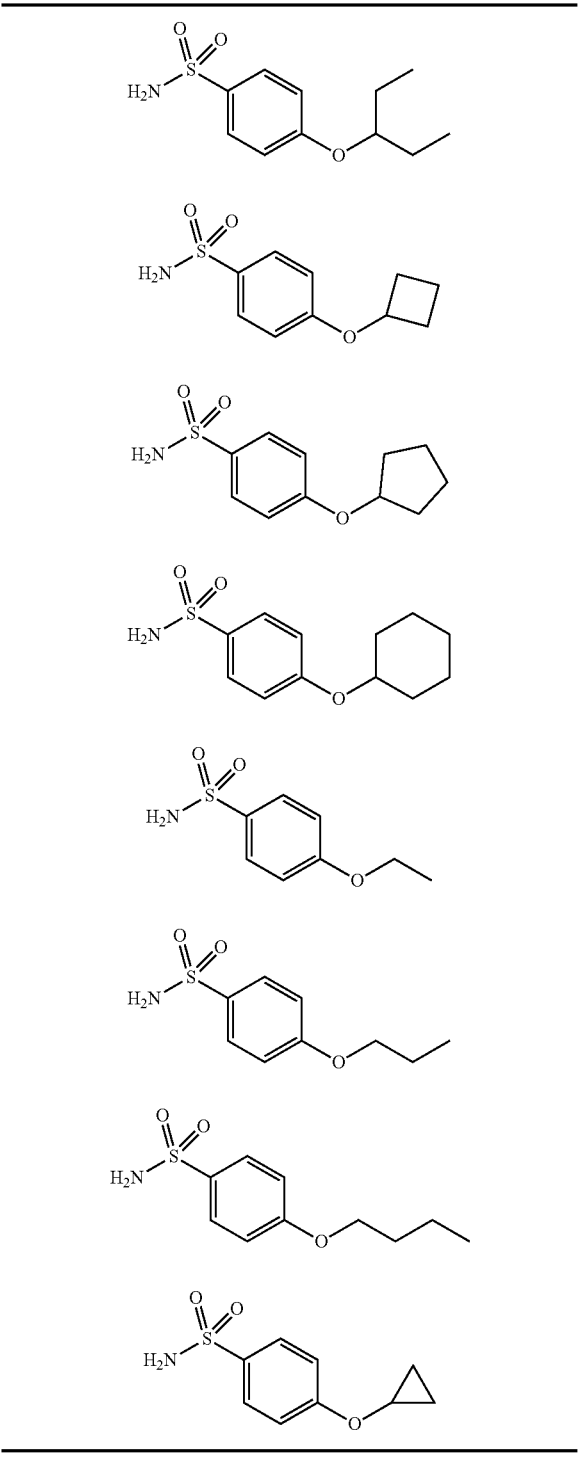

Step 10-1:

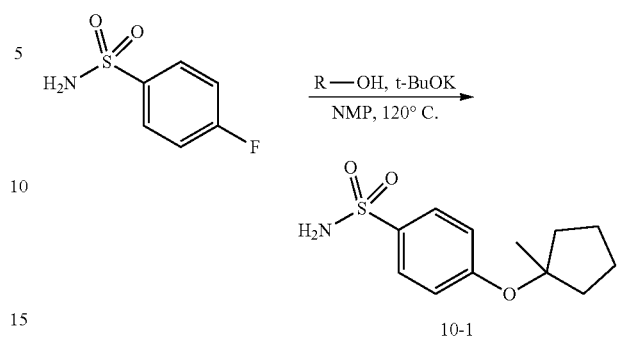

t-BuOK (162 mg, 1.44 mmol) was added into a solution of 4-fluorobenzenesulfonamide (100 mg, 0.73 mmol) and 1-methylcyclopentanol (173 mg, 1.73 mmol) in NMP (3 mL). The resulting mixture was stirred at 120° C. for 1 hour. After cooling to room temperature, the mixture was quenched with water (20 mL) and extracted with EtOAc (20 mL×3). The combined organic layers were dried over $Na_2SO_4$, filtered, and evaporated. The residue was purified by Flash-Prep-HPLC ((IntelFlash-1): Column, C18; mobile phase, MeCN/$H_2O$, Detector, UV 254 nm) to give 10-1 (50 mg, 27%) as a yellow oil.

The below sulfonamides in Table 3 were prepared by following procedures similar to that described in Step 10-1.

TABLE 3

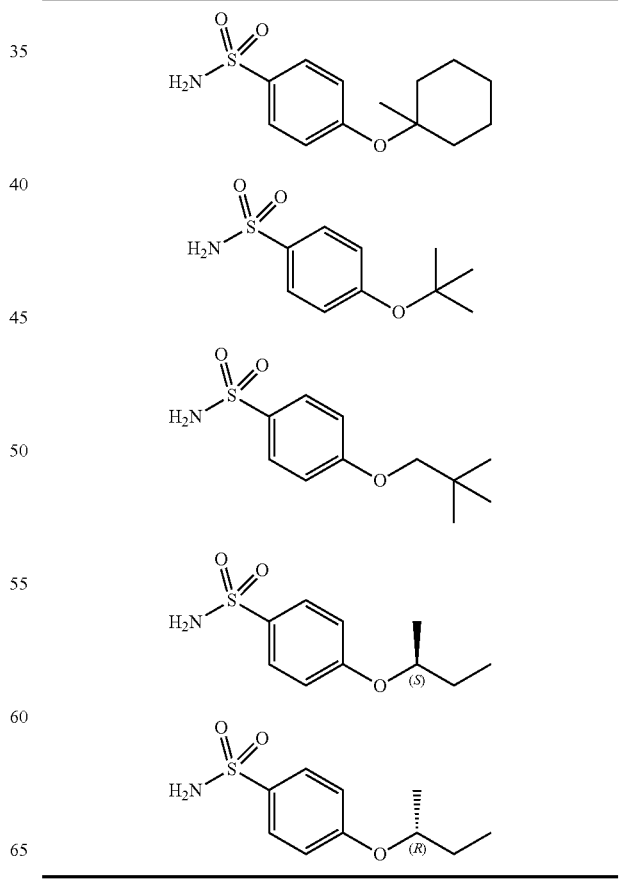

Step 13-1:

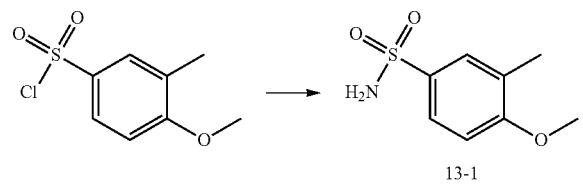

13-1

At 0° C. a solution of 4-Methoxy-3-methylbenzene-1-sulfonyl chloride (1 g, 9.09 mmol) in MeCN (10 mL) was added dropwise to ammonium hydroxide (10 mL). The mixture was warmed to room temperature and stirred for 1 h. Solvent was removed under reduce pressure and the residue was dissolved in EtOAc (30 mL) and washed with brine. The organic layer was dried over $Na_2SO_4$, filtered and concentrated to give the desired compound 13-1 (1.61 g, 88%) as a yellow solid.

Step 13-2:

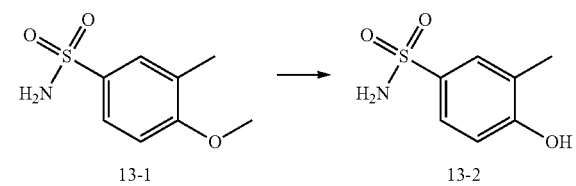

13-1    13-2

At 0° C. $BBr_3$. $Et_2O$ (1N, 12 mL) was added into a solution of compound 13-1 (800 mg, 4 mmol) in DCM (10 mL). The mixture was stirred at 0° C. for 1 h, quenched with ice water, and extracted with EtOAc (100 mL). The organic layer was washed with brine, dried over $Na_2SO_4$, filtered, and concentrated to give compound 13-2 (520 mg, 70%) as a yellow solid.

Step 13-3:

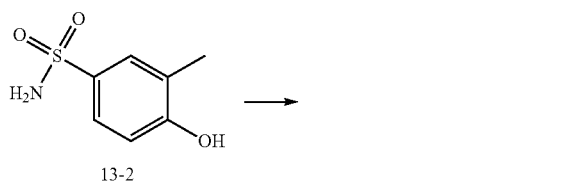

13-2

13-3

2-Bromopropane (195 mg, 1.61 mmol) was added into a solution of compound 13-2 (200 mg, 1.07 mmol) in aq. NaOH (1N, 1.61 mL) in DMF (5 mL). The mixture was stirred at 70° C. overnight. Cooled to room temperature, the mixture was diluted with EtOAc (30 mL) and washed with brine. The organic layer was dried over $Na_2SO_4$, filtered, and concentrated. The residue was purified by Flash-Prep-HPLC ((IntelFlash-1): Column, C18; mobile phase, MeCN/$H_2O$, Detector, UV 254 nm) to give 13-3 (95 mg, 40%) as a yellow solid.

Step 18-1:

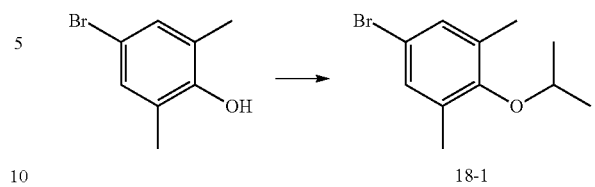

18-1

2-Bromopropane (1.8 g, 14.88 mmol) was added into a solution of 4-bromo-2,6-dimethylphenol (2.0 g, 9.92 mmol) in aq. 1N NaOH (16 mL) in DMF (50 mL). The mixture was stirred at 70° C. overnight and cooled to room temperature. The mixture was diluted with EtOAc (300 mL) and washed with brine. The organic layer was dried over $Na_2SO_4$, filtered, and concentrated. The residue was purified by Flash-Prep-HPLC ((IntelFlash-1): Column, C18; mobile phase, MeCN/$H_2O$, Detector, UV 254 nm) to give compound 18-1 (1.8 g, 75%) as a yellow solid.

Step 18-2:

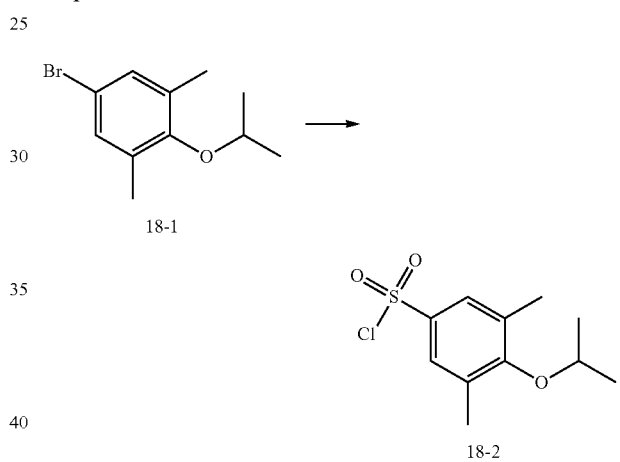

18-1

18-2

At −78° C. to a solution of 5-bromo-2-isopropoxy-1,3-dimethylbenzene 18-1 (1.0 g, 4.1 mmol), and (n-Bu)$_2$Mg (1.3N, 3.8 mL) in dry THF (30 mL) was added n-BuLi (1.6N, 4 mL). After stirring at −78° C. for 2 hours, $SO_2Cl_2$ (4 mL) was added. Stirring was continued for 1 hour below −40° C., and subsequently for another 1 hour at room temperature. The mixture was poured on ice and extracted with diethyl ether (100 mL×3). The combined organic layer was washed with cold water and brine, dried over sodium sulfate, filtered, and concentrated. The residue was used directly without further purification.

Step 18-3:

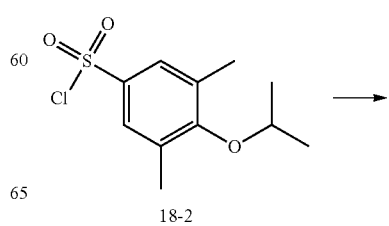

18-2

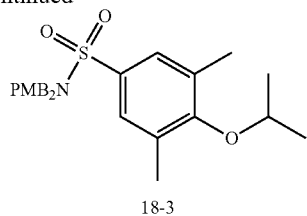

(PMB)₂NH (1.54 g, 6.0 mmol) and Et₃N (4.04 g, 40 mmol) were dissolved in DCM (20 mL). At 0° C., a solution of crude 18-2 in DCM (10 mL) was added and the mixture was stirred at room temperature for 2 hours. The reaction mixture was diluted with DCM (40 mL) and washed with water and saturated brine. The organic layer was dried over Na₂SO₄, filtered, and concentrated. The residue was purified by silica chromatography (petroleum ether/ethyl acetate=2/1), yielding 440 mg (22% for 2 steps) of 4-isopropoxy-N,N-bis(4-methoxybenzyl)-3,5-dimethylbenzenesulfonamide (18-3) as a colorless oil.

Step 18-4:

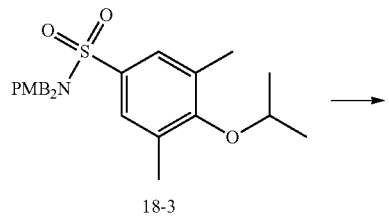

Intermediate 18-3 (440 mg, 0.91 mmol) was dissolved in TFA (5 mL) and the mixture was stirred at 40° C. for 1 hour. Solvent was removed and the residue was dissolved in EtOAc (40 mL) and washed with saturated NaHCO₃ and brine. The organic layer was dried over Na₂SO₄, filtered, and concentrated. The residue was purified by Flash-Prep-HPLC ((IntelFlash-1): Column, C18; mobile phase, MeCN/H₂O, Detector, UV 254 nm) to give 4-isopropoxy-3,5-dimethyl-benzenesulfonamide 18-4 (200 mg, 90%) as a light yellow solid.

Step 22-1:

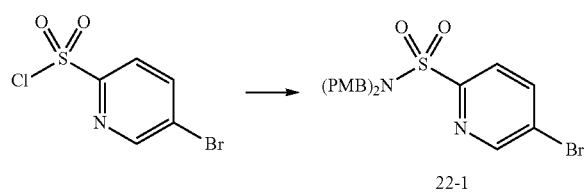

5-Bromopyridine-2-sulfonyl chloride (500 mg, 1.9 mmol) was added into a solution of (PMB)₂NH (732 mg, 2.9 mmol), and Et₃N (0.5 g, 5 mmol) in DCM (5 mL) at 0° C. The mixture was stirred at room temperature for 2 hours. DCM (20 mL) was added and the mixture was washed with water and saturated brine. The organic layer was dried over Na₂SO₄, filtered, and concentrated. The residue was purified on a silica gel column with ethyl acetate/petroleum ether (1:2) to give 700 mg (75%) of 5-bromo-N,N-bis(4-methoxybenzyl)pyridine-2-sulfonamide (22-1) as a colorless oil.

Step 22-2:

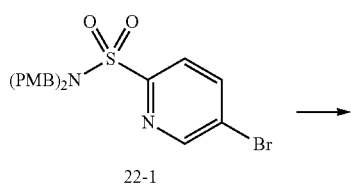

Into a 50 mL round-bottom flask purged and maintained with nitrogen, was added 5-bromo-N,N-bis[(4-methoxyphenyl)methyl]pyridine-2-sulfonamide (22-1) (200 mg, 0.42 mmol), Pd₂(dba)₃ (87 mg, 0.10 mmol), Xphos (80 mg, 0.17 mmol), t-BuONa (121 mg, 1.26 mmol), and toluene (5 mL). The resulting mixture was stirred at 100° C. for 1 h. The solvent was evaporated under vacuum. The residue was purified on a silica gel column with ethyl acetate/petroleum ether (1:2) to give 150 mg (76%) of 5-(tert-butoxy)-N,N-bis[(4-methoxy-phenyl)methyl]pyridine-2-sulfonamide (22-2) as yellow oil.

Step 22-3:

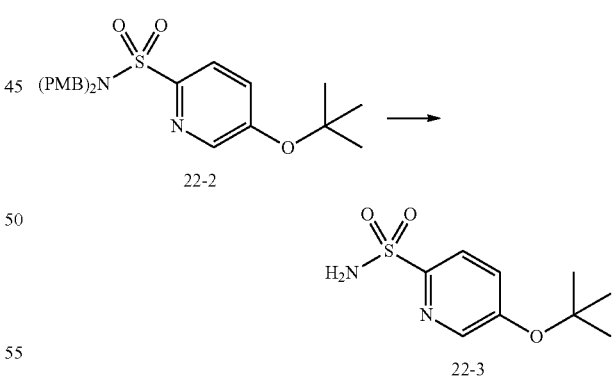

CAN (490 mg, 0.89 mmol) was added into a solution of intermediate 22-2 (150 mg, 0.32 mmol) in CH₃CN (2 mL) and water (2 mL) and the mixture was stirred at room temperature overnight. The reaction solution was diluted with EtOAc (10 mL) and washed with water (5 mL) and brine (5 mL). The organic layer was dried over anhydrous sodium sulfate, filtered, and concentrated to give 50 mg (68%) of 5-(tert-butoxy)-pyridine-2-sulfonamide (22-3) as yellow oil.

67

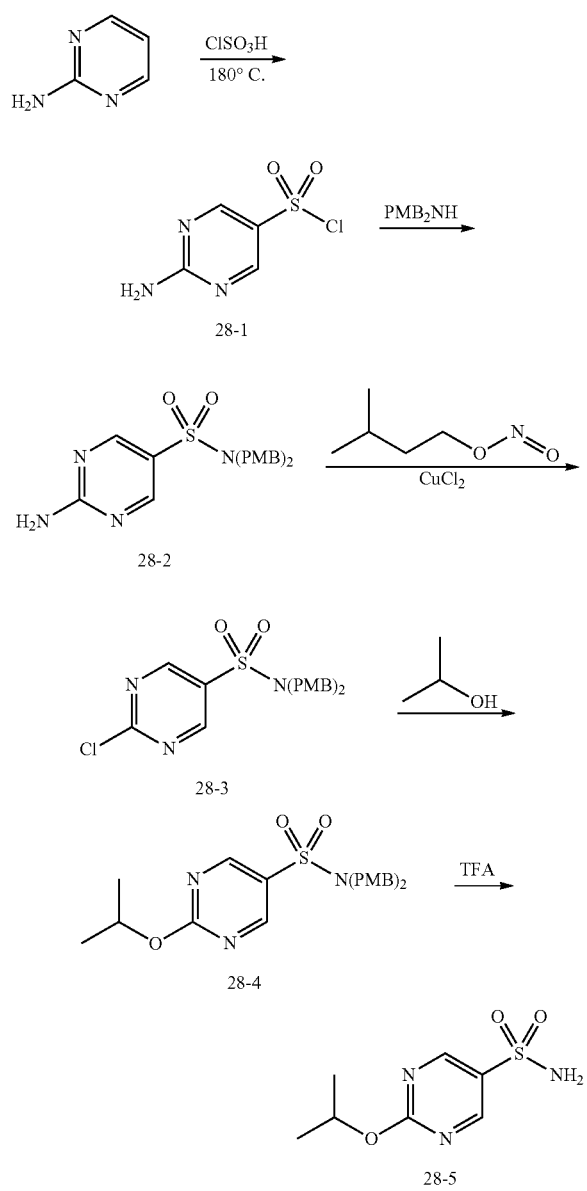

Step 28-1:

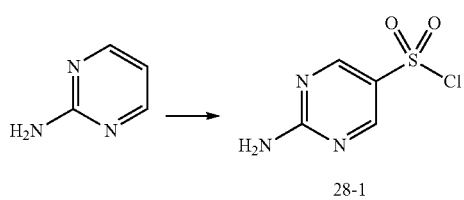 [SMILES: Nc1ncccn1 ; Nc1ncc(S(=O)(=O)Cl)cn1]

Pyrimidin-2-amine (20 g, 0.21 mol) was added slowly to chlorosulfonic acid (100 mL) at 0° C. The mixture was stirred at 180° C. overnight. The mixture was cooled and poured carefully upon crushed ice and extracted by EtOAc (200 mL×3). The combined organic layer was washed with brine, dried over $Na_2SO_4$, filtered, and concentrated to give compound 28-1 (4.7 g, 11.6%) as a yellow solid.

68

Step 28-2:

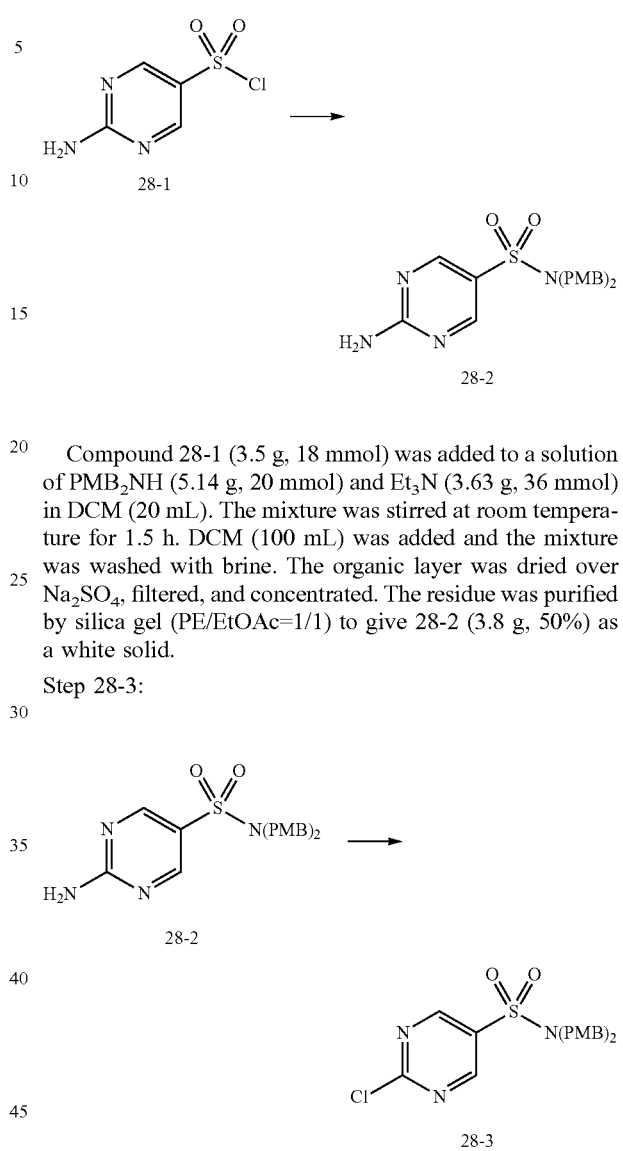

Compound 28-1 (3.5 g, 18 mmol) was added to a solution of $PMB_2NH$ (5.14 g, 20 mmol) and $Et_3N$ (3.63 g, 36 mmol) in DCM (20 mL). The mixture was stirred at room temperature for 1.5 h. DCM (100 mL) was added and the mixture was washed with brine. The organic layer was dried over $Na_2SO_4$, filtered, and concentrated. The residue was purified by silica gel (PE/EtOAc=1/1) to give 28-2 (3.8 g, 50%) as a white solid.

Step 28-3:

Isoamyl nitrite (340 mg, 2.9 mmol) was added into a mixture of 28-2 (400 mg, 0.966 mmol) and $CuCl_2$ (385 mg, 2.9 mmol) in MeCN (10 mL). The resulting mixture was stirred at 50° C. for 2 h. The solvent was removed under reduce pressure. The crude product was purified by silica column (PE/EA=4/1) to give compound 28-3 (180 mg, 42.9%) as a white solid.

Step 28-4:

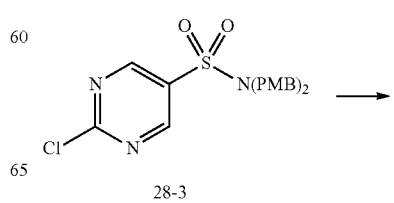

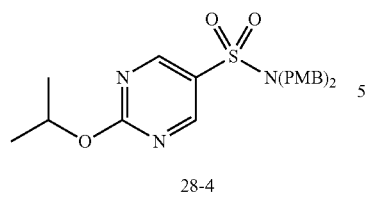

Compound 28-3 (180 mg, 0.41 mmol) was added into a mixture of 2-propanol (2 mL) and K₂CO₃ (171 mg, 1.25 mmol) in THF (4 mL). The resulting mixture was stirred at 50° C. overnight. The solvent was removed under reduce pressure. The residue was purified on silica gel (PE/EA=3/1) to give compound 28-4 (100 mg, 52.6%) as a white solid.

Step 28-5:

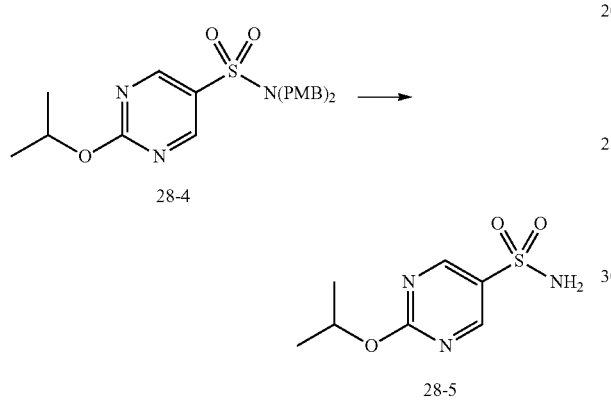

Compound 28-4 (100 mg, 0.21 mmol) was added into TFA (2 mL) and the mixture was stirred at 50° C. for 2 h. The solvent was removed under reduce pressure. The mixture was diluted with EtOAc (500 mL) and washed carefully with saturated NaHCO₃ and brine. The organic layer was dried over Na₂SO₄, filtered, and concentrated. The residue was purified by Flash-Prep-HPLC ((IntelFlash-1): Column, C18; mobile phase, MeCN/H₂O, Detector, UV 254 nm) to give the desired compound 28-5 (30 mg, 66.6%) as a white solid.

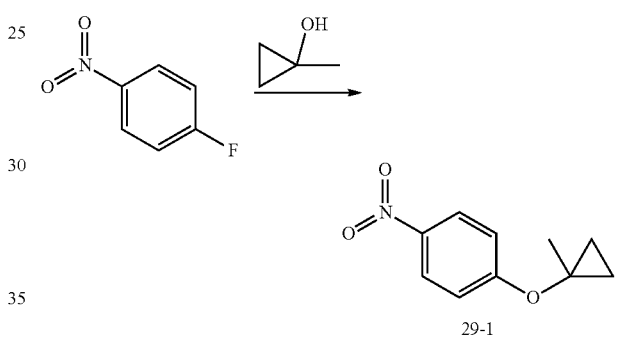

Step 29-1:

Sodium hydride (1.67 g, 69.58 mmol) was added at −40° C. into a mixture of 1-fluoro-4-nitrobenzene (3.92 g, 27.78 mmol) and 1-methylcyclopropan-1-ol (2 g, 27.74 mmol) in N,N-dimethylformamide (30 mL). The resulting solution was stirred at room temperature overnight. The reaction mixture was quenched with cold water and extracted with ethyl acetate (30 mL×3). The combined organic layer was dried over anhydrous sodium sulfate and concentrated under vacuum. The residue was purified by Flash-Prep-HPLC ((IntelFlash-1): Column, C18, mobile phase, MeCN/H₂O, Detector, UV 254 nm) to give 2.9 g (54%) of 1-(1-methyl-cyclopropoxy)-4-nitrobenzene (29-1) as brown oil.

Step 29-2:

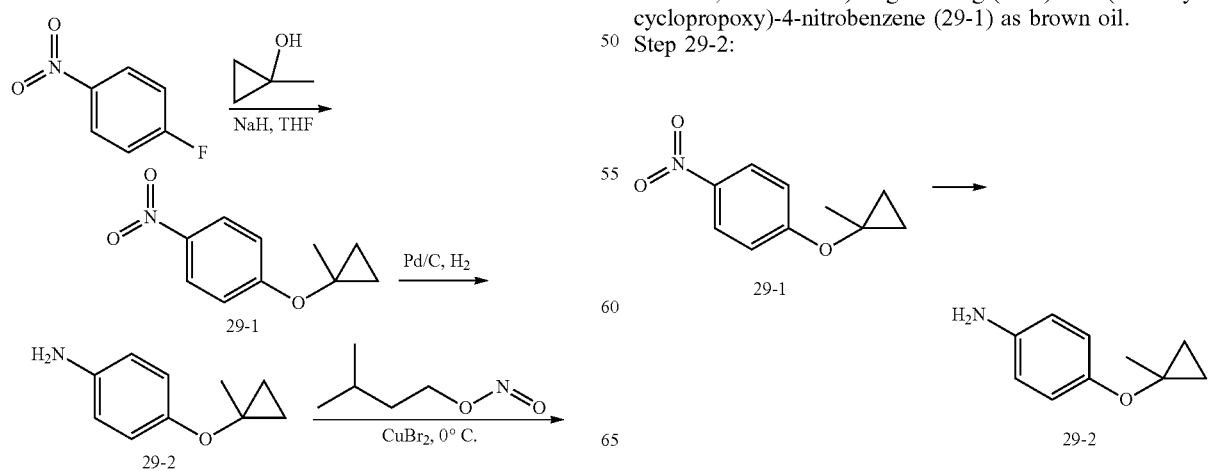

To a solution of 1-(1-methylcyclopropoxy)-4-nitrobenzene 29-1 (2.9 g, 15.01 mmol) in methanol (50 mL) was added Pd—C(10%, 1 g) under N₂. The suspension was degassed under vacuum and purged with H₂ several times. The mixture was stirred under an atmosphere of H₂ at room temperature for 1 h. The mixture was filtered and the filtrate was concentrated under vacuum. The crude product was purified by Flash-Prep-HPLC ((IntelFlash-1): Column, C18; mobile phase, MeCN/H₂O, Detector, UV 254 nm) to give 2 g (82%) of 4-(1-methylcyclopropoxy) aniline (29-2) as brown oil.

Step 29-3:

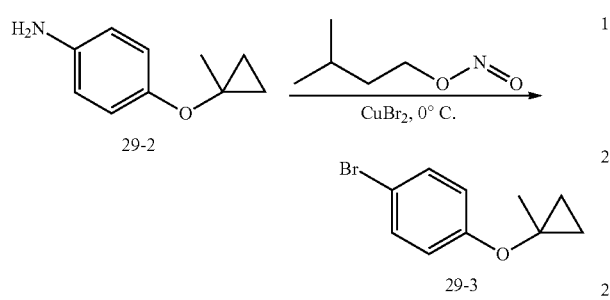

4-(1-Methylcyclopropoxy) aniline 29-2 (1 g, 9.00 mmol) in CH₃CN (5 mL) was added dropwise at 0° C. to a mixture of 3-methylbutyl-nitrite (1.78 g, 15.19 mmol), and CuBr₂ (1.37 g) in CH₃CN (20 mL). The resulting solution was stirred at room temperature for 2 h. The mixture was poured into a cold solution of sodium bicarbonate and extracted with ethyl acetate (20 mL×3). The combined organic layers were dried over anhydrous sodium sulfate and concentrated under vacuum. The crude product was purified by Flash-Prep-HPLC ((IntelFlash-1): Column, C₁₈; mobile phase, MeCN/H₂O, Detector, UV 254 nm) to give 300 mg (19%) of 1-bromo-4-(1-methylcyclopropoxy) benzene (29-3) as brown oil.

Step 29-4:

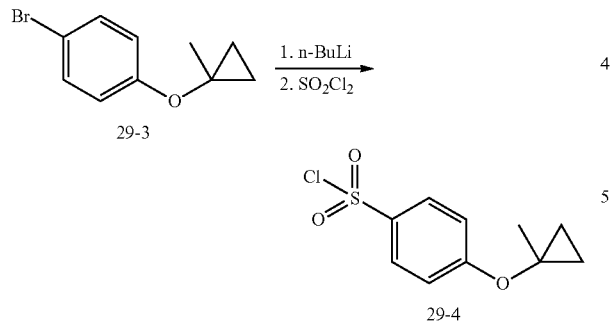

To a solution of 1-bromo-4-(1-methylcyclopropoxy) benzene 29-3 (300 mg, 1.3 mmol) and (n-Bu)₂Mg (1.3N, 1.2 mL) in dry THF (5 mL) at −78° C. was added n-BuLi (1.6N, 1.2 mL). After stirring at −78° C. for 2 hours, SO₂Cl₂ (1.3 mL) was added. Stirring was continued for 1 hour below −40° C., and subsequently for another 1 hour at room temperature. The mixture was poured on ice and extracted with diethyl ether (20 mL×3). The organic layer was washed with cold water and brine, dried over sodium sulfate, filtered, and concentrated. The residue was used directly without further purification.

Step 29-5:

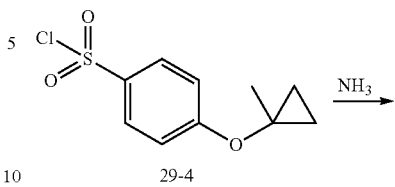

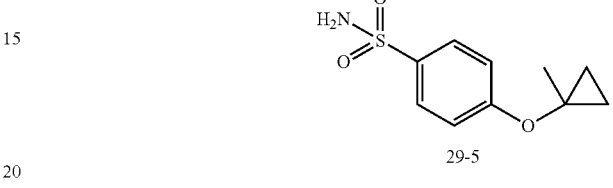

Ammonium hydroxide (2 mL) was added into a solution of 29-4 in MeOH (5 mL) at 0° C. The mixture was stirred at room temperature for 2 hours. The solvent was evaporated under reduced pressure. The residue obtained was purified by silica chromatography (petroleum ether/ethyl acetate 2/1) yielding 60 mg (27% for 2 steps) of 4-(1-methylcyclopropoxy) benzene-sulfonamide (29-5) as a light yellow solid.

Step 30-1:

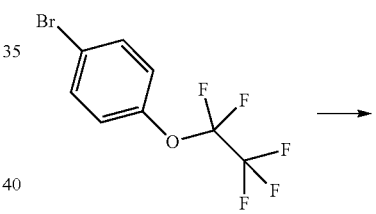

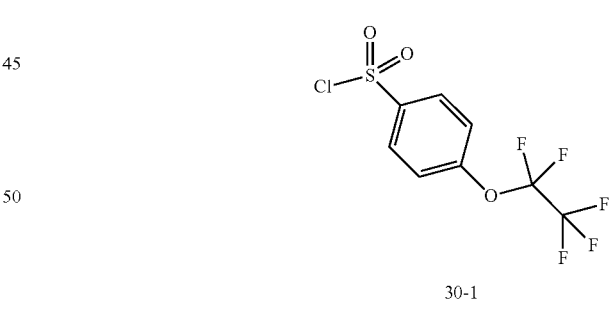

To a solution of 1-bromo-4-(perfluoroethoxy) benzene (300 mg, 1.03 mmol) and (n-Bu)₂Mg (1.3N, 1 mL) in dry THF (5 mL) at −78° C. was added n-BuLi (1.6N, 1 mL) dropwise. After stirring at −78° C. for 2 hours, SO₂Cl₂ (1 mL) was added. Stirring was continued for 1 hour below −40° C., and subsequently for another 1 hour at room temperature. The mixture was poured on ice and extracted with diethyl ether (20 mL×3). The organic layer was washed with cold water and brine, dried over sodium sulfate, filtered, and concentrated. The residue was used directly without further purification.

Step 30-2:

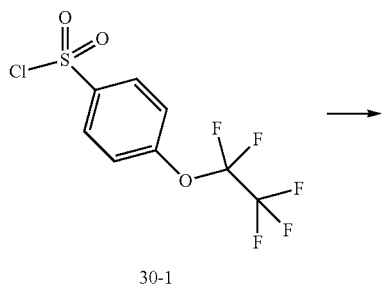

Step 30-3:

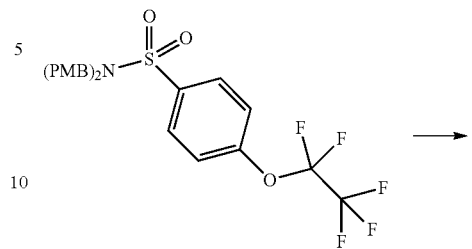

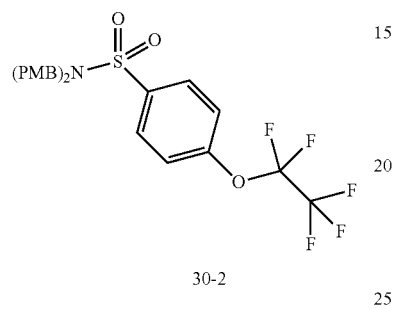

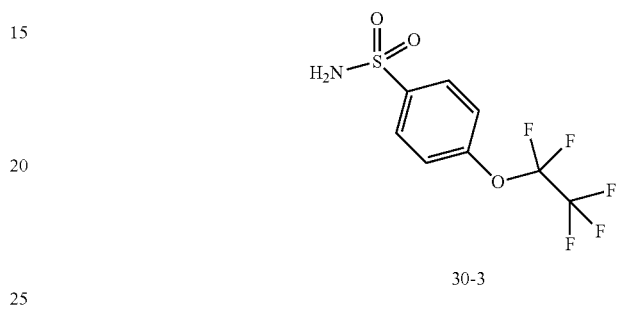

(PMB)₂NH (386 mg, 1.5 mmol) and Et₃N (1.01 g, 10 mmol) was dissolved in DCM (5 mL). At 0° C. a solution of crude 30-1 in DCM (3 mL) was added and the mixture was stirred at room temperature for 2 hours. DCM (10 mL) was added and the mixture was washed with water and saturated brine. The organic layer was dried over Na₂SO₄, filtered, and evaporated. The residue was purified by silica gel chromatography (petroleum ether/ethyl acetate 2/1) yielding 140 mg (26% for 2 steps) of 4-(tetrahydropyran-4-yloxy)-benzenesulfonyl chloride (30-2) as a colorless oil.

Intermediate 30-2 (140 mg, 0.26 mmol) was dissolved in TFA (2 mL) and the mixture was stirred at 40° C. for 1 hour. The solvent was removed and the residue was dissolved in EtOAc (10 mL), washed with saturated NaHCO₃ and brine. The organic layer was dried over Na₂SO₄, filtered, and concentrated. The residue was purified by Flash-Prep-HPLC ((IntelFlash-1): Column, C18; mobile phase, MeCN/H₂O, Detector, UV 254 nm) to give 4-(perfluoroethoxy) benzenesulfonamide 30-3 (60 mg, 78%) as a light yellow solid.

The below examples 5-30 in Table 4 were prepared by following procedures similar to that described in Step 4-2.

TABLE 4

| Example # | Structure | MS data [M − 1]⁻ |
|---|---|---|
| 5 | 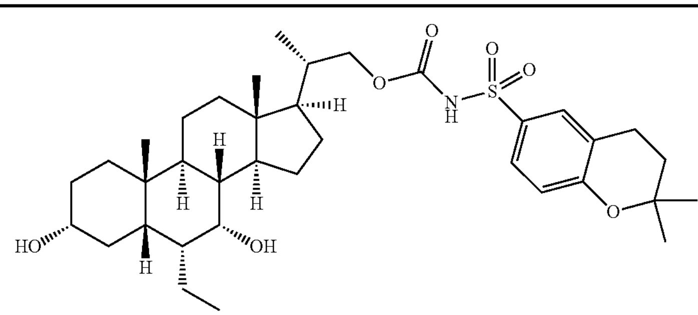 | 644.55 |
| 6 | 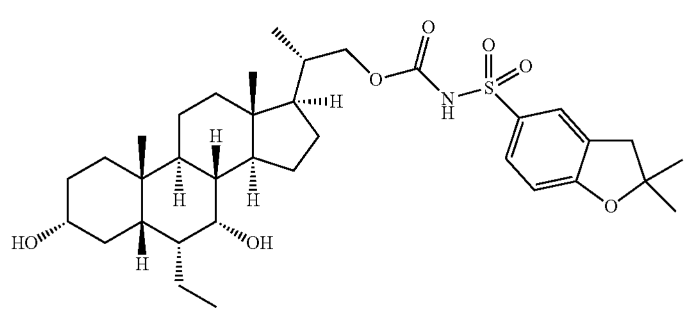 | 630.60 |

TABLE 4-continued

| Example # | Structure | MS data [M − 1]⁻ |
|---|---|---|
| 7 | 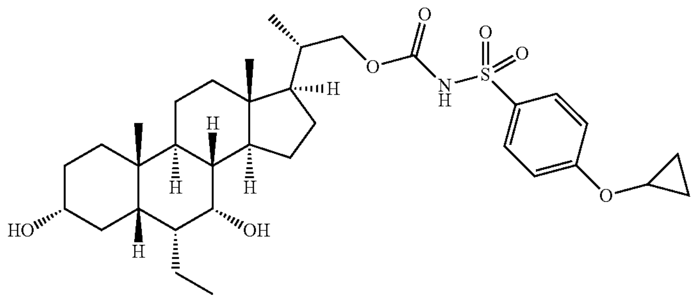 | 616.50 |
| 8 | 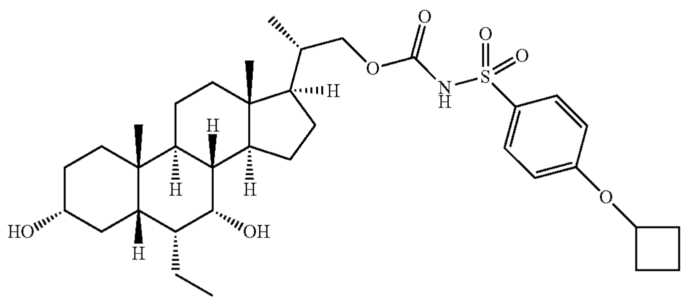 | 630.55 |
| 9 | 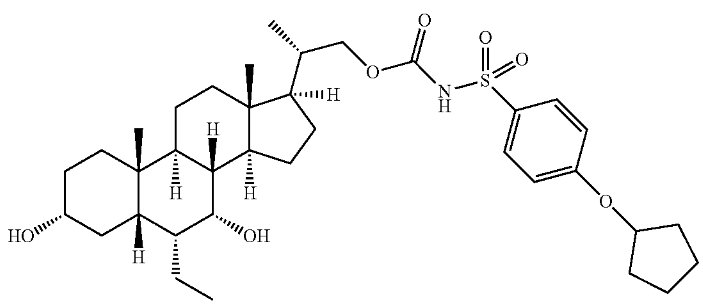 | 644.55 |
| 10 | 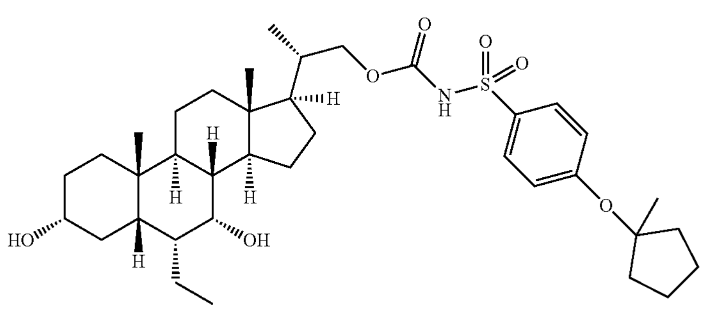 | 658.55 |
| 11 | 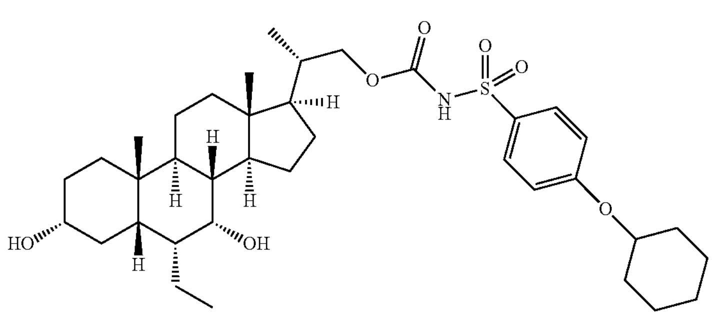 | 658.60 |

TABLE 4-continued

| Example # | Structure | MS data [M − 1]⁻ |
|---|---|---|
| 12 | 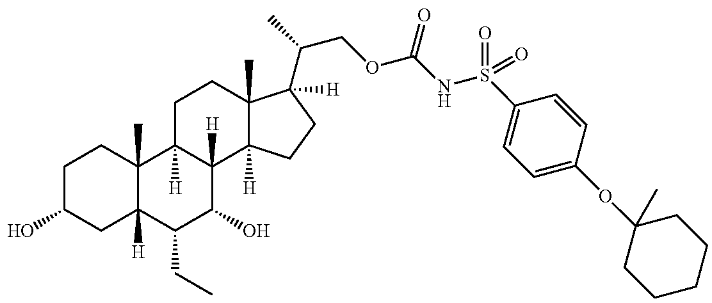 | 672.60 |
| 13 | 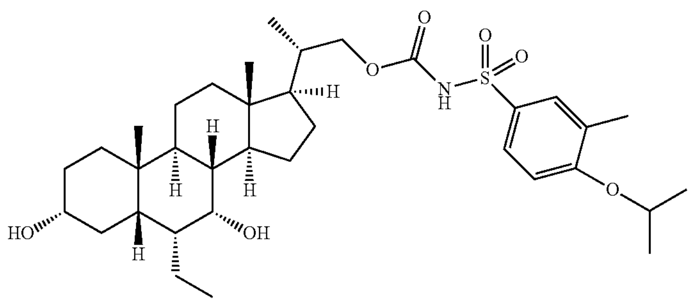 | 632.55 |
| 14 | 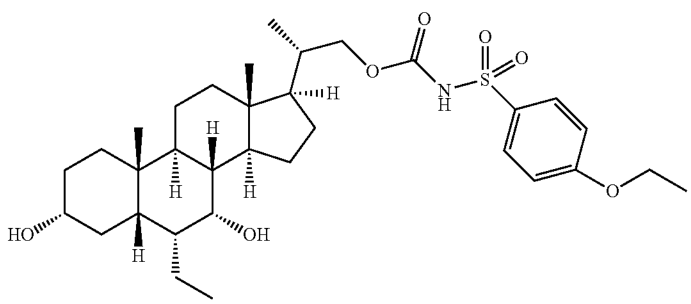 | 604.10 |
| 15 | 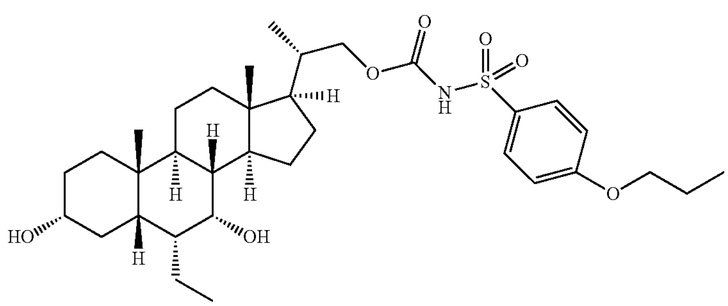 | 618.10 |
| 16 | 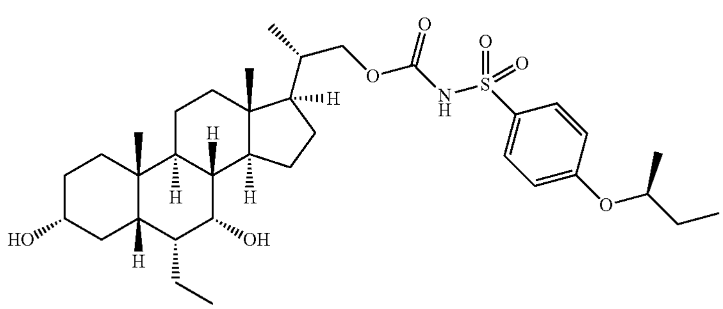 | 632.15 |

TABLE 4-continued

| Example # | Structure | MS data [M − 1]⁻ |
|---|---|---|
| 17 | 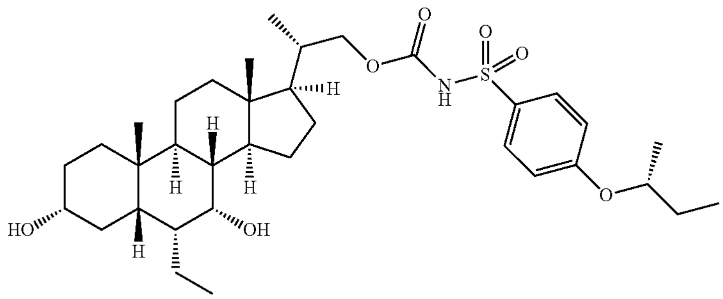 | 632.25 |
| 18 | 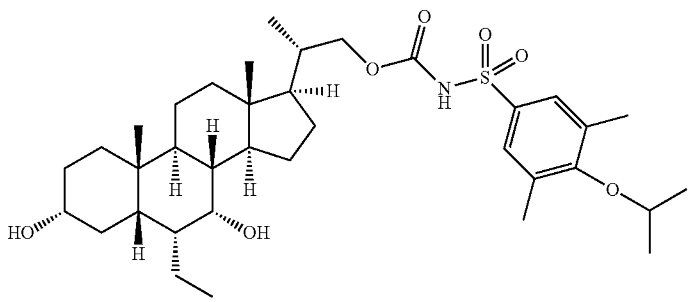 | 646.15 |
| 19 | 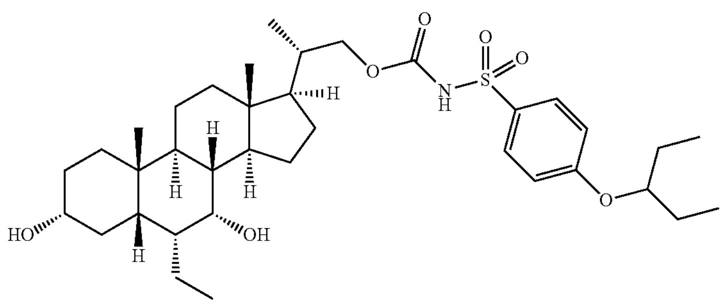 | 646.60 |
| 20 | 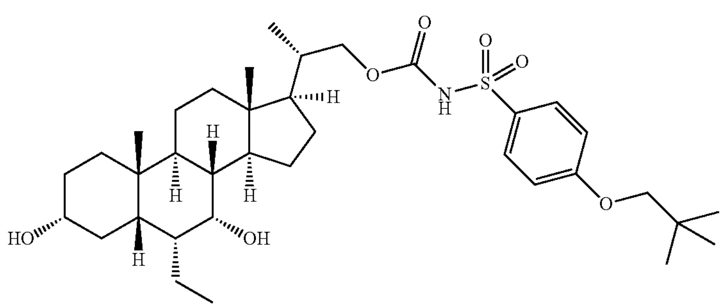 | 646.55 |
| 21 | 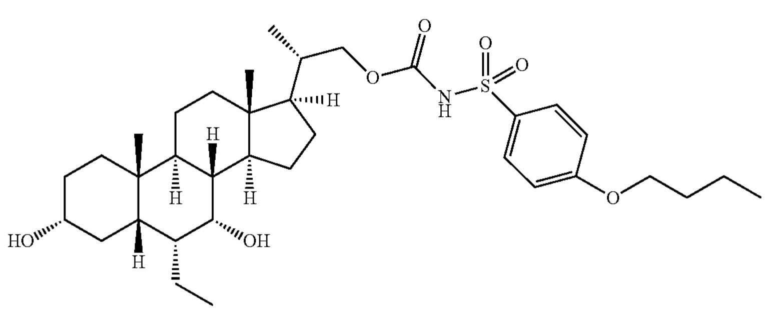 | 632.15 |

TABLE 4-continued

| Example # | Structure | MS data [M − 1]− |
|---|---|---|
| 22 | 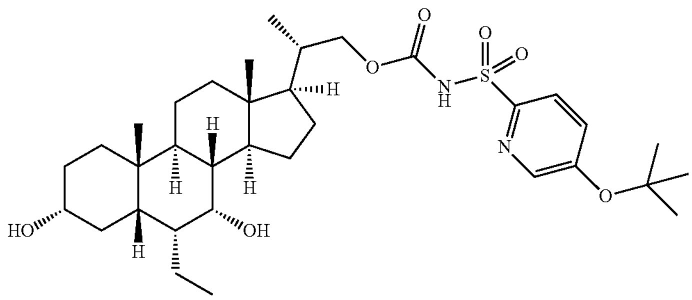 | 633.15 |
| 23 | 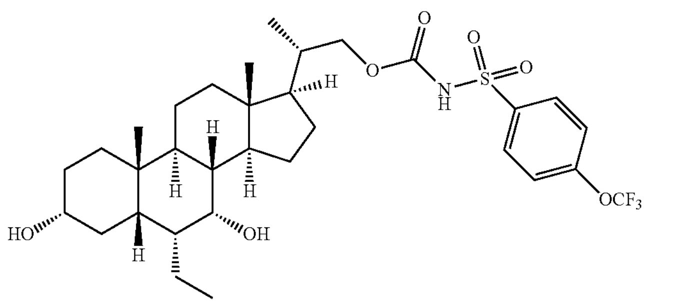 | 644.00 |
| 24 | 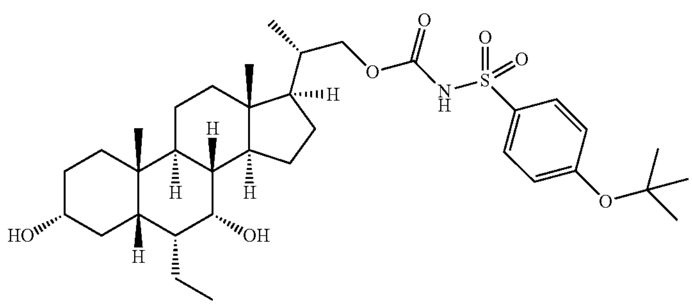 | 632.45 |
| 25 | 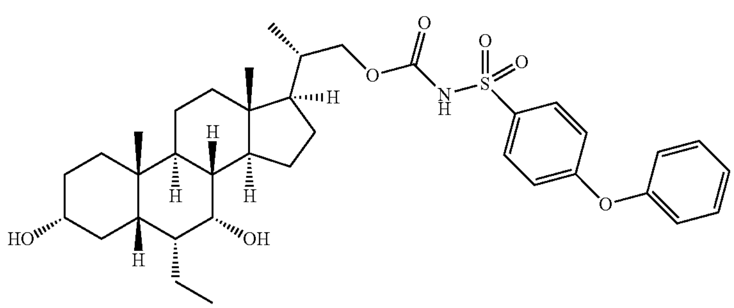 | 652.15 |
| 26 | 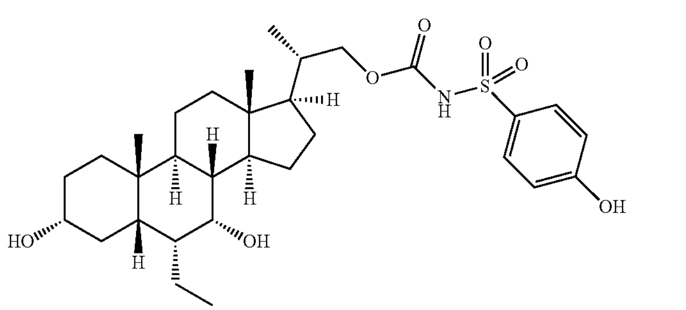 | 576.10 |

TABLE 4-continued

| Example # | Structure | MS data [M − 1]⁻ |
|---|---|---|
| 27 | 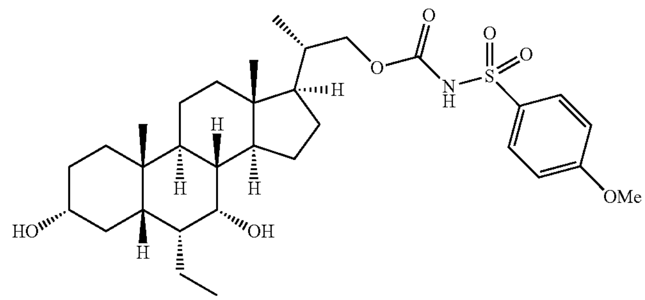 | 590.10 |
| 28 | 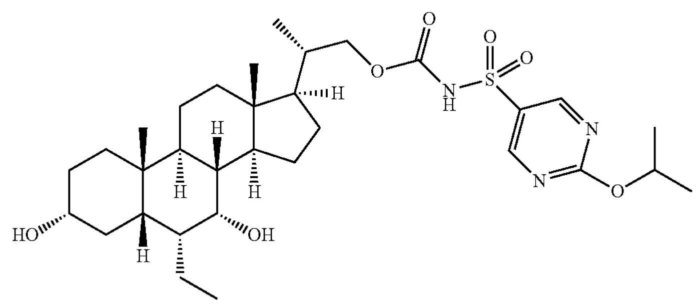 | 622.3 (M + 1) |
| 29 | 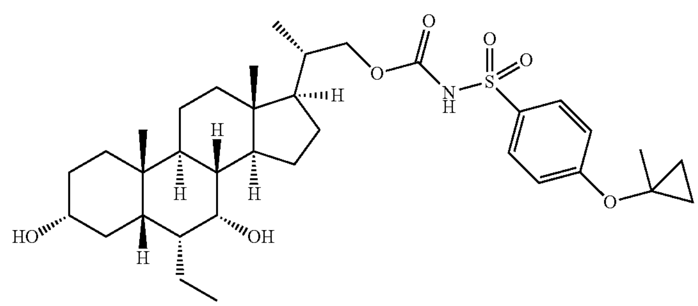 | 630.25 |
| 30 | 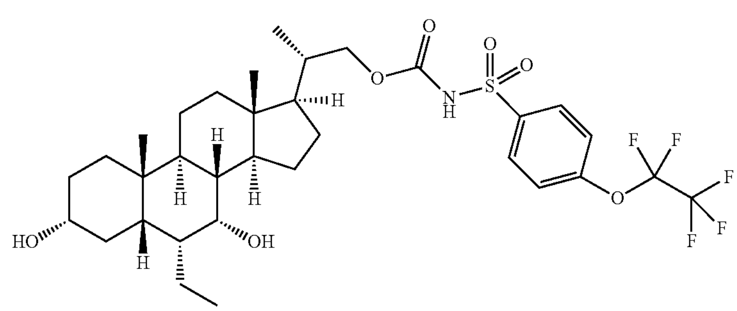 | 694.20 |

Example 31
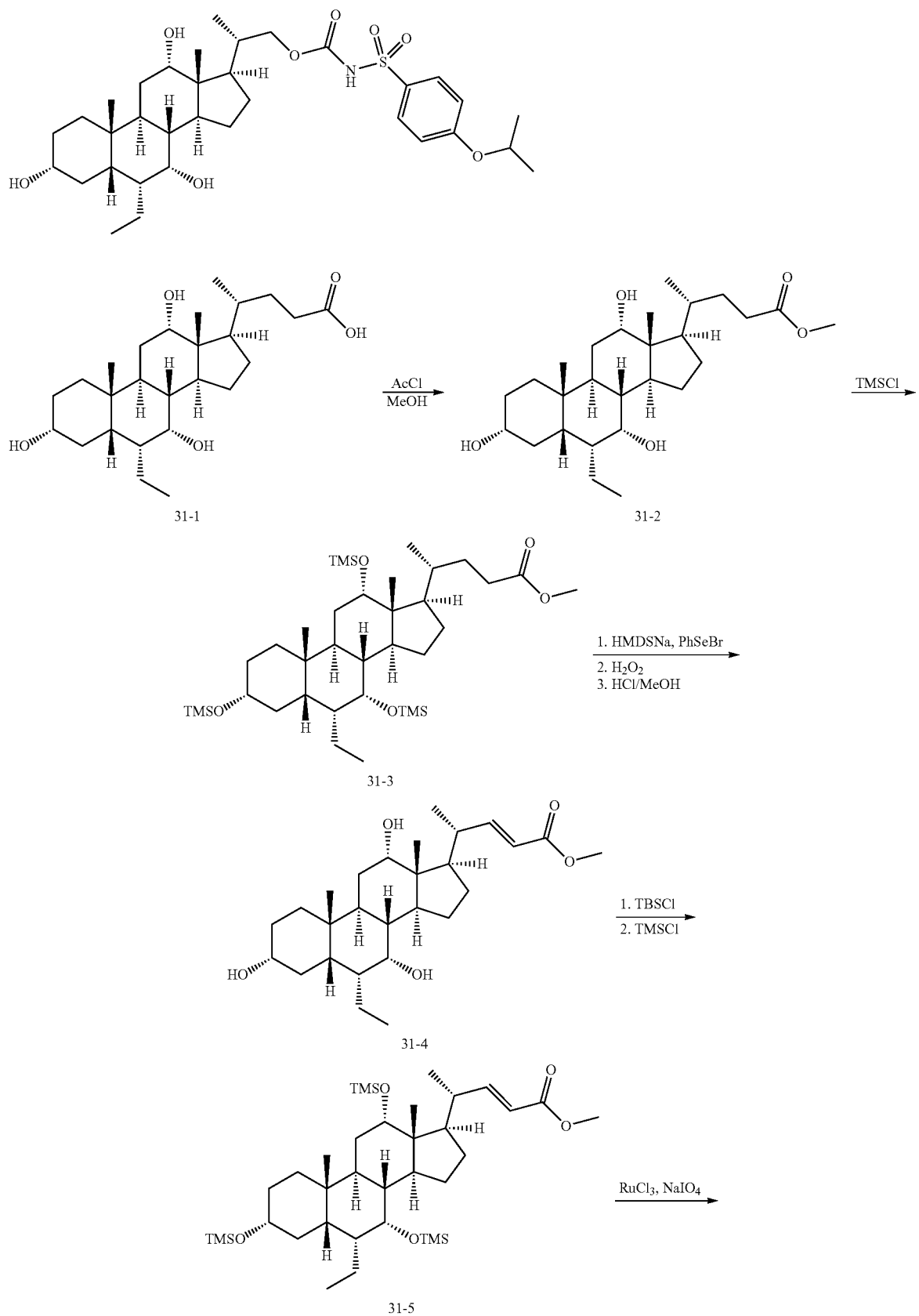
31-1 31-2 31-3 31-4 31-5

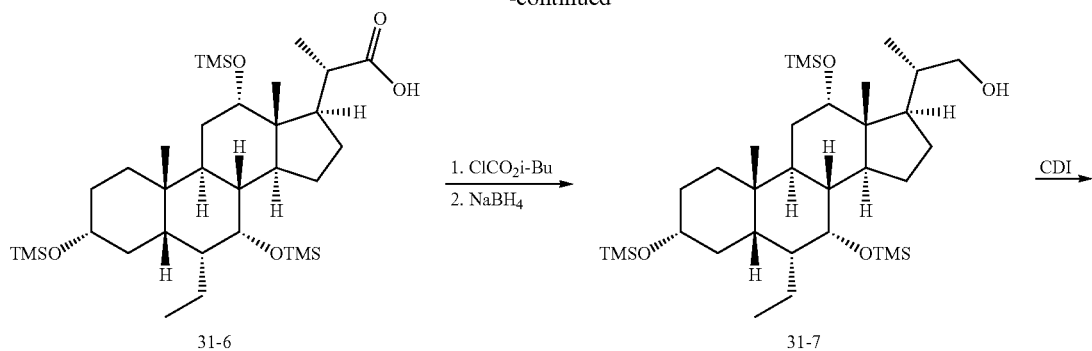
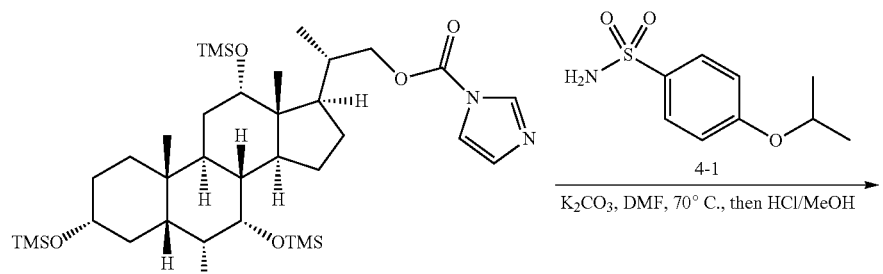
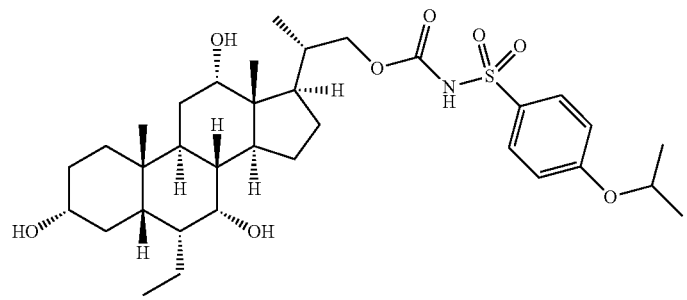
Example 31
Step 31-1:
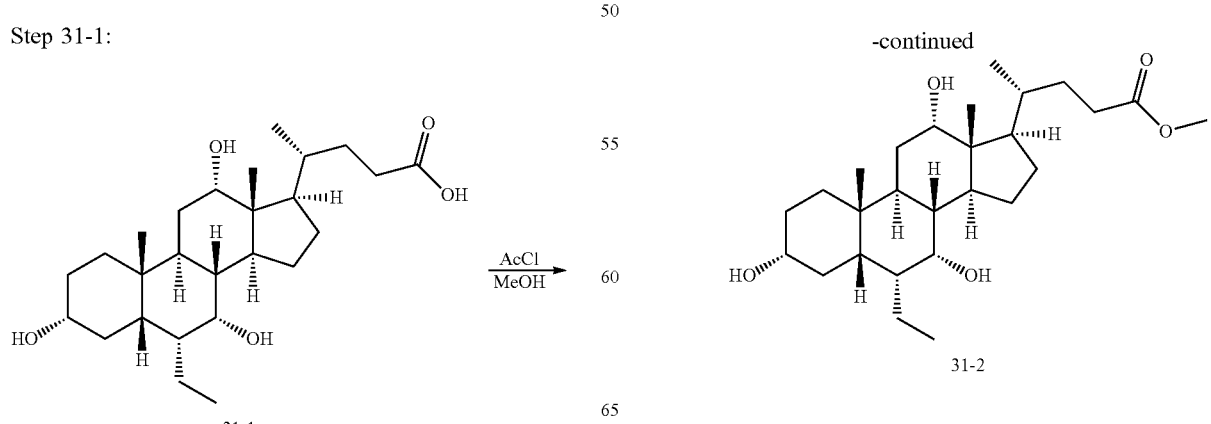
Acetyl chloride (1.1 g, 14.01 mmol) was added into a solution of 31-1 (*J. Med. Chem.* 2009, 52, 7958-7961) (6 g, 13.74 mmol) in methanol (60 mL). The resulting solution was stirred at room temperature for 1 h and concentrated under vacuum, which provided 5.7 g (92%) of 31-2 as a light brown solid.

Step 31-2:

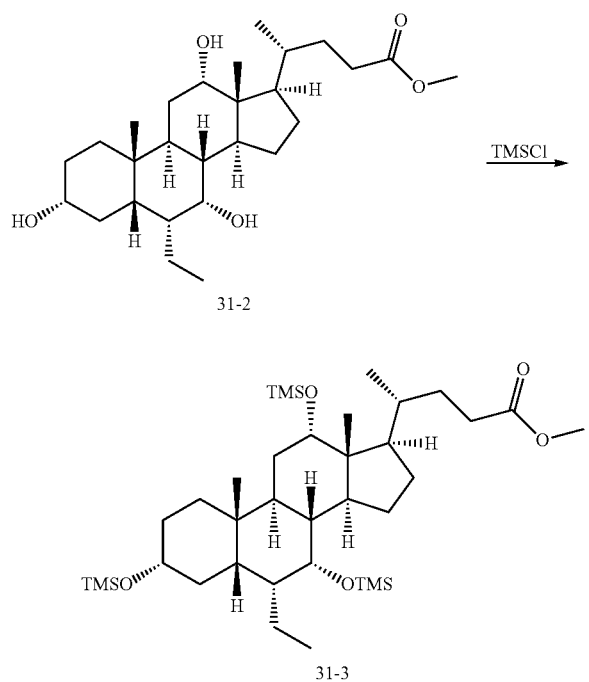

TMSCl (6.2 g, 57.07 mmol) was added into a solution of 31-2 (5.7 g, 12.65 mmol), 1-methylimidazole (7.8 g, 95.01 mmol), and N,O-bis(trimethylsilyl)acetamide (38.4 g, 188.76 mmol) in dichloromethane (100 mL). The mixture was stirred at room temperature overnight. Water (50 mL) was added and the mixture was extracted with dichloromethane (100 mL×3). The combined organic layers were washed with brine (100 mL), dried over anhydrous sodium sulfate, and concentrated under vacuum. The residue was purified on a silica gel column with ethyl acetate/petroleum ether (1:10), providing 5.9 g (70%) of 31-3 as a light brown solid.

Step 31-3:

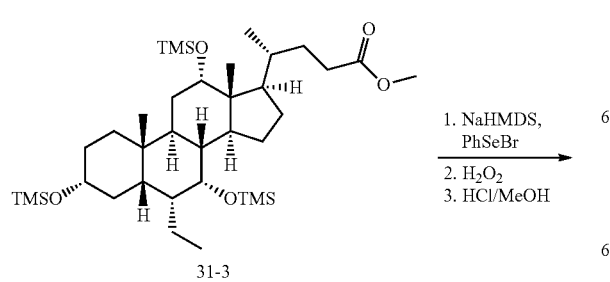

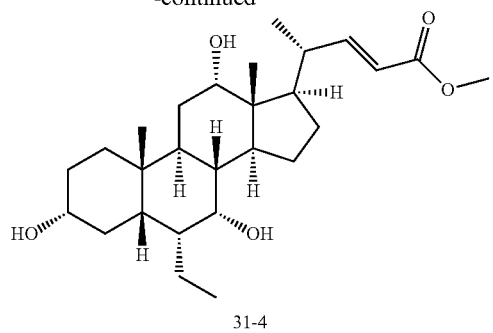

NaHMDS (2.0 M in THF, 22.1 mL) was added dropwise at −78° C. into a solution of 31-3 (5.9 g, 8.84 mmol) in tetrahydrofuran (100 mL) over a period of 30 min. The mixture was stirred at −78° C. for 1.5 h, and PhSeBr (2.5 g, 10.59 mmol) in THF (20 mL) was added dropwise. The mixture was stirred at −78° C. for 2 h and at room temperature for 30 min. Sat. NH$_4$Cl (30 mL) was added at 0° C., and the mixture was extracted with EtOAc (100 mL×2). The combined organic phase was washed with sat. brine (30 mL), dried over Na$_2$SO$_4$, and filtered.

The filtrate was treated with 30% H$_2$O$_2$ (10 mL) at 0° C., and the mixture was stirred at room temperature for 40 min. The reaction mixture was washed sequentially with sat. NaHCO$_3$ (30 mL) and sat. NaCl (30 mL). The organic layer was then dried over Na$_2$SO$_4$, filtered and concentrated.

The residue was dissolved in MeOH (50 mL) and 37% HCl (5 mL) was added. The resulting solution was stirred at room temperature for 10 min and concentrated under vacuum. Purification of the residue on a silica gel column with dichloromethane/methanol (20:1) afforded 2.3 g (58%) of 31-4 as a light brown solid.

Step 31-4:

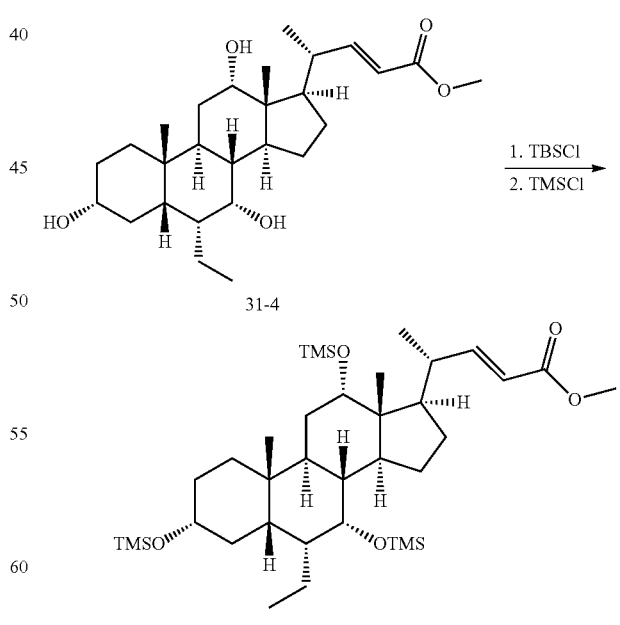

To a solution of 31-4 (2.1 g, 4.68 mmol) and TEA (2.4 g, 23.72 mmol) in dichloromethane (20 mL) was added TBSCl (2.8 g, 18.54 mmol) and the mixture was stirred at room temperature overnight. To the mixture was added 1-methylimidazole (1.9 g, 23.17 mmol), N,O-bis(trimethylsilyl)acetamide (9.5 g, 46.70 mmol), and TMSCl (1.5 g, 13.81 mmol). The resulting solution was stirred at room temperature for 2 h. Water (50 mL) was added and the mixture was extracted with dichloromethane (100 mL×3). The combined organic layers were washed with brine (100 mL), dried over anhydrous sodium sulfate, and concentrated under vacuum. Purification of the residue on a silica gel column with ethyl acetate/petroleum ether (1:10) afforded 2.1 g (63%) of 31-5 as a light brown solid.

Step 31-5:

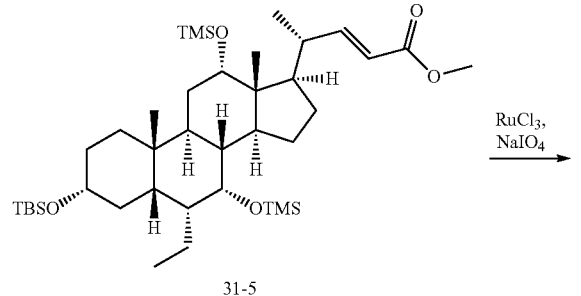

31-5

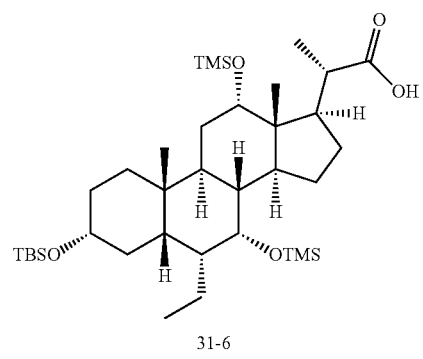

31-6

A solution of $K_2CO_3$ (3.7 g, 26.77 mmol) in water (5 mL) was added to a solution of 31-5 (1.9 g, 2.69 mmol) in EtOAc (10 mL) and $CH_3CN$ (10 mL). $RuCl_3$ hydrate (30 mg, 0.13 mmol) and $NaIO_4$ (5.8 g, 27.10 mmol) were added and the mixture was stirred at 70° C. overnight. The solution was diluted with MTBE (100 mL) and quenched with 10% citric acid. The aqueous phase was extracted with MTBE (50 mL×2). The combined organic layers were dried over anhydrous sodium sulfate and concentrated under vacuum. Purification of the residue on a silica gel column with dichloromethane/methanol (50:1) provided 670 mg (37%) of 31-6 as a light brown solid.

Step 31-6:

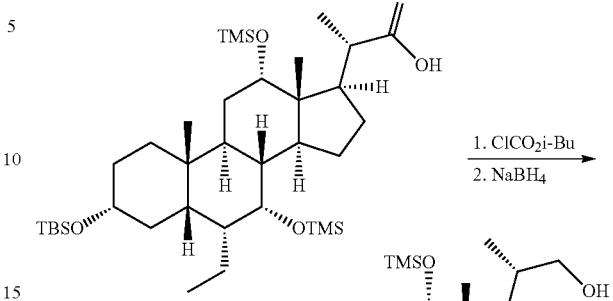

31-6

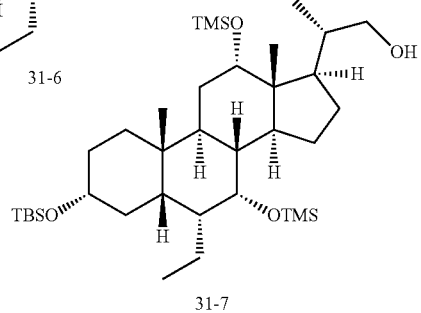

31-7

To a solution of 31-6 (670 mg, 1.00 mmol) and triethylamine (152 mg, 1.50 mmol) in DCM (10 mL) at 0° C. was added isobutyl chloroformate (164 mg, 1.20 mmol). The resulting mixture was stirred at this temperature for 1 h. The reaction solution was diluted with DCM (20 mL) and washed with water (10 mL) and brine (10 mL). The organic phase was dried over anhydrous sodium sulfate and concentrated under vacuum. The residue was dissolved in THF (10 mL) and $NaBH_4$ (152 mg, 4.02 mmol) was added at 0° C. The mixture was stirred at this temperature for 1 h. The reaction was quenched by water and extracted with EtOAc (10 mL×3). The combined organic layers were dried over anhydrous sodium sulfate and concentrated under vacuum, which provided 640 mg (98%) of 31-7 as a light brown solid.

Step 31-7:

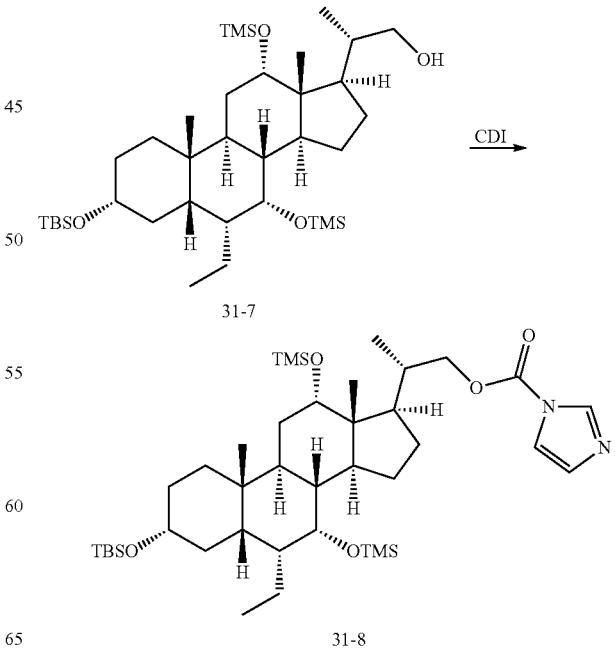

31-7

31-8

CDI (99 mg, 0.61 mmol) was added to a solution of 31-7 (400 mg, 0.61 mmol) and DIPEA (118 mg, 0.91 mmol) in DCM (10 mL). The mixture was stirred at room temperature for 3 h. Water (10 mL) was added and the mixture and extracted with DCM (20 mL×3). The combined organic phase was washed with saturated brine (20 mL), dried over anhydrous sodium sulfate, filtered, and concentrated to give compound 31-8 (450 mg, 98%) as a colorless oil, which was used directly without further purification.

Step 31-8:

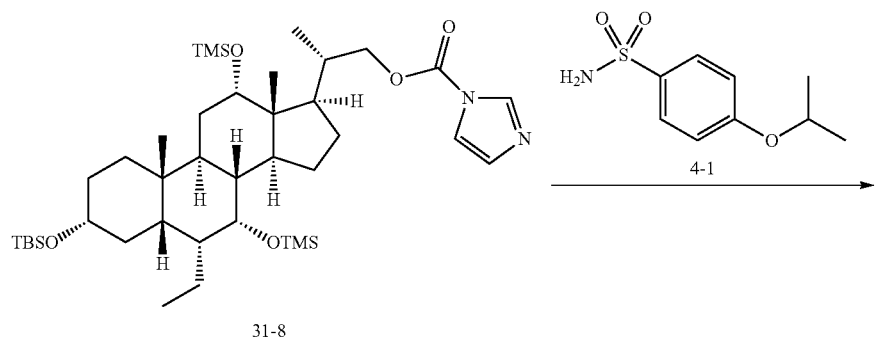

Intermediate 31-8 (100 mg, 0.134 mmol) was added to 4-isopropoxybenzenesulfonamide 4-1 (43 mg, 0.201 mmol) and K$_2$CO$_3$ (55 mg, 0.402 mmol) in THF (2 mL) and the mixture was stirred at 50° C. overnight. The mixture was cooled to room temperature, diluted with water (10 mL), and extracted with EtOAc (20 mL×3). The combined organic layers were dried over Na$_2$SO$_4$, filtered, and concentrated.

The residue was dissolved in MeOH (5 mL) and HCl (37%, 0.5 mL) was added. The mixture was stirred for 1 hour, neutralized with saturated NaHCO$_3$ (10 mL), and extracted with EtOAc (20 mL×3). The combined organic layers were dried over Na$_2$SO$_4$, filtered, and concentrated. The residue was purified by Flash-Prep-HPLC ((IntelFlash-1): Column, C18; mobile phase, MeCN/H$_2$O, Detector, UV 254 nm) to give Example 31 (14.1 mg) as a white solid. ESI-MS m/z, 634.25 [M-H]$^-$. $^1$H NMR (300 MHz, DMSO, ppm): δ 0.58 (3H, s), 0.75-1.05 (11H, m), 1.05-1.17 (2H, m), 1.25-1.31 (9H, m), 1.36-1.53 (7H, m), 1.63-1.67 (3H, m), 1.77-1.84 (2H, m), 1.96-2.11 (2H, m), 3.13 (1H, m), 3.48 (1H, m), 3.62-3.75 (4H, m), 3.94-3.98 (2H, m), 4.75 (1H, m), 7.11 (2H, d), 7.80 (2H, d).

Example 32

Example 32 was prepared by following procedures similar to that described Example 31. ESI-MS m/z, 660.30 [M-H]$^-$.

Example 33

Step 33-1:

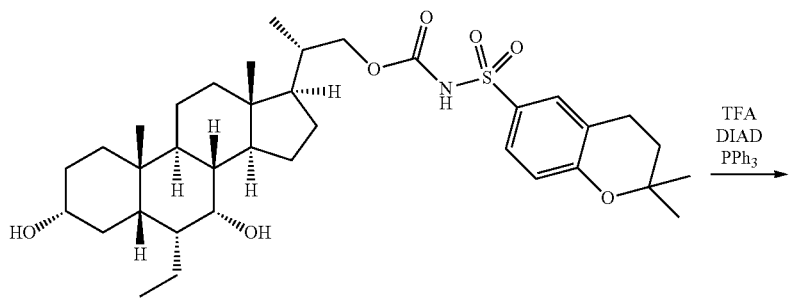

Example 5

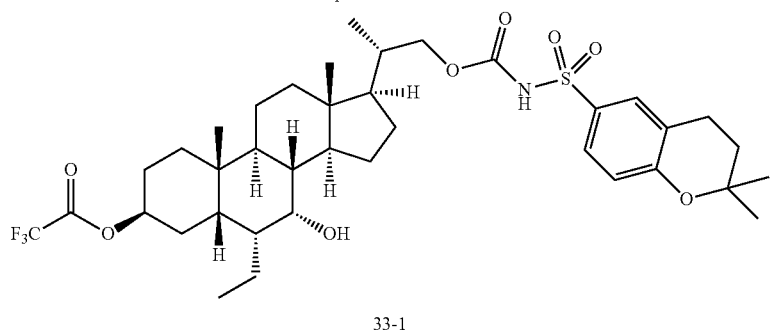

33-1

Example 5 (150 mg, 0.232 mmol) was dissolved in THF (2.322 mL) in a 2-dram vial. To the solution was added triphenylphosphine (152 mg, 0.581 mmol) and the resulting solution was cooled to 0° C. under $N_2$. TFA (0.045 mL, 0.581 mmol) and diisopropyl azodicarboxylate (0.113 mL, 0.581 mmol) were added respectively. The mixture was stirred at room temperature for 10 min, followed by the addition of sodium benzoate (84 mg, 0.581 mmol). The reaction was stirred at room temperature overnight, filtered, concentrated, and purified by CombiFlash (40 g $SiO_2$, EA/Hex: 0~100%) to give compound 33-1 (168.6 mg, 0.227 mmol, 98% yield). ESI-MS (m/z): 740.35 [M-H]⁻.

Step 33-2:

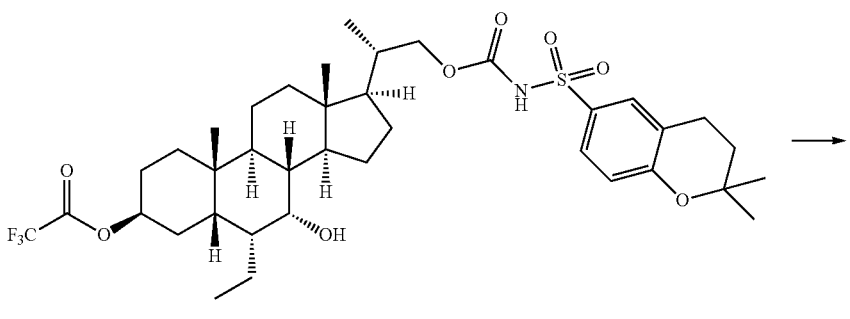

33-1

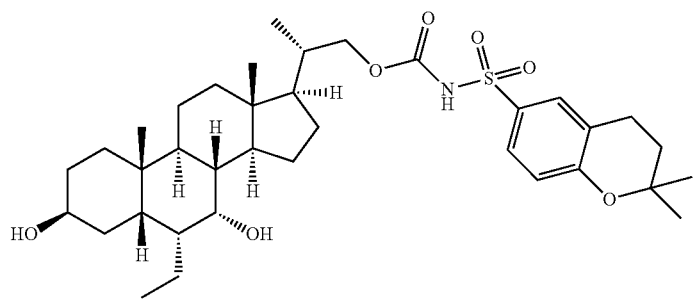

Example 33

Compound 33-1 (168.6 mg, 0.227 mmol) was dissolved in MeOH (3 mL) in a 2-dram vial and the solution was cooled to 0° C. After adding K$_2$CO$_3$ (75 mg, 0.545 mmol), the vial was stirred at room temperature for 16 h and diluted with EtOAc. The mixture was washed with 10% citric acid, sat. NaHCO$_3$, and brine respectively. The organic layer was dried over Na$_2$SO$_4$, filtered, and concentrated. The residue was purified by CombiFlash (20 g SiO$_2$, EA/Hex: 0~100%) to give Example 33 (99.4 mg, 0.154 mmol, 67.7% yield) as a white foam. ESI-MS (m/z): 644.36 [M-H]$^-$. NMR data: $^1$H NMR (400 MHz, Chloroform-d) δ 9.04 (s, 1H), 7.76 (d, J=0.4 Hz, 1H), 7.72 (dd, J=8.7, 0.4 Hz, 1H), 6.85 (d, J=8.7 Hz, 1H), 4.12-4.04 (m, 3H), 3.88 (dd, J=10.5, 5.4 Hz, 1H), 3.68 (br s, 1H), 2.82 (t, J=6.7 Hz, 2H), 2.13 (m, 1H), 1.96-1.68 (m, 5H), 1.35 (s, 6H), 1.00-0.92 (m, 6H), 0.86 (t, J=7.4 Hz, 3H), 0.64 (s, 3H).

Example 34

Step 34-1:

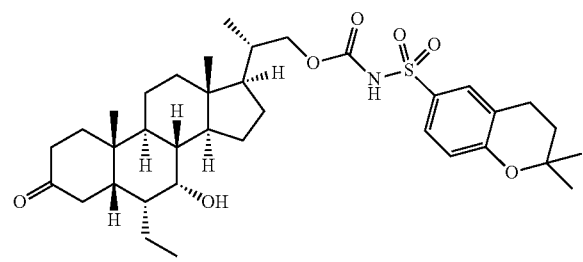

Example 5

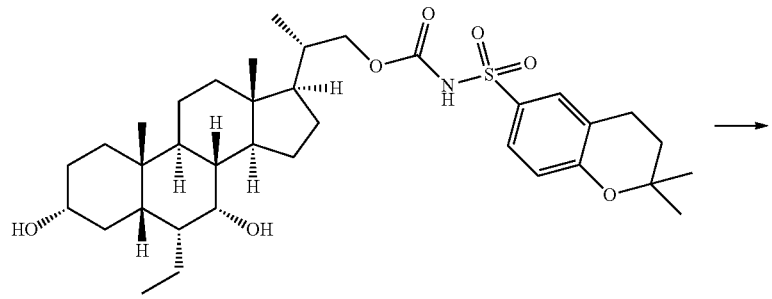

To a 25 mL round-bottomed flask was added Example 5 (150 mg, 0.232 mmol) and DCM (3.871 mL). To the solution at 0° C. was added bis(trimethylsilyl)acetamide (0.568 mL, 2.322 mmol), 1-methylimidazole (0.074 mL, 0.929 mmol) and TMSCl (0.089 mL, 0.697 mmol) respectively. The resulting mixture was allowed to warm to room temperature over 2.5 h. MeOH (7.73 mL) was added and the mixture was stirred at room temperature overnight. The reaction was diluted with EtOAc and washed with sat. NaHCO$_3$ and brine respectively. The organic layer was dried, filtered, concentrated to give 34-1 (136 mg, 0.189 mmol, 82% yield) as a white foam. ESI-MS (m/z): 716.40 [M-H]$^-$.

Step 34-2:

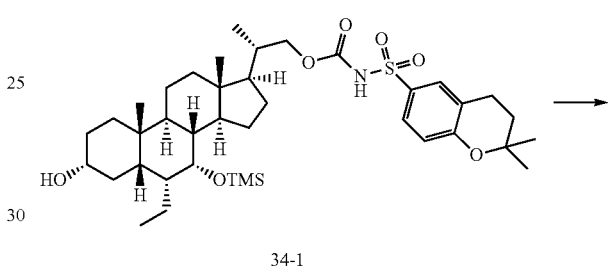

34-1

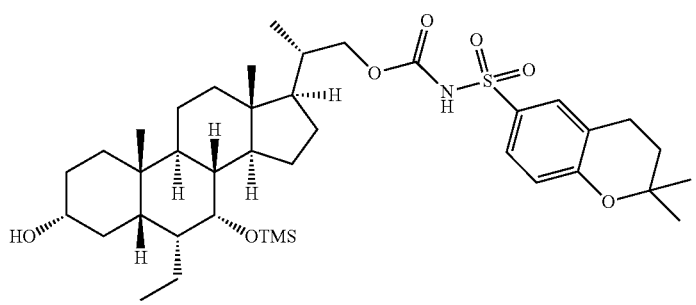

34-1

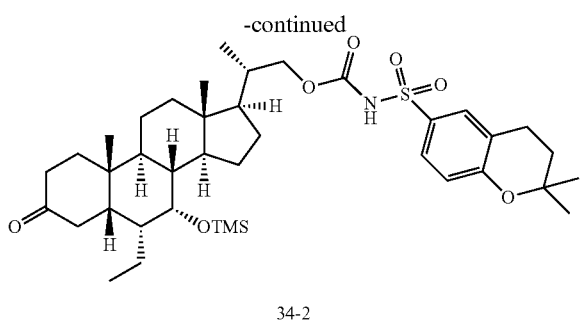

34-2

To a 2-dram vial containing 34-1 (136 mg, 0.189 mmol) was added DCM (3.8 mL) and sodium bicarbonate (80 mg, 0.947 mmol). The mixture was cooled to 0° C. and Dess-Martin periodinane (96 mg, 0.227 mmol) was added. The cold bath was removed and the mixture was stirred at room temperature for 4 h. The reaction was diluted with EtOAc and washed with sat. NaHCO$_3$ and brine. The organic layer was dried, filtered, concentrated, and purified by Combi-Flash (20 g SiO$_2$, EA/Hex: 0~100%) to give 34-2 (119 mg, 0.166 mmol, 88% yield). ESI-MS (m/z): 714.39 [M-H]$^-$.

Step 34-3:

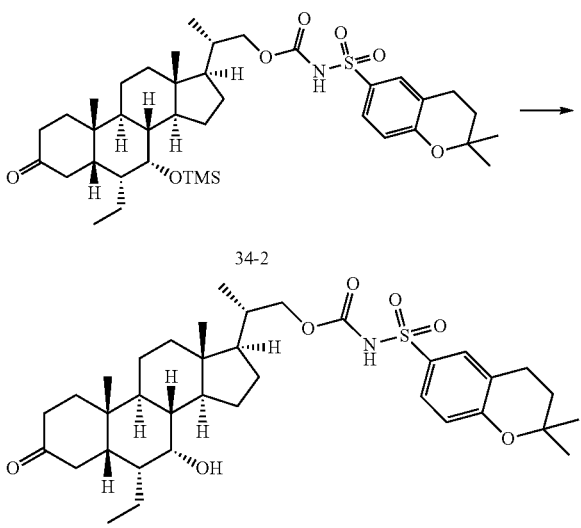

Example 34

To a 2-dram vial was added a solution of 34-2 (119 mg, 0.166 mmol) in MeOH (5 mL) and a drop of 37% HCl solution (0.014 mL, 0.166 mmol). The resulting solution was stirred at room temperature for 35 min and diluted with EtOAc. The mixture was washed with sat. NaHCO$_3$ solution and brine respectively. The organic layer was dried, filtered, and concentrated to give a white foam (97.3 mg). The foam was purified by Combiflash (12 g SiO$_2$, EA/Hex: 0~100%) to example 34 (97 mg, 0.151 mmol, 91% yield) as a white solid. ESI-MS (m/z): 642.35 [M-H]$^-$.

Assays

Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. EC$_{50}$ and efficacy (normalize to CDCA set as 100%) is determined by XLFit. The assay is according to the manufacturer's instructions. In brief, the assay was performed in white, 96 well plates using final volume of 100 uL containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. EC$_{50}$ and Efficacy (normalize to CDCA set as 100%) is determined by XLFit.

To assess the FXR agonistic potency of the example compounds as well as for reference compound, potency ranges were determined in the Human FXR (NR1H4) Assay as listed below in Table 4. (A=EC50<1 nM; B=1 nM<EC50<10 nM; C=10 nM<EC50<100 nM; D=EC50>100 nM).

| Example # | EC50 | Example # | EC50 |
|---|---|---|---|
| 1 | B | 2 | C |
| 3 | D | 4 | A |
| 5 | A | 6 | A |
| 7 | A | 8 | A |
| 9 | A | 10 | A |
| 11 | B | 12 | A |
| 13 | A | 14 | A |
| 15 | A | 16 | A |

| Example # | EC50 | Example # | EC50 |
| --- | --- | --- | --- |
| 17 | A | 18 | A |
| 19 | C | 20 | B |
| 21 | B | 22 | A |
| 23 | D | 24 | A |
| 25 | D | 26 | D |
| 27 | B | 28 | C |
| 29 | A | 30 | B |
| 31 | D | 32 | D |
| 33 | A | 34 | A |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula I or a pharmaceutically acceptable salt, ester or prodrug thereof:

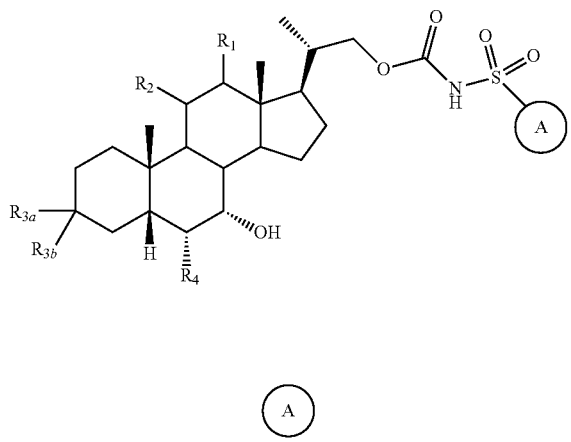

(I)

A is

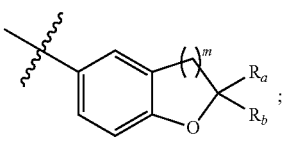

$R_a$ and $R_b$ are independently selected from the group consisting of:
1) Hydrogen,
2) Optionally substituted —$C_1$-$C_8$ alkyl,
3) Optionally substituted —$C_2$-$C_8$ alkenyl,
4) Optionally substituted —$C_2$-$C_8$ alkynyl,
5) Optionally substituted —$C_3$-$C_8$ cycloalkyl,
6) Optionally substituted aryl,
7) Optionally substituted arylalkyl,
8) Optionally substituted 3- to 8- membered heterocycloalkyl,
9) Optionally substituted heteroaryl, and
10) Optionally substituted heteroarylalkyl;

m is selected from 1, 2 or 3;

$R_1$ is optionally substituted $C_1$-$C_6$ alkyl, hydrogen, hydroxyl, —$OSO_3H$, —$OSO_3^-$, —OAc, —$OPO_3H_2$ or —$OPO_3^{2-}$;

$R_2$ is optionally substituted $C_1$-$C_6$ alkyl, hydrogen, halogen, CN, $N_3$, hydroxyl, —$OSO_3H$, —$OSO_3^-$, —OAc, —$OPO_3H_2$, —$OPO_3^{2-}$, —$SR_a$ or —$NHR_a$, wherein $R_a$ is previously defined; alternatively, $R_1$ and $R_2$ are taken together with the carbon atoms to which they attached to form —CH═CH— or cycloalkyl ring or heterocycloalkyl ring;

$R_{3a}$ and $R_{3b}$ are independently selected from hydrogen, hydroxyl, optionally substituted $C_1$-$C_6$ alkyl, or optionally substituted —O—$C_1$-$C_6$ alkyl; alternatively, $R_{3a}$ and $R_{3b}$ are taken together with the carbon atom to which they attached to form —C(O); and $R_4$ is selected from the group consisting of:
1) Hydrogen,
2) Halogen,
3) Optionally substituted —$C_1$-$C_8$ alkyl,
4) Optionally substituted —$C_2$-$C_8$ alkenyl,
5) Optionally substituted —$C_2$-$C_8$ alkynyl, and
6) Optionally substituted —$C_3$-$C_8$ cycloalkyl.

2. The compound of claim 1, represented by Formula (Ia) or Formula (Ib), or a pharmaceutically acceptable salt, ester or prodrug thereof,

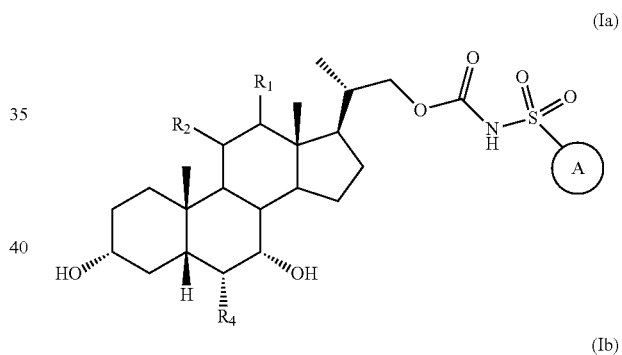

(Ia)

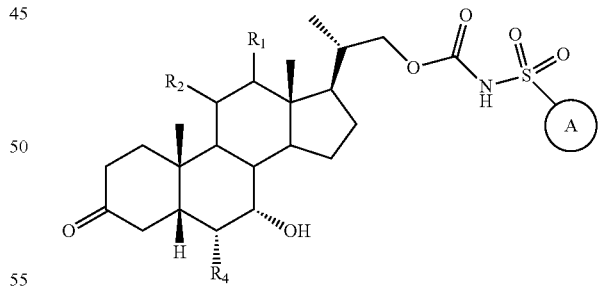

(Ib)

wherein $R_1$, $R_2$, $R_4$, and

are as defined in claim 1.

3. The compound of claim 1, represented by Formula (IIIa) or Formula (IIIb), or a pharmaceutically acceptable salt, ester or prodrug thereof, (IIIa)
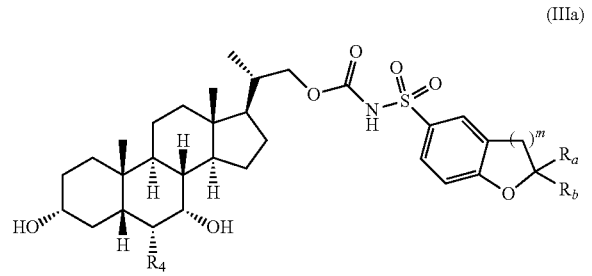
(IIIb)
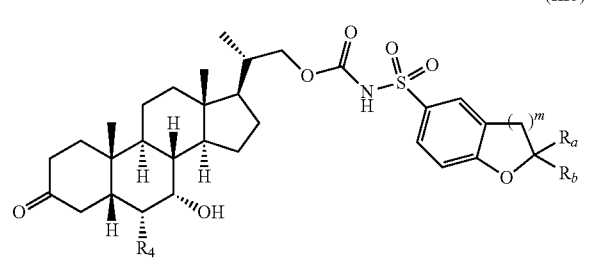
wherein $R_4$, $R_a$, $R_b$, and m are as defined in claim 1.
4. The compound of claim 1, selected from the compounds set forth below or a pharmaceutically acceptable salt, ester or prodrug thereof:
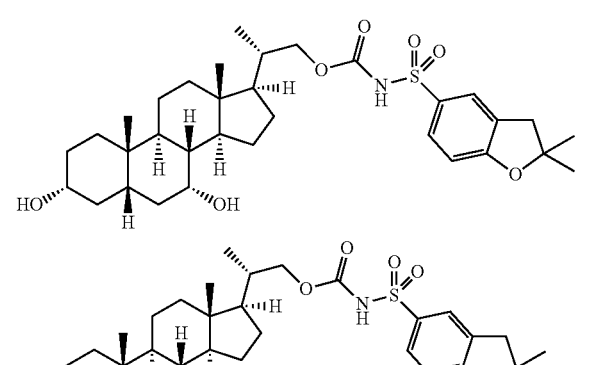
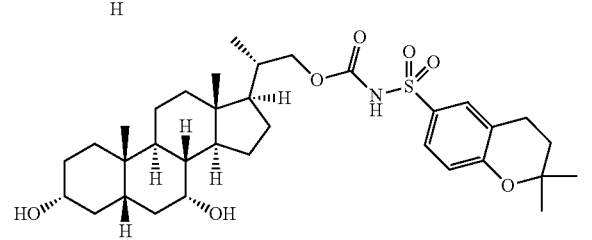
-continued
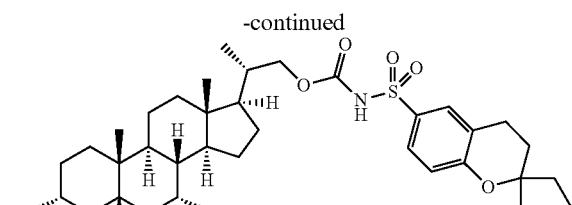
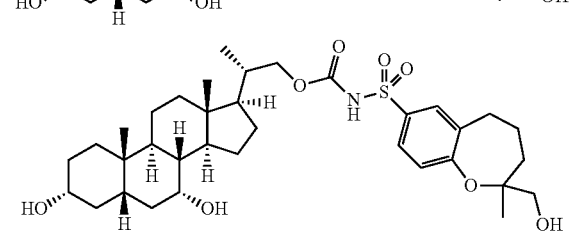

105
-continued
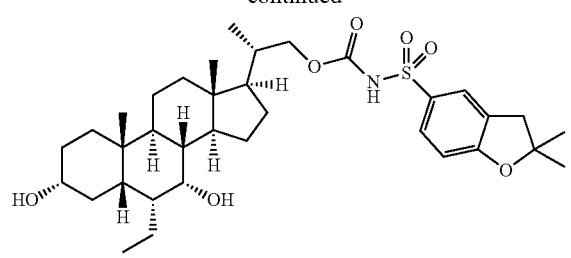
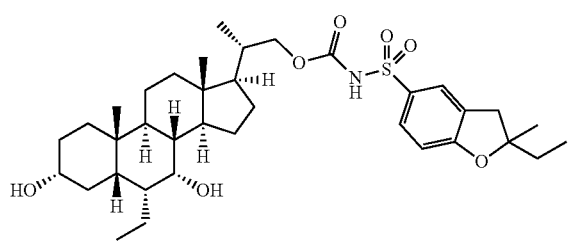
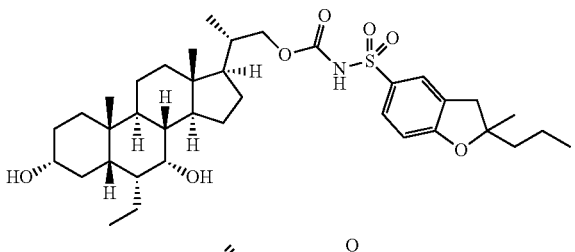
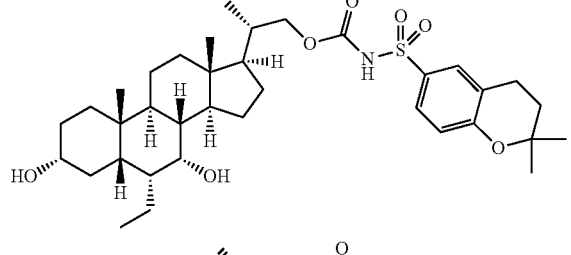
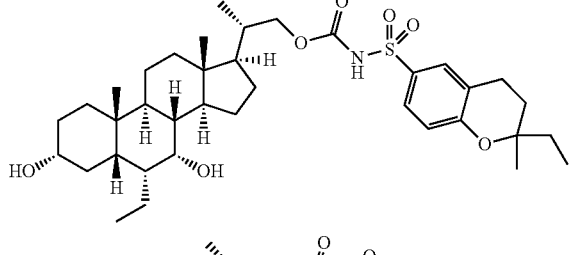
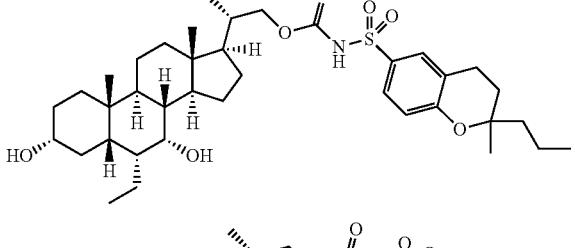
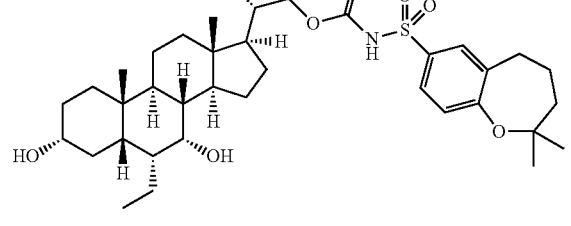
106
-continued
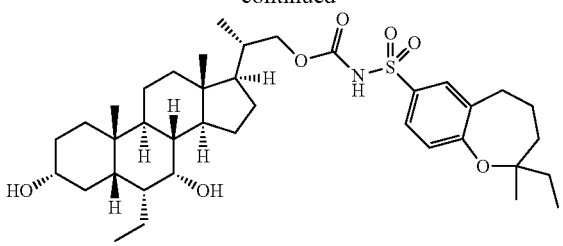
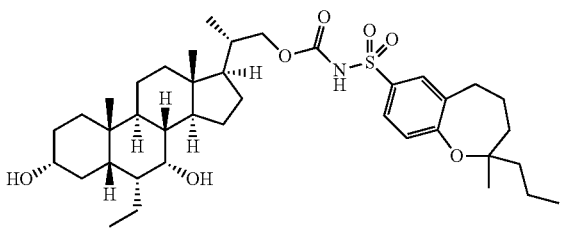
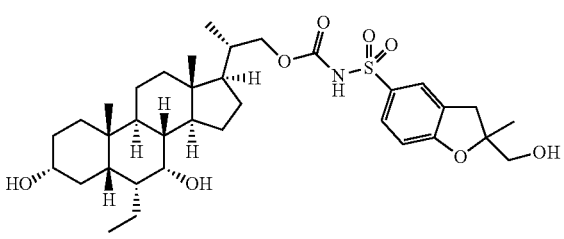
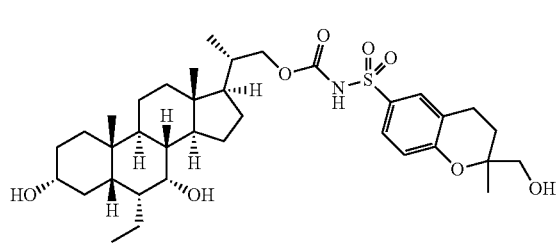
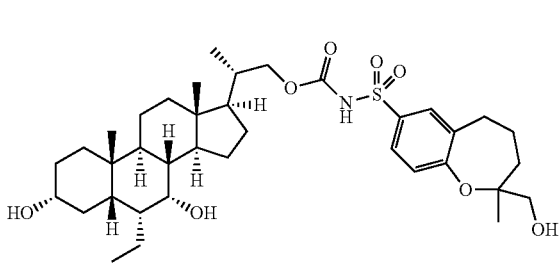
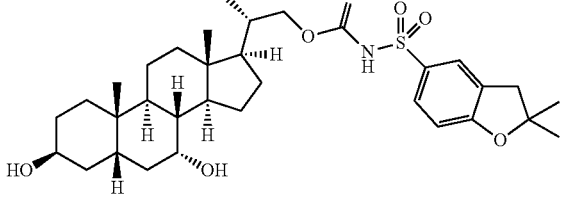
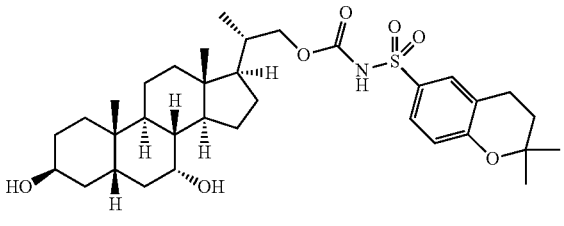

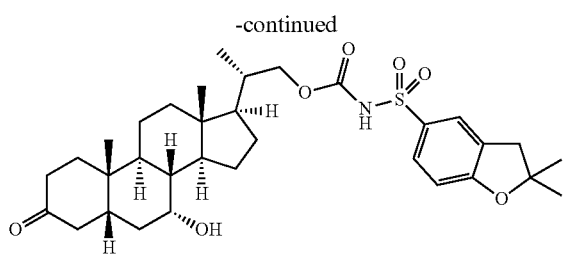

5. The compound of claim 1, selected from the compounds set forth below or a pharmaceutically acceptable salt, ester or prodrug thereof:

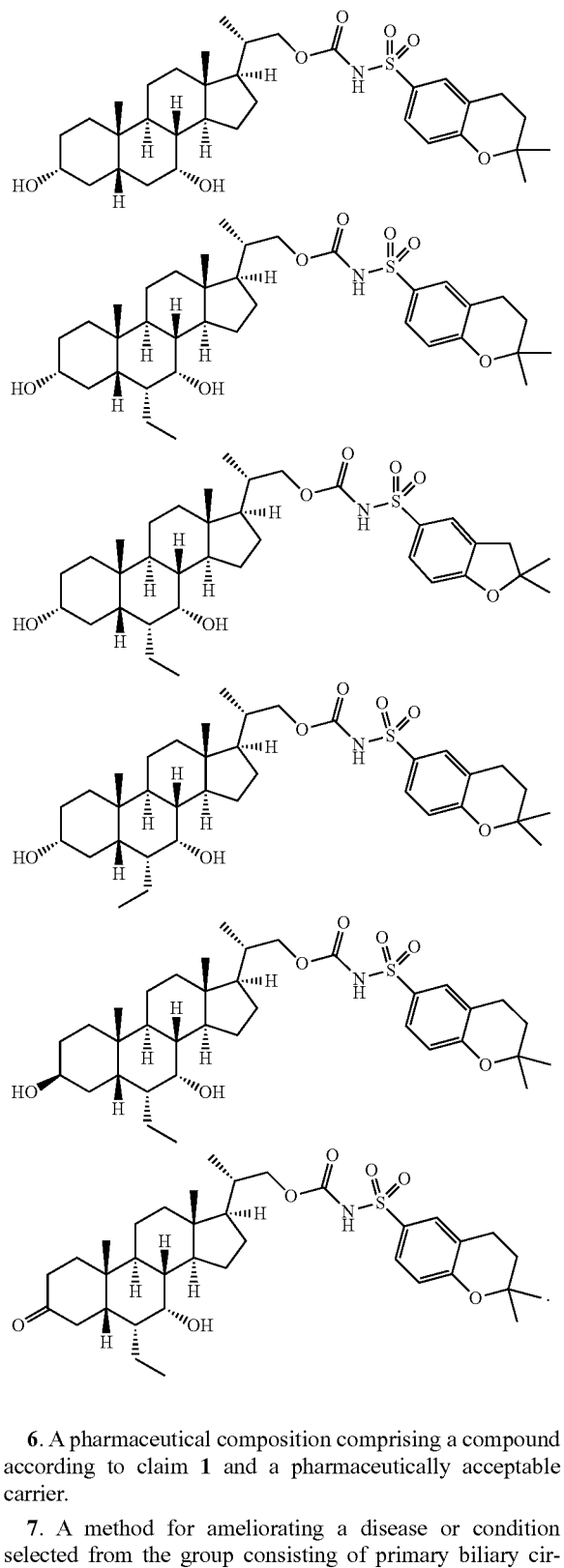

6. A pharmaceutical composition comprising a compound according to claim 1 and a pharmaceutically acceptable carrier.

7. A method for ameliorating a disease or condition selected from the group consisting of primary biliary cirrhosis, cerebrotendinous xanthomatosis, primary sclerosing cholangitis, alcoholic liver disease, nonalcoholic fatty liver disease, nonalcoholic steatohepatitis, atherosclerosis, hypercholesterolemia, hypertriglyceridemia, Type II diabetes, and hepatocellular carcinoma in a subject in need thereof, comprising administering to the subject a therapeutically effective amount of a compound according to claim 1.

8. A method of ameliorating primary biliary cirrhosis in a subject in need thereof, comprising administering to the subject a therapeutically effective amount of a compound of claim 1.

9. A method of ameliorating nonalcoholic steatohepatitis in a subject in need thereof, comprising administering to the subject a therapeutically effective amount of a compound of claim 1.

10. A method of ameliorating nonalcoholic fatty liver disease in a subject in need thereof, comprising administering to the subject a therapeutically effective amount of a compound of claim 1.

* * * * *